United States Patent
Miura et al.

(10) Patent No.: US 10,537,433 B2
(45) Date of Patent: Jan. 21, 2020

(54) LIGAMENT RECONSTRUCTION TYPE ARTIFICIAL KNEE JOINT

(71) Applicant: National University Corporation Ehime University, Ehime (JP)

(72) Inventors: Hiromasa Miura, Ehime (JP); Kazunori Hino, Ehime (JP)

(73) Assignee: National University Corporation Ehime University, Ehime (JP)

( * ) Notice: Subject to any disclaimer, the term of this patent is extended or adjusted under 35 U.S.C. 154(b) by 280 days.

(21) Appl. No.: 15/522,392

(22) PCT Filed: Oct. 31, 2015

(86) PCT No.: PCT/JP2015/080867
§ 371 (c)(1),
(2) Date: Apr. 27, 2017

(87) PCT Pub. No.: WO2016/068340
PCT Pub. Date: May 6, 2016

(65) Prior Publication Data
US 2017/0333193 A1    Nov. 23, 2017

(30) Foreign Application Priority Data
Oct. 31, 2014   (JP) .................................. 2014-223468

(51) Int. Cl.
*A61F 2/38* (2006.01)
*A61F 2/08* (2006.01)
(Continued)

(52) U.S. Cl.
CPC .................. *A61F 2/38* (2013.01); *A61F 2/08* (2013.01); *A61F 2/64* (2013.01); *A61F 2002/2825* (2013.01); *A61F 2002/2892* (2013.01)

(58) Field of Classification Search
CPC ...... A61F 2/08; A61F 2/28; A61F 2/38; A61F 2/64
See application file for complete search history.

(56) References Cited

U.S. PATENT DOCUMENTS

| 6,755,864 B1 | 6/2004 | Brack et al. |
| 2003/0153977 A1 | 8/2003 | Suguro et al. |

(Continued)

FOREIGN PATENT DOCUMENTS

| FR | 2634373 A1 | 1/1990 |
| JP | 2001-120583 A | 5/2001 |

(Continued)

*Primary Examiner* — Jason-Dennis N Stewart
(74) *Attorney, Agent, or Firm* — Foley & Lardner LLP

(57) ABSTRACT

There is provided a ligament reconstruction type artificial knee joint that can exert a function of an anterior cruciate ligament in an original knee joint.

In an artificial knee joint 1 used in a total knee replacement, the artificial knee joint 1 includes: a femur member 10 mounted on a femur distal end DT; a tibia member 20 mounted on a tibia proximal end PE; and an artificial ligament 30 coupling the tibia member 20 and the femur member 10 together. One end of the artificial ligament 30 is coupled to a position where once an anterior cruciate ligament ACL exists in a knee replaced for the artificial knee joint 1 on an inside of a lateral condyle of the femur member 10, and the other end of the artificial ligament 30 is coupled to a position where once the anterior cruciate ligament ACL exists in the knee replaced for the artificial knee joint 1 on an upper side of the tibia member 20.

15 Claims, 65 Drawing Sheets

(51) Int. Cl.
*A61F 2/64* (2006.01)
*A61F 2/28* (2006.01)

(56) References Cited

U.S. PATENT DOCUMENTS

| | | |
|---|---|---|
| 2010/0191342 A1 | 7/2010 | Byrd et al. |
| 2010/0286788 A1 | 11/2010 | Komistek |
| 2015/0045900 A1 | 2/2015 | Byrd et al. |

FOREIGN PATENT DOCUMENTS

| | | |
|---|---|---|
| JP | 2003-230582 A | 8/2003 |
| JP | 2003-265506 A | 9/2003 |
| JP | 2010-172569 A | 8/2010 |
| JP | 2011-502608 A | 1/2011 |
| JP | 2012-165978 A | 9/2012 |
| JP | 2013-517911 A | 5/2013 |
| JP | 2013-172992 A | 9/2013 |
| WO | WO 2005/002473 A1 | 1/2005 |
| WO | WO 2009/056836 A2 | 5/2009 |
| WO | WO 2010/088229 A2 | 8/2010 |
| WO | WO 2011/094540 A2 | 8/2011 |

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

(A)

(B)

LIGAMENT RECONSTRUCTION TYPE ARTIFICIAL KNEE JOINT

TECHNICAL FIELD

The present invention relates to a ligament reconstruction type artificial knee joint.

BACKGROUND ART

A knee joint is a joint that is constructed with a femur, a tibia, and a kneepan. A knee cartilage or a meniscus is located between a distal end of the femur and a proximal end of the tibia, and acts as a cushion in the knee joint, whereby the knee joint can smoothly work.

However, when the knee cartilage or the meniscus is worn off due to fatness or aging, not only a cushioning property between the distal end of the femur and the proximal end of the tibia is lost, but also the knee joint is possibly deformed. The knee joint is deformed when joint rheumatism is gotten, or when the knee is injured. For the deformation (knee osteoarthritis) of the knee joint, the knee joint cannot smoothly work, but a patient feels a bad pain in walking, and sometimes the patient has difficulty walking.

A total knee replacement is adopted as a treatment technique for the knee osteoarthritis. In the total knee replacement, the distal end of the femur and the proximal end of the tibia are cut off, and the cut portion is replaced with the artificial knee joint. Currently many patients are subjected to the total knee replacement, which allows relief of the pain or performance of the normal walking. Therefore, many patients is highly satisfied with the total knee replacement. There have been developed many artificial knee joints used in the total knee replacement (see Patent Documents 1 and 2).

In the knee joint, the femur and the tibia are joined to each other by a ligament in order to stabilize the working and attitude of the knee joint. However, sometimes the ligament joined to the distal end of the femur and the proximal end of the tibia, namely, an anterior cruciate ligament or a posterior cruciate ligament is cut off because the distal end of the femur and the proximal end of the tibia are cut off in performing the total knee replacement. Currently there are two methods, namely, a method (see Patent Document 1) in which both the cruciate ligaments are cut off to substitute a ligament function for the artificial knee joint and a method (see Patent Document 2) in which the anterior cruciate ligament is cut off while the posterior cruciate ligament is preserved. The method to be adopted is selected according to a damaged condition of the joint or ligament.

The anterior cruciate ligament is removed in both the methods. Although the artificial knee joint can be substituted for the function of the anterior cruciate ligament, the artificial knee joint is far inferior to the function of the original anterior cruciate ligament. Therefore, a patient having the artificial knee joint does not feel inconvenience in normal walking too much, but feels inconvenience when going up and down the stairs.

A patient having the artificial knee joint due to an injury of sports has a strong demand to do sports even if having the artificial knee joint. However, the above methods cannot respond to the demand.

An artificial knee joint having a form of preserving the anterior cruciate ligament is also developed in order to respond to the demand (Patent Document 3). However, the anterior cruciate ligament is frequently damaged in the knee osteoarthritis, and sometimes a ligament length changes in association with the joint deformation. In the artificial knee joint of Patent Document 3, even if the anterior cruciate ligament is preserved, the anterior cruciate ligament hardly exerts the sufficient function. In the knee osteoarthritis caused by the damaged anterior cruciate ligament, even if the anterior cruciate ligament is preserved, the function of the anterior cruciate ligament can hardly be expected to be exerted.

Patent Document 4 discloses a technique of joining a femur member and a tibia member to each other using an artificial material as a mechanism preventing mobilization of an insert in an artificial knee joint including the tibia member and an insert mobile mechanism (a mechanism in which the insert moves on the tibia member with a freedom degree). In the technique of Patent Document 4, an end of a tibia-side member of the artificial material is joined to the tibia-side member with an elastic member such as a spring interposed therebetween, which allows a coupling structure to have a cushioning characteristic.

PRIOR ART DOCUMENTS

Patent Documents

Patent Document 1: JP-A-2013-172992
Patent Document 2: JP-A-2001-120583
Patent Document 3: JP-T-2013-517911
Patent Document 4: JP-T-2011-502608

SUMMARY OF THE INVENTION

Problems to be Solved by the Invention

In the technique of Patent Document 4, there is a function of connecting the femur member and the tibia member to each other because the artificial material is provided between the femur member and the tibia member. However, in the technique of Patent Document 4, a layout and a joining position of the ligament are insufficiently considered although the layout and the joining position are important for the anterior cruciate ligament to exert an original function.

As described above, although various artificial knee joints have been developed, an artificial knee joint in which the function of the anterior cruciate ligament in the original knee joint can sufficiently be exerted has not been developed yet. Therefore, there is a demand to develop the artificial knee joint in which the original function can sufficiently be exerted.

Because an individual difference exists in a state (such as tensile force) of the anterior cruciate ligament, there is also a simultaneous demand for development of the artificial knee joint having a function of reproducing the tension of the anterior cruciate ligament unique to a patient.

An object of the present invention is to provide a ligament reconstruction type artificial knee joint that can exert a function of the anterior cruciate ligament in the original knee joint.

Another object of the present invention is to provide a ligament reconstruction type artificial knee joint that can exert functions of the anterior cruciate ligament and posterior cruciate ligament in the original knee joint.

Means for Solving the Problems (Anterior Cruciate Ligament)
A ligament reconstruction type artificial knee joint used in a total knee replacement, the artificial knee joint comprising:

a femur member mounted on a femur distal end;

a tibia member mounted on a tibia proximal end;

a ring-shaped artificial ligament coupling the tibia member and the femur member together; and a coupling member to which the artificial ligament is coupled, wherein the femur member includes a wall-shaped lateral condyle inside wall, which is disposed on an inside of a lateral condyle of a femur when the femur member is mounted on the femur distal end, in the femur member, an engagement part on which one end of the artificial ligament is hooked at a position corresponding to a position, where once an anterior cruciate ligament exists in a knee replaced for the artificial knee joint in the lateral condyle inside wall when the femur member is mounted on the femur distal end, such that the artificial ligament pierces the lateral condyle inside wall, a fixing hole in which the coupling member is fixedly inserted is made at a position corresponding to a position, where once the anterior cruciate ligament exists in the knee replaced for the artificial knee joint on an upper side of the tibia member, the artificial ligament is formed into a ring shape as a whole, a pair of through-holes is made in one end face of the coupling member, the artificial ligament is hooked while inserted in the pair of through-holes, the engagement part includes a pair of engagement holes on which the artificial ligament is hooked, and the pair of engagement holes is made such that twist is generated in the artificial ligament when the artificial ligament is hooked, and when the coupling member is mounted in the fixing hole of the tibia member.

According to a second aspect, in the ligament reconstruction type artificial knee joint of the first aspect, a substantially V-shaped groove is formed around the engagement part such that a leading end of the engagement part is directed toward a front of the knee, the groove piercing the lateral condyle inside wall, and the pair of engagement holes communicating with the groove is made in a base end of the engagement part.

According to a third aspect, in the ligament reconstruction type artificial knee joint of the first aspect, the artificial ligament is formed into a ring shape, the coupling member includes: a pair of enlarged-diameter parts provided at both ends in an axial direction; and a neck part on which the artificial ligament disposed between the pair of enlarged-diameter parts is hooked. In the coupling member, a notch in which the artificial ligament is disposed is provided in the enlarged-diameter part, which is disposed on a top surface side of the tibia member when the coupling member is mounted in the fixing hole of the tibia member, a substantially V-shaped groove is formed around the engagement part such that a leading end of the engagement part is directed toward a front of the knee, the groove piercing the lateral condyle inside wall, a pair of engagement holes communicating with the groove is made in a base end of the engagement part, and a direction in which the pair of engagement holes is arrayed is provided such that twist is generated in the artificial ligament when the artificial ligament is hooked on the pair of engagement holes, and when the coupling member is mounted in the fixing hole of the tibia member.

According to a fourth aspect, the ligament reconstruction type artificial knee joint of the second or third aspect further includes a detachment preventing mechanism on the inside of the lateral condyle of the femur member, the detachment preventing mechanism preventing one end of the artificial ligament from being detached from the engagement part. The detachment preventing mechanism includes: a female screw hole made in the groove formed around the engagement part; and a male screw member engaged with the female screw hole.

(Plural Anterior Cruciate Ligaments)

According to a seventh aspect, in a ligament reconstruction type artificial knee joint used in a total knee replacement, the artificial knee joint includes: a femur member mounted on a femur distal end; a tibia member mounted on a tibia proximal end; an artificial ligament coupling the tibia member and the femur member together; and a femur coupling member and a tibia coupling member, which are coupled to the artificial ligament. The femur member includes a wall-shaped lateral condyle inside wall, which is disposed on an inside of a lateral condyle of a femur when the femur member is mounted on the femur distal end, a femur fixing hole in which the femur coupling member is fixed is made at a position corresponding to a position, where once an anterior cruciate ligament exists in a knee replaced for the artificial knee joint in the lateral condyle inside wall when the femur member is mounted on the femur distal end, a tibia fixing hole in which the tibia coupling member is fixed is made at a position corresponding to a position, where once the anterior cruciate ligament exists in the knee replaced for the artificial knee joint on an upper side of the tibia member, the artificial ligament includes plural ligament members formed into a ring shape as a whole, the plural ligament members are coupled to the femur coupling member such that one end of each of the plural ligament members is disposed in a certain range including a center of a position where once the anterior cruciate ligament exists in the knee replaced for the artificial knee joint on the inside of the lateral condyle of the femur member when the femur coupling member is fixed in the femur fixing hole, the plural ligament members are coupled to the tibia coupling member such that the other end of each of the plural ligament members is disposed in a certain range including a center of a position where once the anterior cruciate ligament exists in the knee replaced for the artificial knee joint on the upper side of the tibia member when the tibia coupling member is fixed in the tibia fixing hole, and the femur coupling member and the tibia coupling member are mounted on the femur member and the tibia member respectively such that twist is generated in the plural ligament members between the femur coupling member and the tibia coupling member.

According to an eighth aspect, in the ligament reconstruction type artificial knee joint of the seventh aspect, plural ligament insertion holes are made in one end face of the femur coupling member, the plural ligament members are hooked such that one of the ligament members is inserted in a pair of ligament insertion holes in the plural ligament insertion holes, plural ligament insertion holes are made in one end face of the tibia coupling member, the plural ligament members are hooked such that one of the ligament members is inserted in a pair of ligament insertion holes in the plural ligament insertion holes.

(Posterior Cruciate Ligament)

According to a ninth aspect, the ligament reconstruction type artificial knee joint of any one of the first to eighth aspects further includes: an artificial posterior cruciate ligament connecting the tibia member and the femur member together; and a posterior cruciate ligament coupling member to which the artificial posterior cruciate ligament is coupled. The femur member includes a wall-shaped medial condyle inside wall, which is disposed on an inside of a medial condyle of the femur when the femur member is mounted on the femur distal end. In the femur member, a posterior cruciate ligament engagement part on which one end of the artificial ligament is hooked at a position corresponding to a position, where once a posterior cruciate ligament exists in the knee replaced for the artificial knee joint in the medial condyle inside wall when the femur member is mounted on the femur distal end, such that the artificial ligament pierces the medial condyle inside wall, and a notch in which the posterior cruciate ligament coupling member is disposed is provided at a position corresponding to a position, where once the posterior cruciate ligament exists in the knee replaced for the artificial knee joint in a rear portion of the tibia member.

According to a tenth aspect, in the ligament reconstruction type artificial knee joint of the ninth aspect, the posterior cruciate ligament is formed into a ring shape, a pair of through-holes is made in one end face of the posterior cruciate ligament coupling member, the artificial posterior cruciate ligament is hooked on the pair of through-holes while inserted in the pair of through-holes, a substantially V-shaped groove is formed around the posterior cruciate ligament engagement part such that a leading end of the posterior cruciate ligament engagement part is directed toward a front of the knee, the groove piercing the medial condyle inside wall, a pair of engagement holes communicating with the groove is made in a base end of the engagement part, and in the posterior cruciate ligament engagement part, a direction in which the pair of engagement holes is arrayed is provided such that twist is generated in the artificial ligament when the artificial posterior cruciate ligament is hooked on the pair of engagement holes, and when the posterior cruciate ligament coupling member is mounted in the notch of the tibia member.

According to an eleventh aspect, the ligament reconstruction type artificial knee joint of the tenth aspect further includes a detachment preventing mechanism in the medial condyle inside wall of the femur member, the detachment preventing mechanism preventing one end of the artificial posterior cruciate ligament from being detached from the engagement part. The detachment preventing mechanism includes: a female screw hole made in the groove formed around the posterior cruciate ligament engagement part; and a male screw member engaged with the female screw hole.
(Joint Shape)

According to a thirteenth aspect, in the ligament reconstruction type artificial knee joint of any one of the first to twelfth aspects, in the tibia member, an upper surface of the medial condyle is formed into a concave surface, and an upper surface of the lateral condyle is formed into a flat surface.

According to a fourteenth aspect, in the ligament reconstruction type artificial knee joint of the thirteenth aspect, the tibia member includes an intercondylar eminence between a medial condyle and a lateral condyle, and a height of the intercondylar eminence is substantially equal to a height of an intercondylar eminence in a knee replaced for the artificial knee joint.

According to a fifteenth aspect, in the ligament reconstruction type artificial knee joint of any one of the first to fourteenth aspects, the medial condyle of the tibia member is formed so as to tilt backward with respect to the lateral condyle.

According to a sixteenth aspect, in the ligament reconstruction type artificial knee joint of any one of the first to fifteenth aspects, in the tibia member, surfaces of the medial condyle and the lateral condyle tilt inward.

According to a seventeenth aspect, in the ligament reconstruction type artificial knee joint of any one of the first to sixteenth aspects, in the tibia member, peripheral portions of the medial condyle and/or the lateral condyle are formed into a curved shape.

According to an eighteenth aspect, in the ligament reconstruction type artificial knee joint of the seventeenth aspect, in the tibia member, a boundary portion between a side surface and/or a rear surface and lateral condyle is formed into an outward convex surface.

Effect of the Invention

According to the first aspect, in the femur member and the tibia member, the artificial ligament is disposed at the position where once the anterior cruciate ligament exists in the knee replaced for the artificial knee joint. The artificial ligament is formed into the ring shape, so that the artificial ligament can act similarly to the anterior cruciate ligament (healthy ligament) in the knee before being replaced for the artificial knee joint. The artificial ligament is formed into the ring shape, so that the artificial ligament can be coupled to the inside of the lateral condyle of the femur member by simply engaging one end of the artificial ligament with the engagement part. The other end of the artificial ligament can be fixed to the tibia member by simply inserting fixedly the coupling member coupled to the other end of the artificial ligament in the fixing hole of the tibia member. Accordingly, the artificial ligament is easy to mount, and a medical treatment time can be shortened. Additionally, the tensile force generated in the artificial ligament can be adjusted by a change of the state in which the coupling member is fixed to the fixing hole of the tibia member. Accordingly, the initial state of the artificial ligament can properly be adjusted according to the knee state of a patient. Additionally, the artificial ligament is formed into the ring shape, and the artificial ligament is provided such that the twist is generated in association with knee joint bending and stretching motion, so that the movement of the artificial ligament can be brought close to that of the healthy ligament in bending and stretching the knee.

According to the second aspect, the tensile force generated in the artificial ligament can be brought closer to that of the healthy ligament in bending and stretching the knee.

According to the third aspect, the artificial ligament is formed into the ring shape, and the artificial ligament is provided such that the twist is generated in association with knee joint bending and stretching motion, so that the movement of the artificial ligament can be brought close to that of the healthy ligament in bending and stretching the knee. Additionally, the tensile force generated in the artificial ligament can be brought closer to that of the healthy ligament in bending and stretching the knee.

According to the fourth aspect, the detachment preventing mechanism is provided, so that one end of the artificial ligament can stably be engaged with the engagement part. Additionally, work to fix one end of the artificial ligament to the engagement part is facilitated because only the male screw member is engaged with the female screw hole.
(Plural Anterior Cruciate Ligaments)

According to the seventh aspect, the artificial ligament is formed into the ring shape, so that the artificial ligament can act similarly to the anterior cruciate ligament (healthy ligament) in the knee before being replaced for the artificial knee joint. The femur coupling member is fixed into the femur fixing hole and the tibia coupling member is fixed to the tibia fixing hole. Therefore, the artificial ligament can be disposed at the substantially same position as the position where once the original anterior cruciate ligament exists. Accordingly, the artificial ligament is easy to mount, and a medical treatment time can be shortened. Additionally, the tensile force generated in the artificial ligament can be adjusted by a change of the state in which the femur coupling member is fixed into the femur fixing hole and/or the state in which the tibia coupling member is fixed into the fixing hole of the tibia member. Accordingly, the initial state of the artificial ligament can properly be adjusted according to the knee state of a patient. When the plural ligament members are provided, each ligament member properly generates the tensile force in bending and stretching the knee joint, so that movement of the knee replaced for artificial joint can be brought close to that of the healthy knee. Additionally, the artificial ligament is formed into the ring shape, and the artificial ligament is provided such that the twist is generated in association with knee joint bending and stretching motion, so that the movement of the artificial ligament can be brought close to that of the healthy ligament in bending and stretching the knee.

According to the eighth aspect, the tensile force generated in the artificial ligament can be brought closer to that of the healthy ligament in bending and stretching the knee.

(Posterior Cruciate Ligament)

According to the ninth aspect, in the femur member and the tibia member, the artificial posterior cruciate ligament is disposed at the position where once the posterior cruciate ligament exists in the knee replaced for the artificial knee joint, so that the artificial posterior cruciate ligament can act like the posterior cruciate ligament (healthy ligament) in the knee before being replaced for the artificial knee joint. Additionally, a relatively positional relationship between the artificial posterior cruciate ligament and the anterior cruciate ligament (artificial ligament) and the movement of the artificial ligament can be brought close to those of the healthy knee. Accordingly, the knee replaced for the artificial joint can be brought close to the healthy knee. The artificial posterior cruciate ligament can be coupled to the inside of the medial condyle of the femur member by simply engaging one end of the artificial posterior cruciate ligament to the posterior cruciate ligament engagement part. Additionally, the other end of artificial ligament can be fixed to the tibia member by simply disposing fixedly the fixing member mounted on the other end of the artificial posterior cruciate ligament in the notch of the tibia member. Accordingly, the artificial posterior cruciate ligament is easy to mount, and the medical treatment time can be shortened. Additionally, the tensile force generated in the artificial posterior cruciate ligament can be adjusted by a change of the state in which the fixing member is disposed in the notch of the tibia member. Accordingly, the initial state of the artificial posterior cruciate ligament can properly be adjusted according to the knee state of a patient.

According to the tenth aspect, the artificial posterior cruciate ligament is formed into the ring shape, and the artificial posterior cruciate ligament is provided such that the twist is generated in association with the knee joint bending and stretching motion, so that the movement of the artificial posterior cruciate ligament can be brought close to that of the healthy posterior cruciate ligament in bending and stretching the knee. Additionally, the tensile force generated in the artificial posterior cruciate ligament can be brought closer to that of the healthy ligament in bending and stretching the knee.

According to the eleventh aspect, the detachment preventing mechanism is provided, so that one end of the artificial posterior cruciate ligament can stably be engaged with the engagement part. Additionally, work to fix one end of the artificial posterior cruciate ligament to the engagement part is facilitated because only the male screw member is engaged with the female screw hole.

(Joint Shape)

According to the thirteenth aspect, the artificial ligament and/or artificial posterior cruciate ligament is provided at the substantially same position of the anterior cruciate ligament and/or posterior cruciate ligament in the healthy state, and the medial condyle and the lateral condyle become states close to a shape of the tibia of a living body, so that the movement of the artificial knee joint can be brought closer to natural movement.

According to the fourteenth aspect, in bending and stretching the knee, the artificial anterior cruciate ligament and the intercondylar eminence interfere with each other by providing the intercondylar eminence. The interference enables the artificial anterior cruciate ligament to generate the relaxation and tension states similar to those of the anterior cruciate ligament in the knee before being replaced for the artificial knee joint. Additionally, the femur and the tibia can be prevented from skidding by the intercondylar eminence. Accordingly, movement of the knee replaced for the artificial knee joint can be brought into the state closer to the original knee before being replaced for the artificial knee joint.

According to the fifteenth and sixteenth aspects, the shape of the tibia member is close to that of the tibia proximal end, so that the movement of the artificial knee joint can be brought closer to the natural movement.

According to the seventeenth aspect, even if the medial condyles of the femur member and the tibia member and/or the lateral condyles of the femur and the tibia member move relatively, a large load can be prevented from being applied to surrounding portions of the medial condyle and/or the lateral condyle of the tibia member. That is, edge loading can be reduced, and therefore the damage of the femur member and tibia member can be prevented.

According to the eighteenth aspect, the edge in the rear portion of the lateral condyle has a gently curved surface, so that deeply bending motion such as straight sitting is permitted while the edge loading is reduced. Therefore, damage of the femur member or tibia member can be prevented. Additionally, a movable range of the knee can be widened after the replacement for the artificial knee joint.

BRIEF DESCRIPTION OF THE DRAWINGS

FIG. 41(A) illustrates a state in which a knee is stretched, and FIG. 41(B) illustrates a state in which the knee is bent.

FIG. 42(A) illustrates the state in which the knee is stretched, and FIG. 42(B) illustrates the state in which the knee is bent.

FIG. 43(A) illustrates the state in which the knee is stretched, and FIG. 43(B) illustrates the state in which the knee is bent.

FIG. 44(A) illustrates the state in which the knee is stretched, and FIG. 44(B) illustrates the state in which the knee is bent.

FIG. 45(A) illustrates the state in which the knee is stretched, and FIG. 45(B) illustrates the state in which the knee is bent.

FIG. 64(A) is a view illustrating a simulation result of the state in which the knee is bend by 112 degrees, and FIG. 64(B) is a view illustrating a simulation result of the state in which the knee is bend by 121 degrees.

MODES FOR CARRYING OUT THE INVENTION

A ligament reconstruction type artificial knee joint of the present invention is used in a total knee replacement in the treatment of the knee osteoarthritis, the joint rheumatism, or the like, and has a feature that provides a function of the anterior cruciate ligament.

(Ligament Reconstruction Type Artificial Knee Joint 1 of Embodiment)

As illustrated in FIGS. 1 to 4, a ligament reconstruction type artificial knee joint 1 of an embodiment (hereinafter, simply referred to as an artificial knee joint 1 of the embodiment) includes a femur member 10, a tibia member 20, and an artificial ligament 30 acting as an anterior cruciate ligament.

In FIGS. 1 to 4, the artificial knee joint 1 for a right knee is described as a representative. For clarification of a structure, a posterior cruciate ligament PCL, a femur F, and a tibia T are omitted in FIGS. 1 to 4.

(Femur Member 10)

Figure 5:
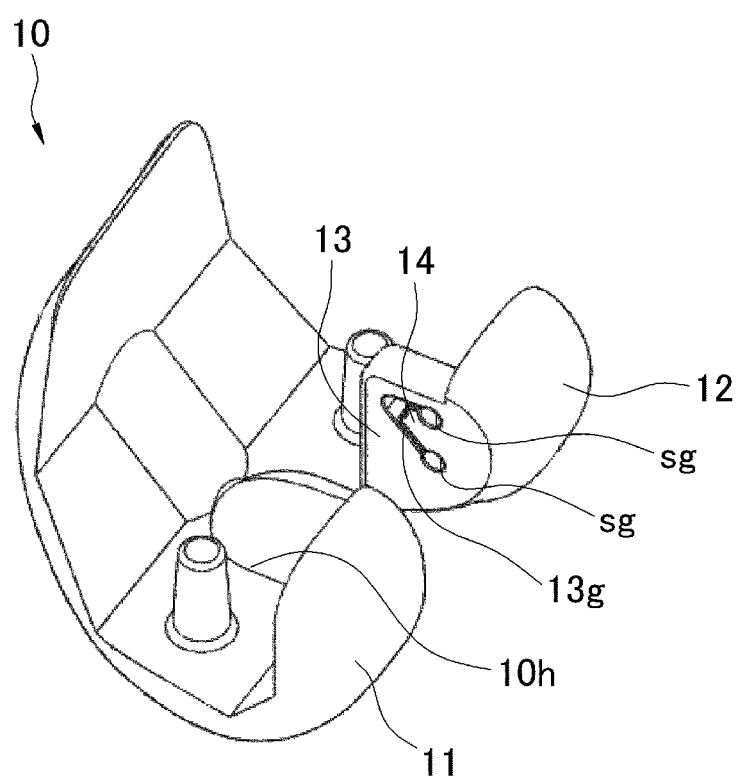
FIG. 5 is a perspective view schematically illustrating a femur member 10 of the ligament reconstruction type artificial knee joint 1 of the embodiment.
Figure 6:
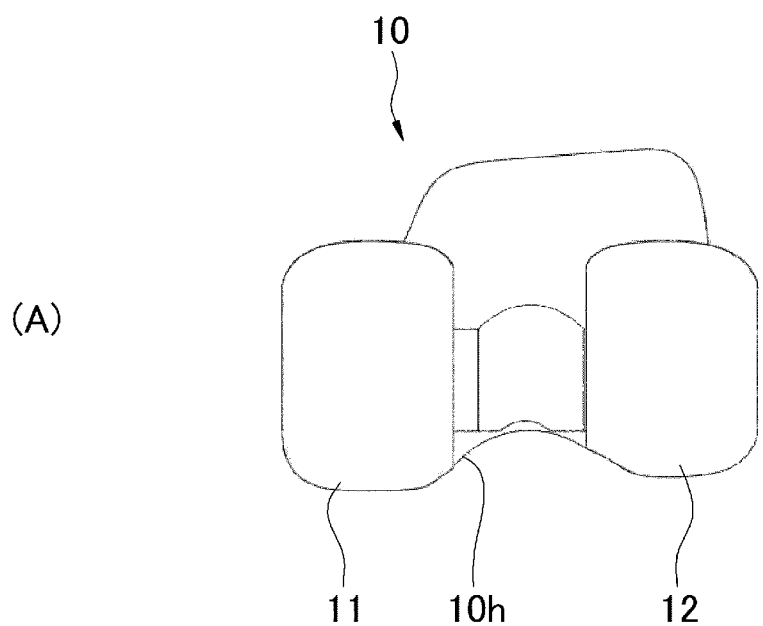
FIGS. 6(A) and 6(B) are rear and front views schematically illustrating the femur member 10 of the ligament reconstruction type artificial knee joint 1 of the embodiment, respectively.
Figure 6:
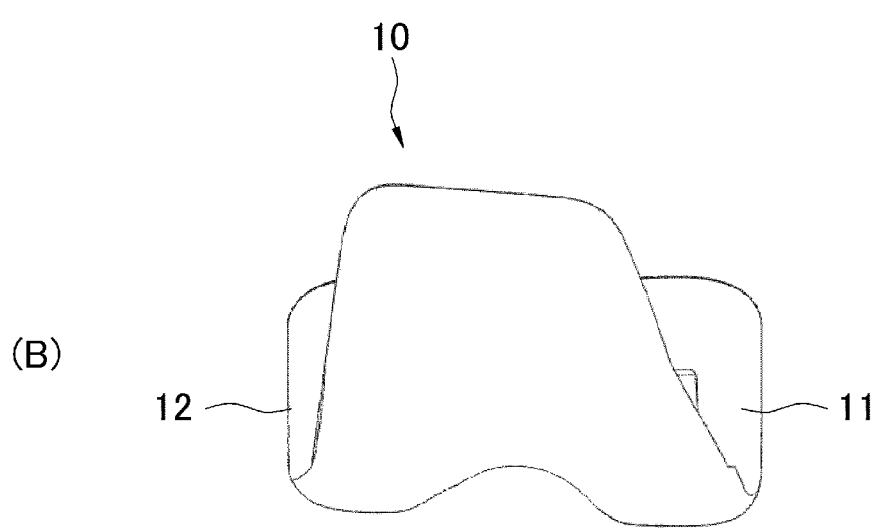
Figure 7:
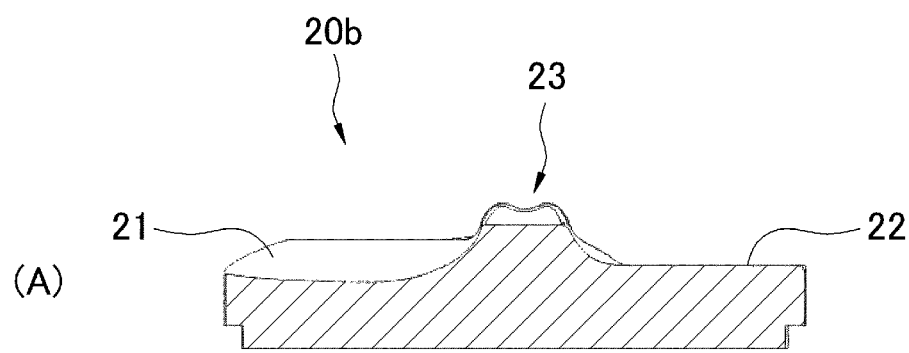
FIG. 7(A) is a sectional view taken along a line VIIA-VIIA in FIG. 8.
FIG. 7(B) is a perspective view schematically illustrating a contact part 20b in a tibia member 20 of the ligament reconstruction type artificial knee joint 1 of the embodiment.
Figure 7:
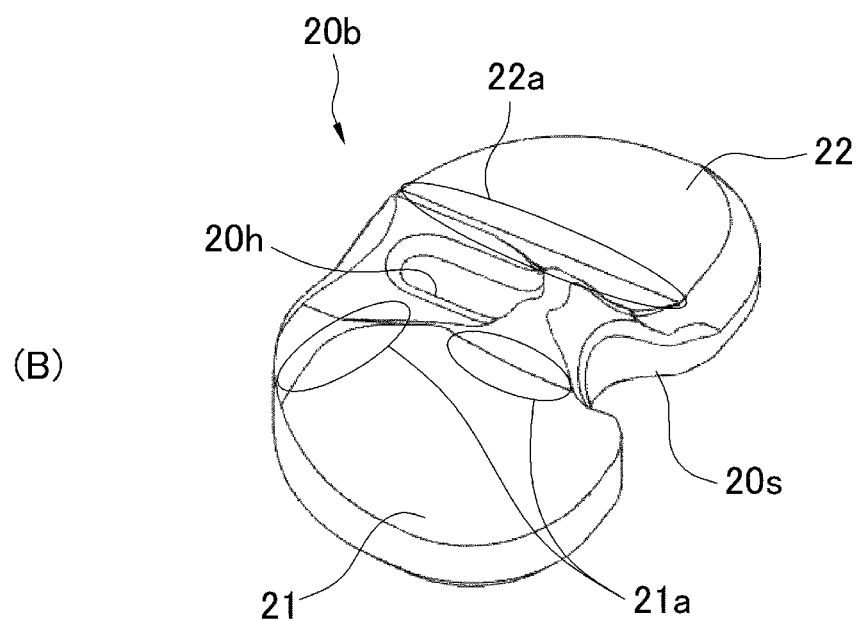
Figure 8:
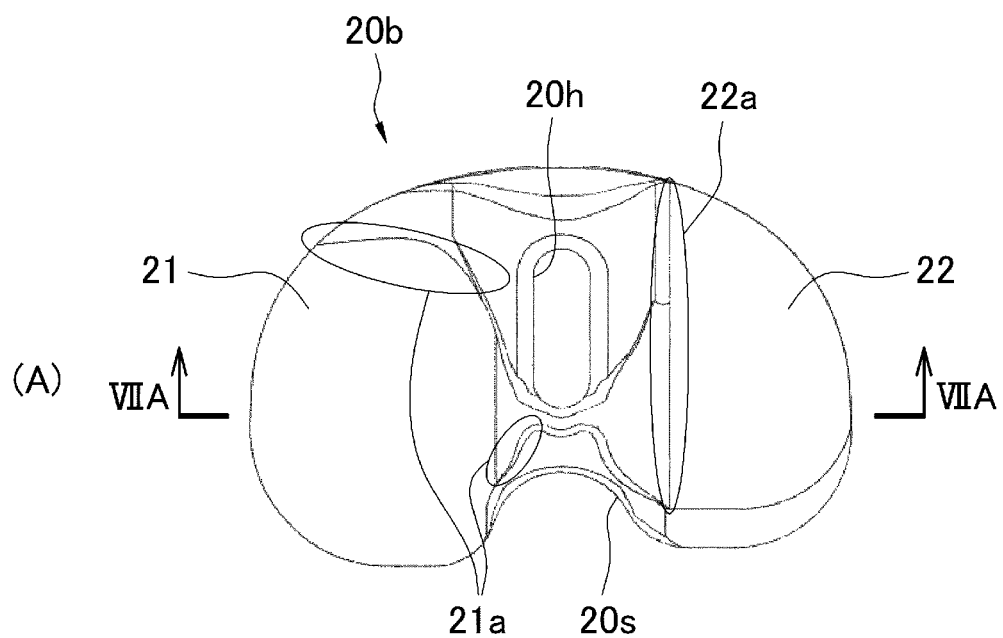
FIGS. 8(A) and 8(B) are plan and bottom views schematically illustrating the contact part 20b in the tibia member 20 of the ligament reconstruction type artificial knee joint 1 of the embodiment, respectively.
Figure 8:
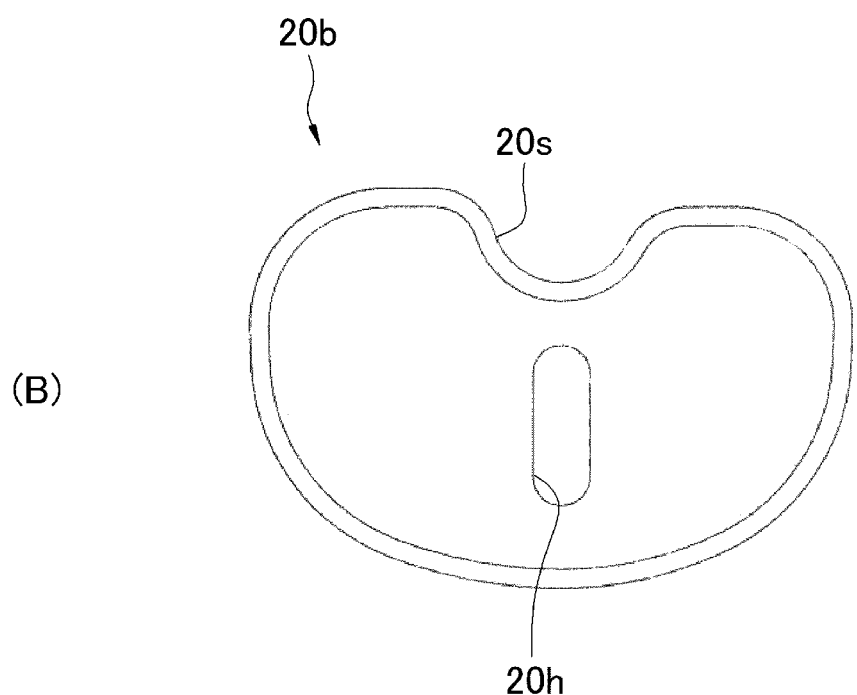

The femur member 10 is mounted on a distal end DT of the femur F. The femur member 10 includes a part (hereinafter, simply referred to as a medial condyle 11) mounted on a medial condyle MC of the femur F and a part (hereinafter, simply referred to as a lateral condyle 12) mounted on a lateral condyle LC of the femur F. Specifically, each of the medial condyle 11 and the lateral condyle 12 is formed into a substantial J-shape, namely, an arc shape inside view. In the femur member 10, a gap 10h is formed between the medial condyle 11 and the lateral condyle 12. That is, in the femur member 10, surfaces of the medial condyle 11 and lateral condyle 12 are formed into the substantially same shape as the distal end DT of the normal femur F of a human body, the surfaces coming into contact with the tibia member 20 (see FIGS. 5 and 6).

A wall-like portion (hereinafter, simply referred to as a lateral condyle inside wall 13) is provided inside the lateral condyle 12 of the femur member 10 (that is, on the side of the medial condyle 11 of the lateral condyle 12). An engagement part 14 is provided in the lateral condyle inside wall 13 of the femur member 10. The engagement part 14 is formed so as to be disposed near a position where an original anterior cruciate ligament ACL and the distal end DT of the original femur F are coupled together when the femur member 10 is mounted at the distal end DT of the femur F.

Specifically, a groove 13g is provided in the lateral condyle inside wall 13 so as to pierce the lateral condyle inside wall 13. The groove 13g is formed such that a width of the groove 13g is thinner than a normal diameter of the artificial ligament 30 (that is, a diameter in a state in which the tensile force is not substantially applied to the artificial ligament 30). The groove 13g is formed into a substantial V-shape, and the substantially triangular engagement part 14 is formed in the lateral condyle inside wall 13 by the groove 13g. The groove 13g is formed such that a leading end of the engagement part 14 is directed forward.

A pair of engagement holes sg, sg vertically separated from each other is made at a base end (that is, both ends of the groove 13g) of the engagement part 14. The pair of engagement holes sg, sg is made such that a diameter of the pair of engagement holes sg, sg is substantially equal to the normal diameter of the artificial ligament 30 (that is, the diameter in the state in which the tensile force is not substantially applied to the artificial ligament 30). When the pair of engagement holes sg, sg is made, the artificial ligament 30 can be coupled to the engagement part 14 in the state in which the artificial ligament 30 is properly positioned.

Desirably a boundary portion between the pair of engagement holes sg, sg and a rear surface of the engagement part 14 is formed into a curved shape. In this case, damage of the artificial ligament 30 can be suppressed compared with the case that the boundary portion is formed into an edge shape.

There is no particular limitation to a shape or a size of the pair of engagement holes sg, sg and a position where the pair of engagement holes sg, sg is provided, and a positional relationship between the engagement holes sg, sg as long as the artificial ligament 30 is engaged. In the case that a groove bg is provided (to be described later), the artificial ligament 30 can be firmly coupled to the engagement part 14 even if the engagement hole sg is not necessarily made. In the case that the pair of engagement holes sg, sg is not made, desirably the groove 13g is formed such that the width of the groove 13g is substantially equal to the normal diameter of the artificial ligament 30.

Figure 24:
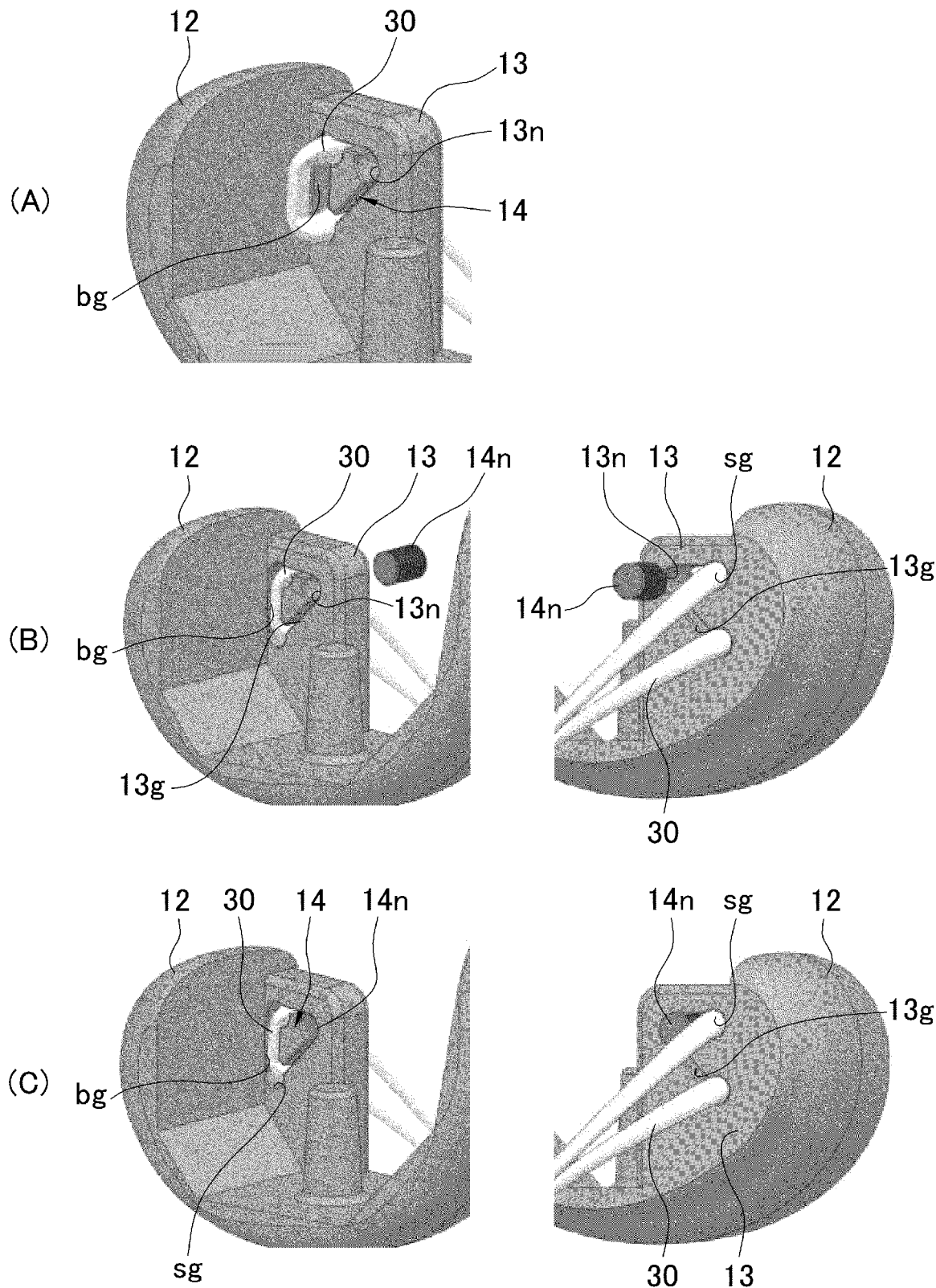
FIG. 24 is a view schematically illustrating a status in which one end 30 of the artificial ligament is engaged with an engagement part 14 of the femur member 10 in the ligament reconstruction type artificial knee joint 1 of the embodiment.

As illustrated in FIG. 24, desirably a groove bg is formed in a rear surface (that is, a surface contacting with an inner surface of the lateral condyle 12) of the lateral condyle inside wall 13. Specifically, desirably the groove bg is formed so as to connect the pair of engagement holes sg, sg to each other. In this case, the groove bg is formed such that the width and depth of the groove bg are slightly longer than a shaft diameter of the artificial ligament 30. When one end of the artificial ligament 30 is hooked on the pair of engagement holes sg, sg, the artificial ligament 30 is perfectly accommodated in the groove bg, and the artificial ligament 30 does not protrude from the rear surface of the lateral condyle inside wall 13. Accordingly, when the groove bg is provided, the artificial ligament 30 and the inner surface of the lateral condyle 12 contact with each other to prevent the damage of the artificial ligament 30. Alternatively, the pair of engagement holes sg, sg is not made, but the groove bg may be provided. Even in this case, the artificial ligament 30 can be coupled to the engagement part 14 while positioned by the groove bg. As described above, desirably the groove 13g is formed such that the width of the groove 13g is substantially equal to the normal diameter of the artificial ligament 30. Of course, in the case that the groove bg is provided together with the pair of engagement holes sg, sg, the artificial ligament 30 can be positioned in the more stable state.

Desirably the boundary portion between the pair of engagement holes sg, sg and the groove bg is formed into the curved shape. In this case, the damage of the artificial ligament 30 can be suppressed compared with the case that the boundary portion is formed into an edge shape.

The groove bg is not necessarily provided, as long as the artificial ligament 30 can be disposed so as not to contact with the inner surface of the lateral condyle 12 when one end of the artificial ligament 30 is hooked on the pair of engagement holes sg, sg.

It is not necessary that the width and depth of the groove bg be kept constant between both ends of the groove bg (that is, between the pair of engagement holes sg, sg), but the width and depth of the groove bg may be change depending on the position. For example, the depth of the groove may increase at both the end of the groove bg, and decrease in the middle between both the end. That is, the bottom of the groove may be formed into a ridge-like curved surface having a vertex in a middle portion. In this case, the damage of the artificial ligament 30 due to interference with the inside of the groove bg can be suppressed.

When the pair of engagement holes sg, sg or the groove bg is provided as described above, the artificial ligament 30 is accommodated in the pair of engagement holes sg, sg or the groove bg, so that the artificial ligament 30 can be prevented from being detached from the engagement part 14. That is, when one of or both the pair of engagement holes sg, sg and the groove bg are provided, the pair of engagement holes sg, sg or the groove bg can act as a detachment preventing mechanism.

Desirably a mechanism (detachment preventing mechanism) that prevents the artificial ligament 30 from being detached from the engagement part 14 is provided in the groove 13g in addition to the pair of engagement holes sg, sg and the groove bg. For example, a female screw hole 13n is made between both the ends (a portion, such as the leading end of the engagement part 14, which is located between the pair of engagement holes sg, sg in FIG. 24) of the groove 13g. A male screw member 14n (for example, a set screw in which a male screw is formed in an outer surface) that can be engaged with the female screw hole 13n is provided. In this case, when the male screw member 14n is engaged with the female screw hole 13n, the groove 13g can be separated into two holes by the male screw member 14n. The male screw member 14n is engaged with the female screw hole 13n while one end of the artificial ligament 30 is disposed so as to pass through the position where one hole in the groove 13g is made from the front surface of the lateral condyle inside wall 13 toward the rear surface, and so as to return from the rear surface of the lateral condyle inside wall 13 to the front surface through the position where the other hole in the groove 13g is made. Therefore, one end of the artificial ligament 30 can be prevented from being detached from the engagement part 14. That is, the detachment preventing mechanism can be constructed with the female screw hole 13n and the male screw member 14n.

In the configuration constructed with the female screw hole 13n and the male screw member 14n, there is no particular limitation to the shape and size of the male screw member 14n. However, desirably the male screw member 14n is the set screw, and a length in an axial direction of the male screw member 14n is substantially equal to the thickness of the engagement part 14. The use of the set screw can prevent the male screw member 14n from interfering with a peripheral member or a bone even if the male screw member 14n is mounted on the engagement part 14.

The detachment preventing mechanism is not limited to the configuration constructed with the female screw hole 13n and the male screw member 14n as long as the groove 13g can be separated into the two holes. For example, a rubber member may be pushed in the groove 13g to separate the groove 13g into the two holes.

(Tibia Member 20)

The tibia member 20 is mounted on a proximal end PE of a tibia E. The tibia member 20 is formed by a combination of a base part 20a and a contact part 20b.

Figure 12:
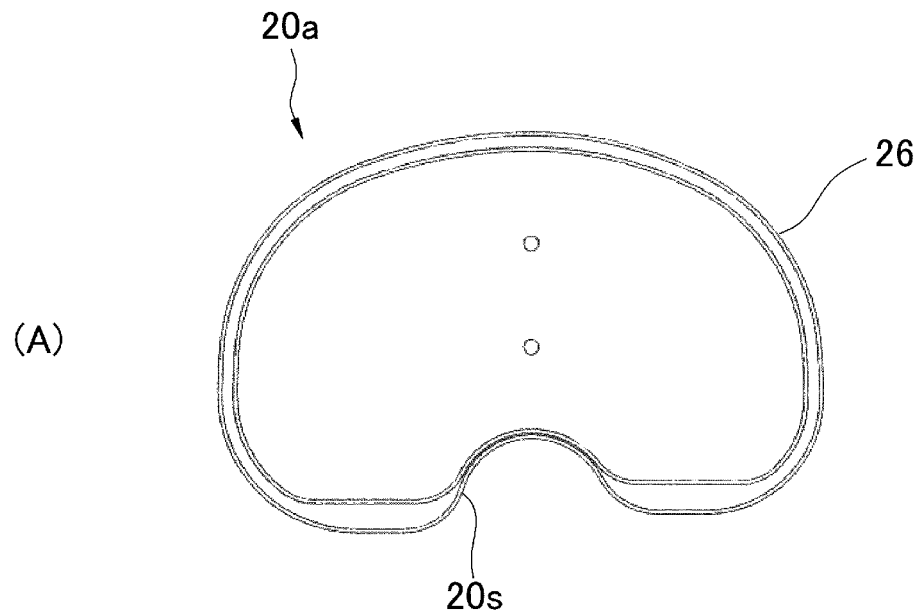
FIGS. 12(A) and 12(B) are plan and bottom views schematically illustrating the base part 20a in the tibia member 20 of the ligament reconstruction type artificial knee joint 1 of the embodiment, respectively.
Figure 12:
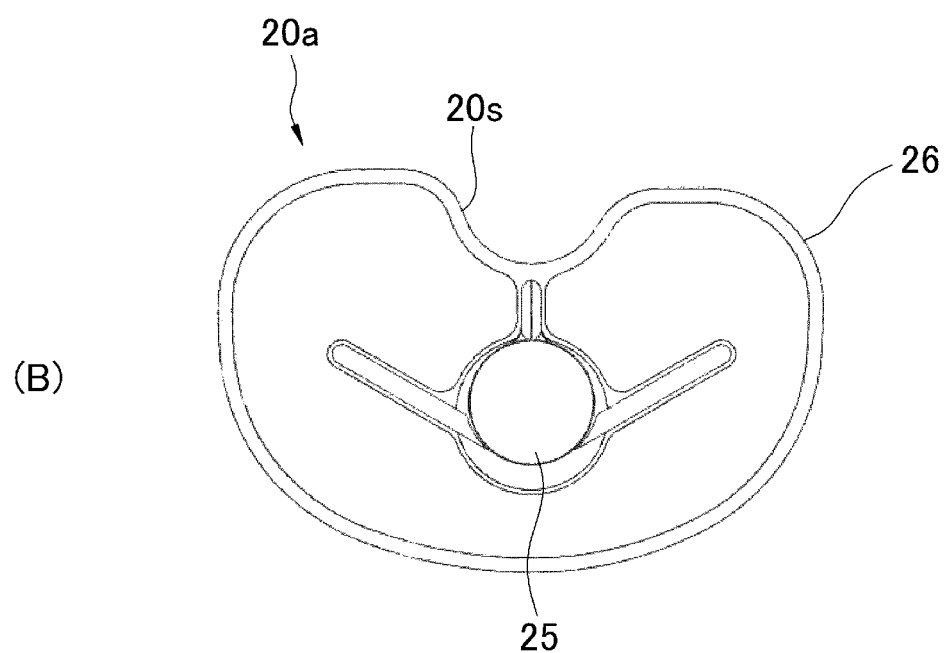
Figure 13:
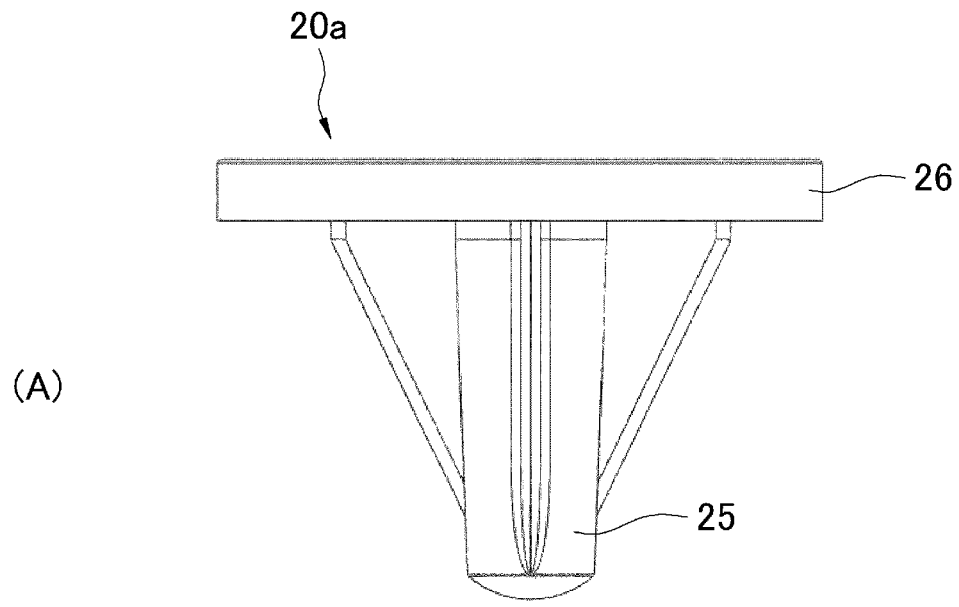
FIGS. 13(A) and 13(B) are rear and front views schematically illustrating the base part 20a in the tibia member 20 of the ligament reconstruction type artificial knee joint 1 of the embodiment, respectively.
Figure 13:
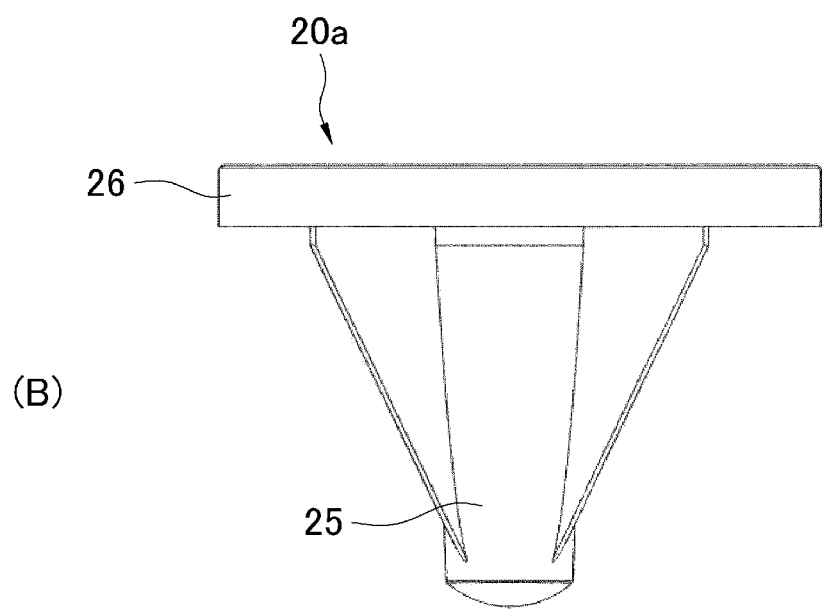

The base part 20a (see FIGS. 11 to 13) is fixed to the tibia E of the tibia member 20, and includes a plate-like base plate 26 and a rod-shaped stem 25 of which an upper end is coupled to the bottom surface of base plate 26. The stem 25 is inserted in a hole made at the proximal end PE of the tibia E.

The contact part 20b is mounted on a top surface of the base plate 26 of the base part 20. The contact part 20b includes a portion corresponding to the medial condyle MC of the tibia E (hereinafter, simply referred to as a medial condyle 21) and a portion corresponding to the lateral condyle LC of the tibia E (hereinafter, simply referred to as a lateral condyle 22) in the top surface of the contact part 20b (see FIGS. 7 to 10).

In a rear portion of the tibia member 20, a notch 20s is continuously formed from the bottom surface of the base plate 26 to the top surface of the contact part 20b between the medial condyle 21 and lateral condyle 22 of the contact part 20b. Specifically, the notch 20s is formed such that the posterior cruciate ligament PCL can be disposed at a position where the original posterior cruciate ligament PCL exists when the tibia member 20 is fixed to the proximal end PE of the tibia E (see FIGS. 7 and 12).

In the contact part 20b of the tibia member 20, a fixing hole 20h is made between the medial condyle 21 and lateral condyle 22, which are located in a front portion of the contact part 20b. Specifically, the fixing hole 20h is made such that an opening is located near the position where the original anterior cruciate ligament ACL and the original tibia E are coupled together when the tibia member 20 is mounted on the proximal end PE of the tibia E. The fixing hole 20h is made such that the section of the fixing hole 20h is formed into a long hole shape (substantial racetrack shape). The fixing hole 20h is made such that a long axis direction of the fixing hole 20h is substantially parallel to the lateral condyle inside wall 13 when the knee is stretched (see FIG. 1(B)).

In the top surface of the contact part 20b, an intercondylar eminence 23 is formed between the medial condyle 21 and the lateral condyle 22 and between the fixing hole 20h and the notch 20s (see FIGS. 7 to 10).

That is, the upper portion of the tibia member 20 is formed into the shape similar to the proximal end PE of the normal tibia T of the human body.

(Artificial Ligament 30)

Figure 1:
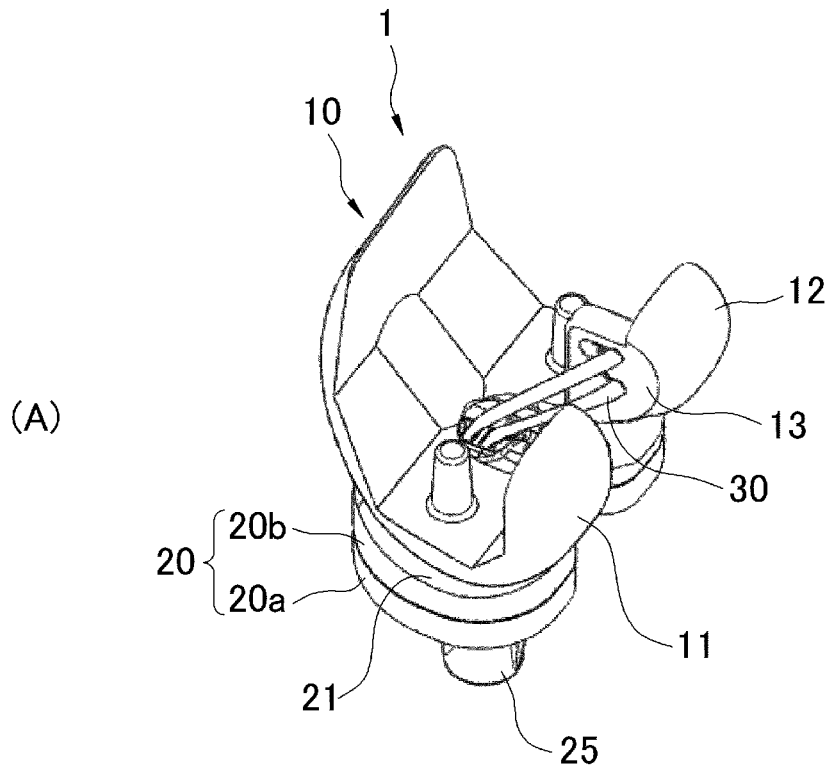
FIGS. 1(A) and 1(B) are perspective and sectional views schematically illustrating a ligament reconstruction type artificial knee joint 1 according to an embodiment, respectively.
Figure 1:
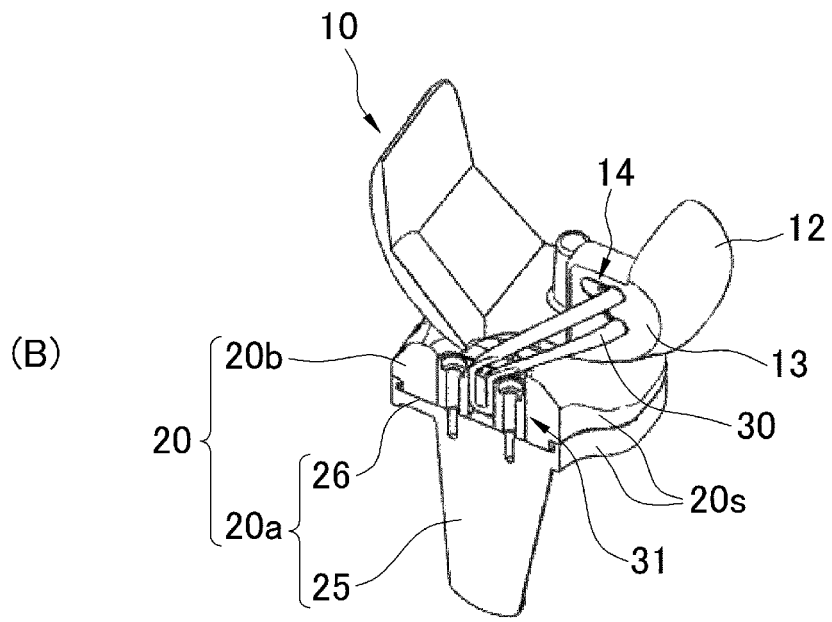
Figure 2:
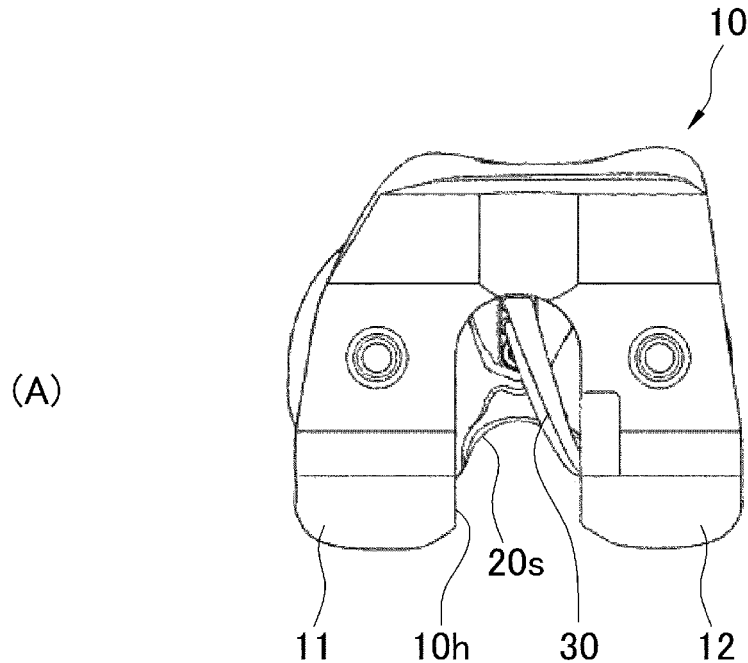
FIGS. 2(A) and 2(B) are plan and bottom views schematically illustrating the ligament reconstruction type artificial knee joint 1 of the embodiment, respectively.
Figure 2:
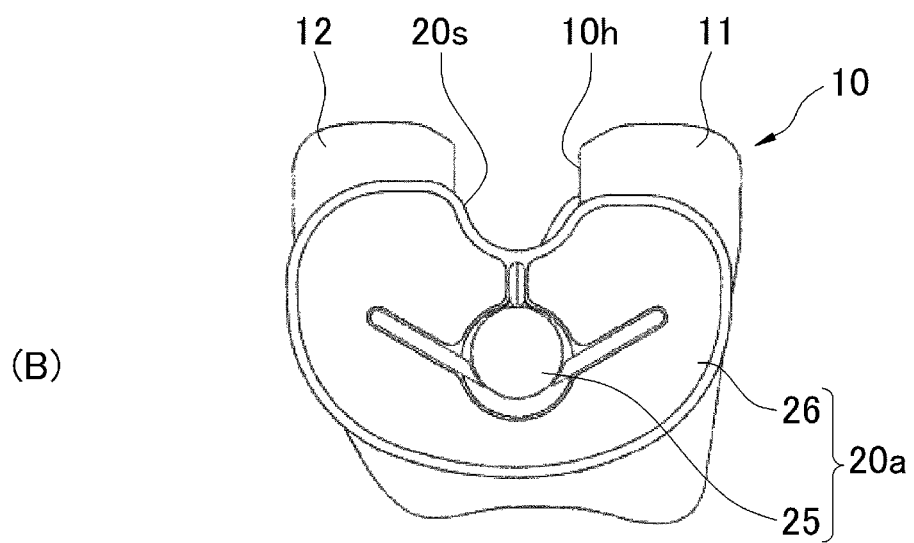
Figure 3:
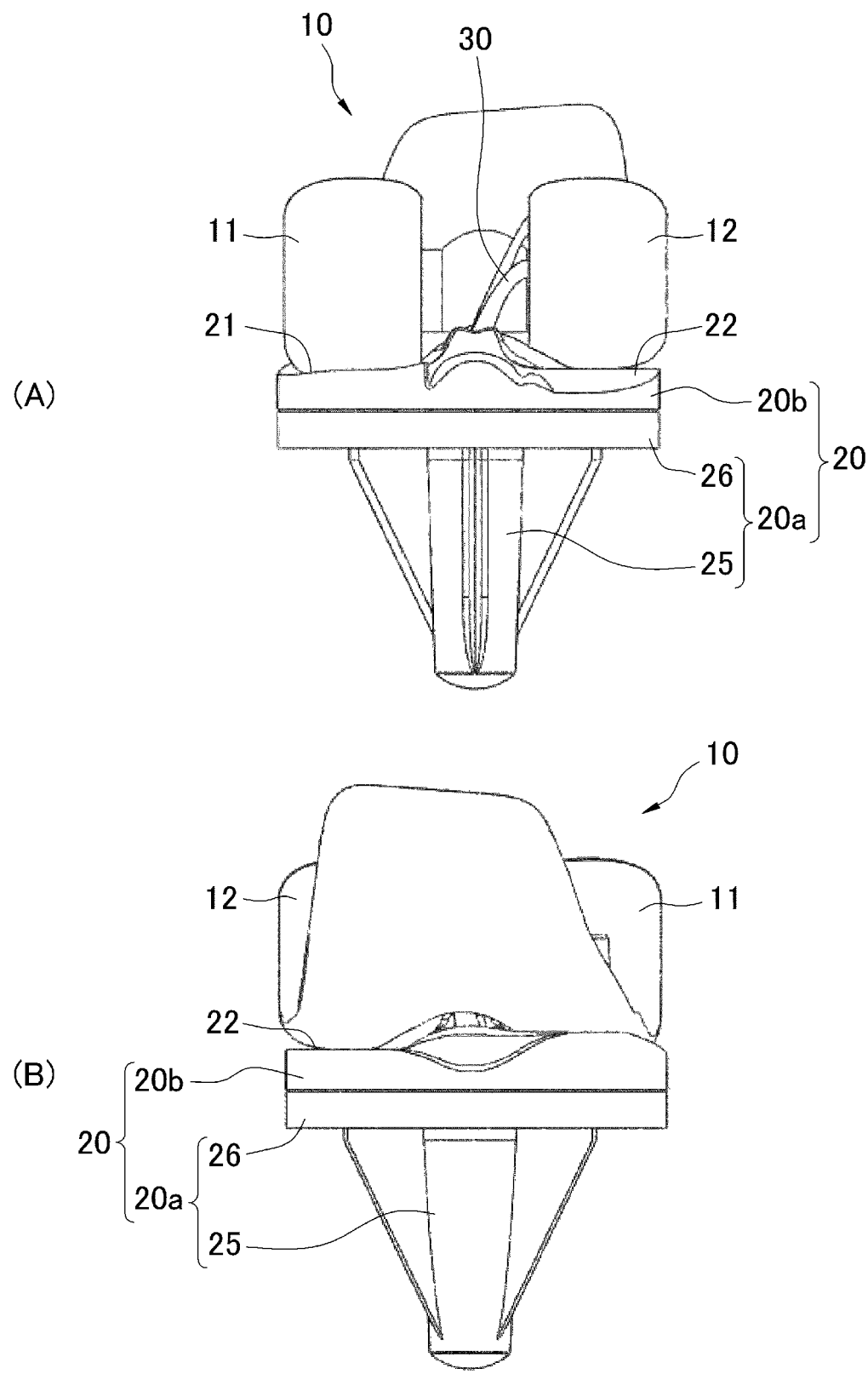
FIGS. 3(A) and 3(B) are rear and front views schematically illustrating the ligament reconstruction type artificial knee joint 1 of the embodiment, respectively.
Figure 4:
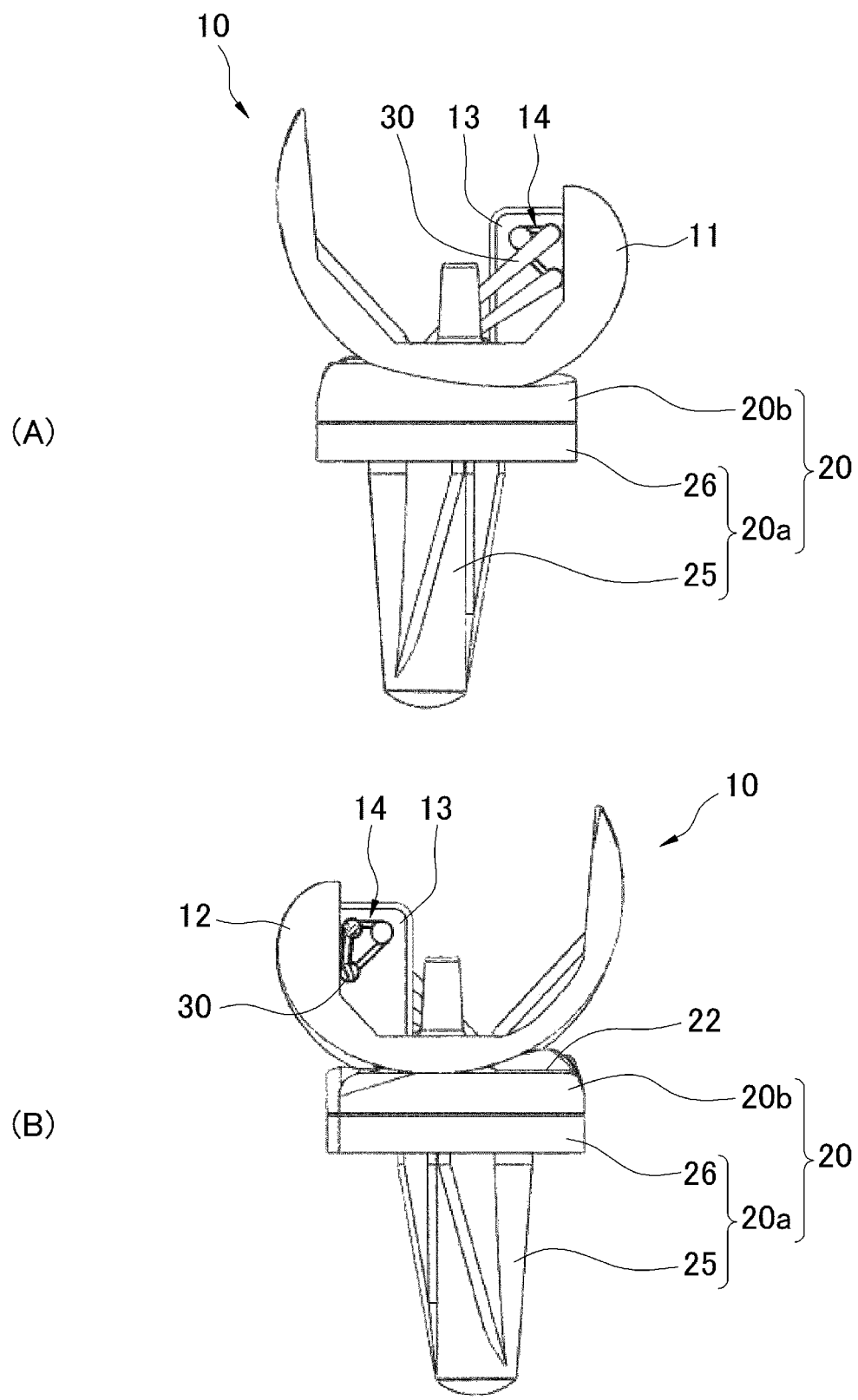
FIGS. 4(A) and 4(B) are right and left side views schematically illustrating the ligament reconstruction type artificial knee joint 1 of the embodiment, respectively.

As illustrated in FIGS. 1 and 2, the artificial ligament 30 is provided between the lateral condyle inside wall 13 of the femur member 10 and the contact part 20b of the tibia member 20. The artificial ligament 30 is a string-shaped member that is artificially made from a material such as polyester. The artificial ligament 30 is formed into a ring shape.

One end of the artificial ligament 30 is engaged with the engagement part 14 formed in the lateral condyle inside wall 13 of the femur member 10. Specifically, the artificial ligament 30 is hooked on the engagement part 14 so as to be disposed at the positions of the pair of engagement holes sg, sg of the groove 13g.

Figure 14:
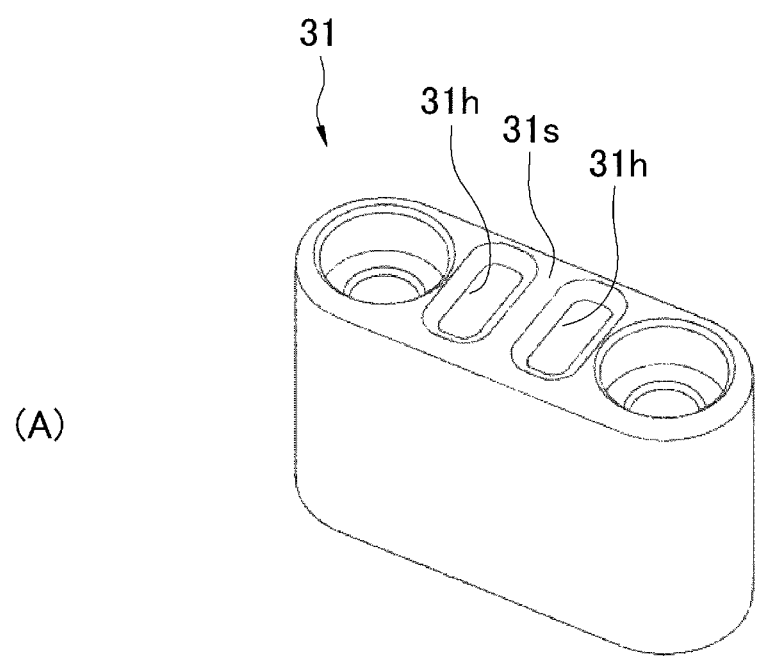
FIGS. 14(A) and 14(B) are perspective and longitudinally sectional views schematically illustrating a coupling member 31, respectively.
Figure 14:
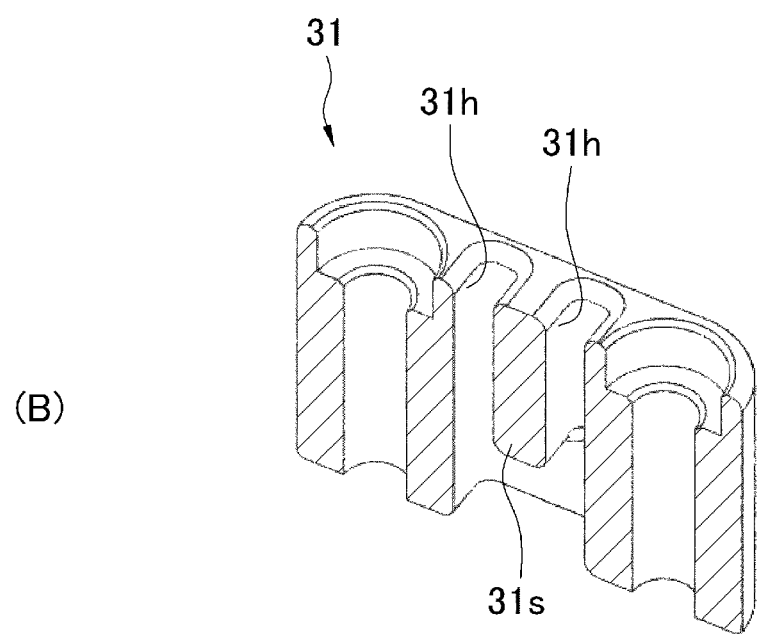
Figure 15:
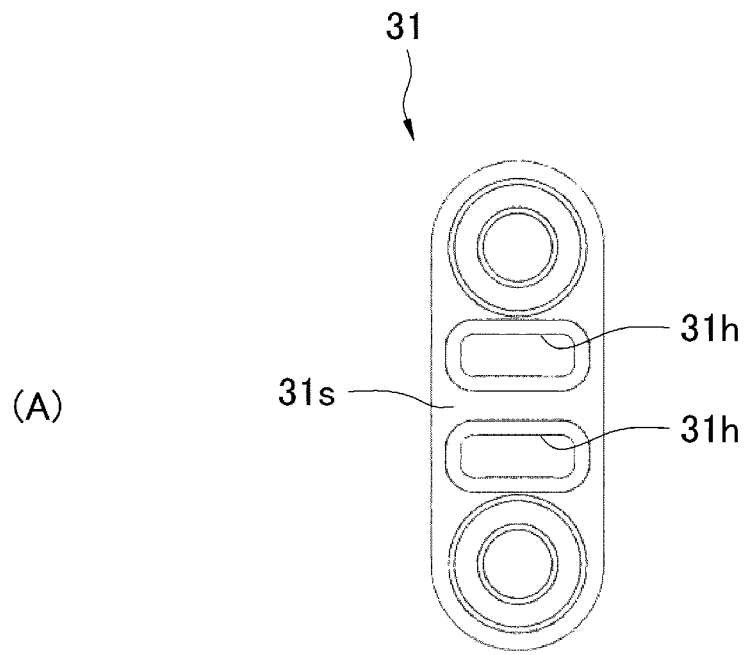
FIGS. 15(A) and 15(B) are plan and bottom views schematically illustrating the coupling member 31, respectively.
Figure 15:
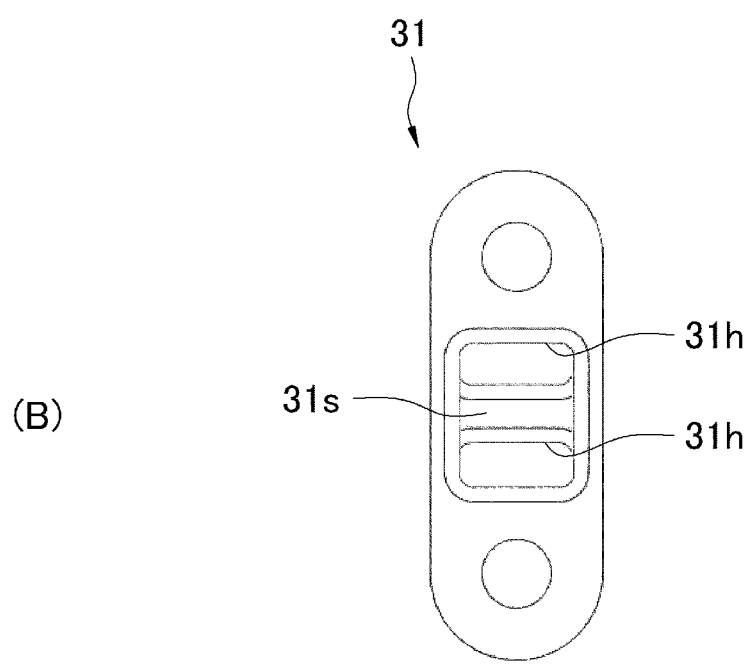
Figure 16:
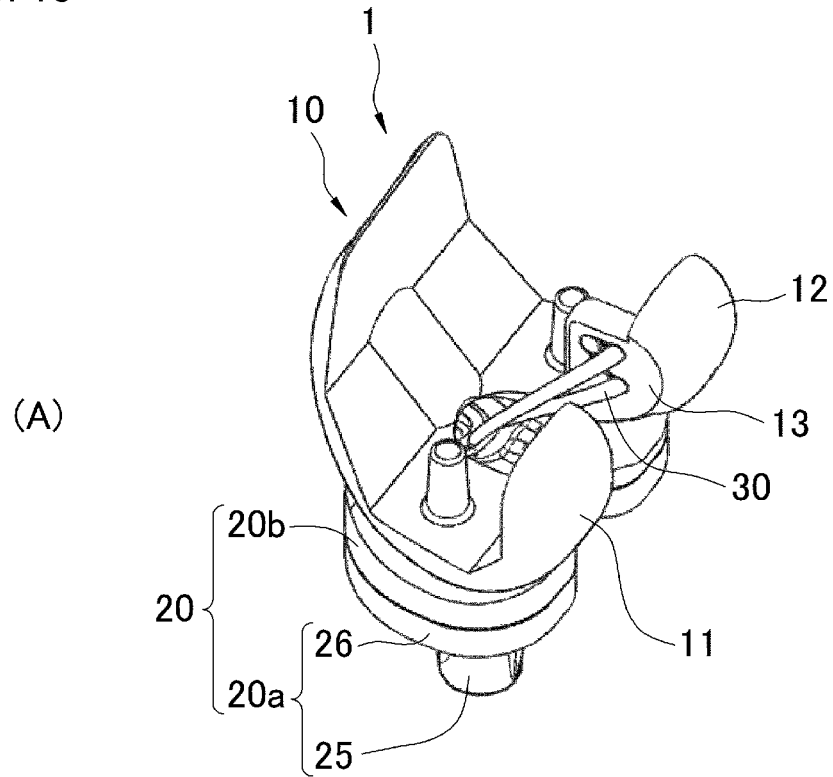
FIGS. 16(A) and 16(B) are perspective and sectional views schematically illustrating a ligament reconstruction type artificial knee joint 1 according to another embodiment, respectively.
Figure 16:
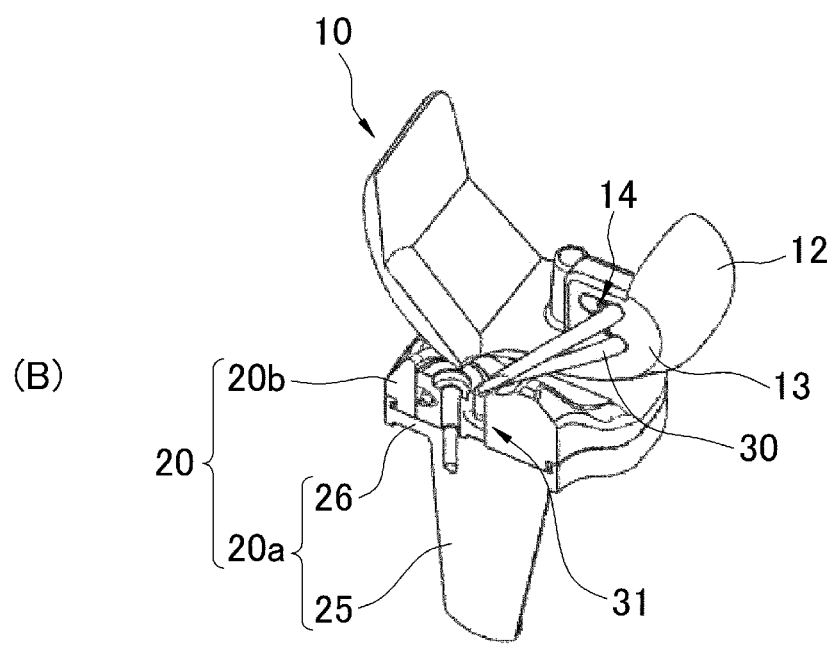
Figure 17:
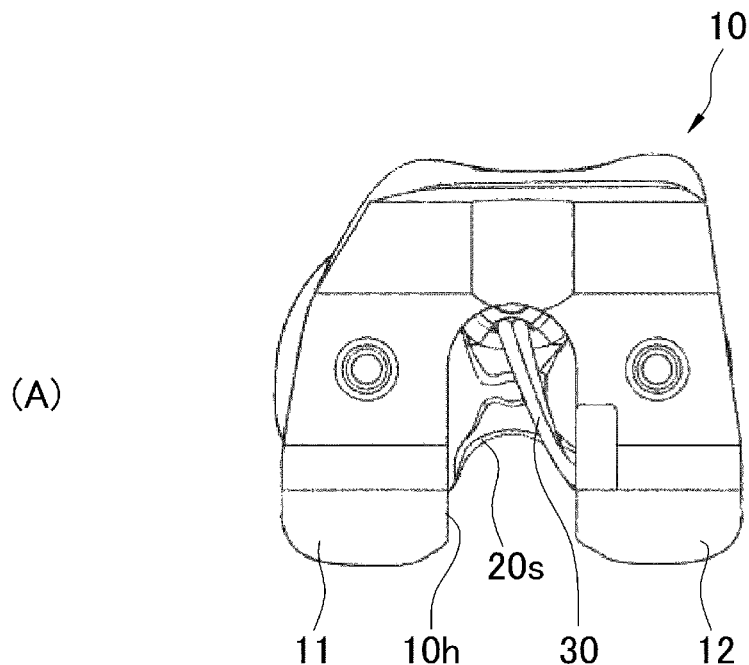
FIGS. 17(A) and 17(B) are plan and bottom views schematically illustrating the ligament reconstruction type artificial knee joint 1 of another embodiment, respectively.
Figure 17:
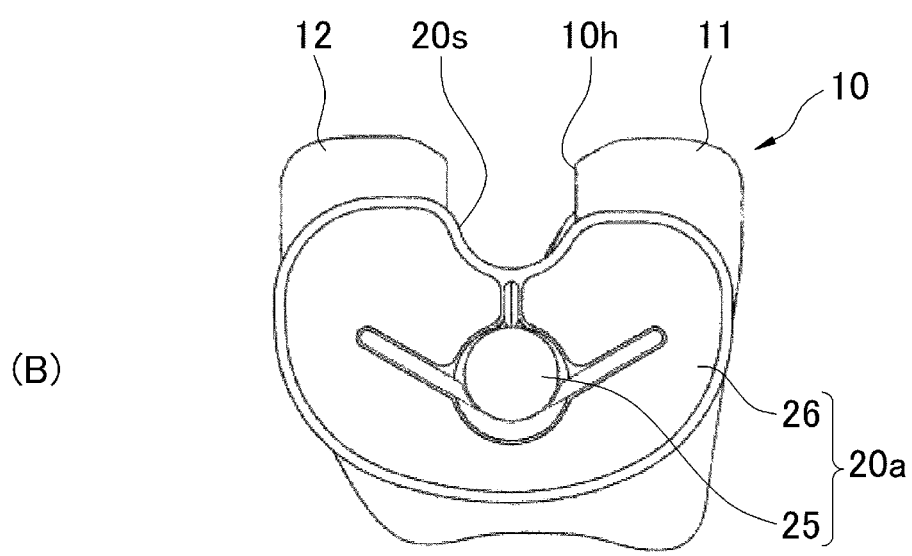
Figure 18:
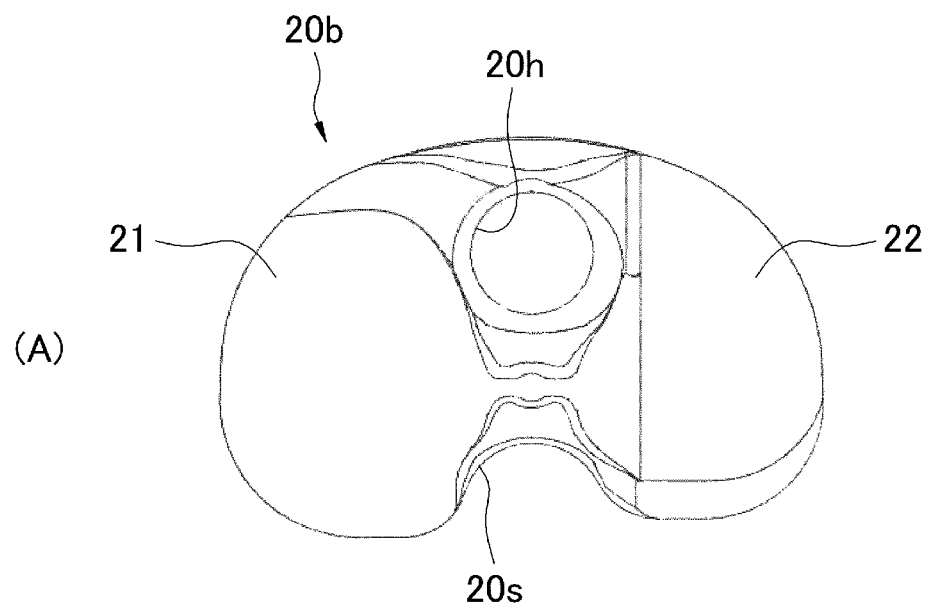
FIGS. 18(A) and 18(B) are plan and bottom views schematically illustrating a contact part 20b in a tibia member 20 of the ligament reconstruction type artificial knee joint 1 of another embodiment, respectively.
Figure 18:
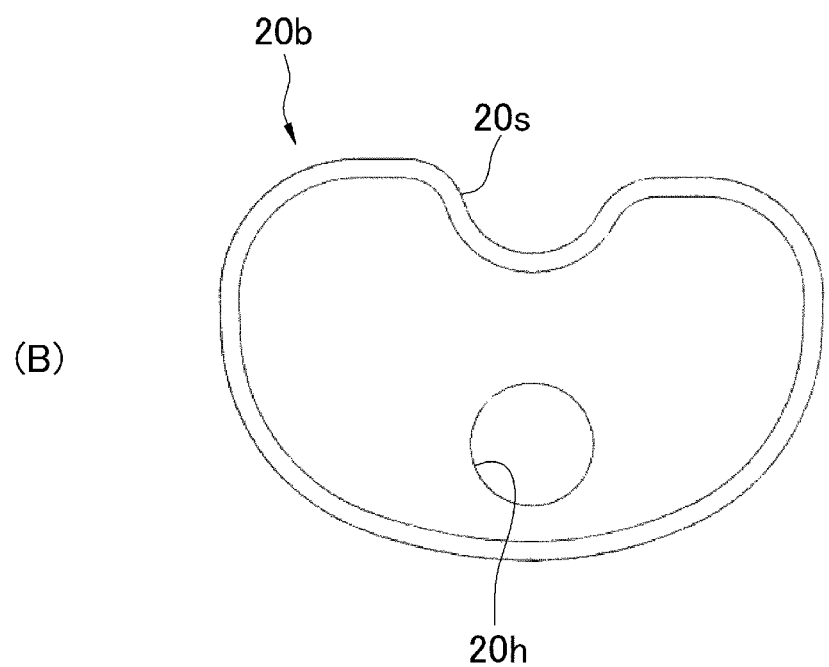
Figure 19:
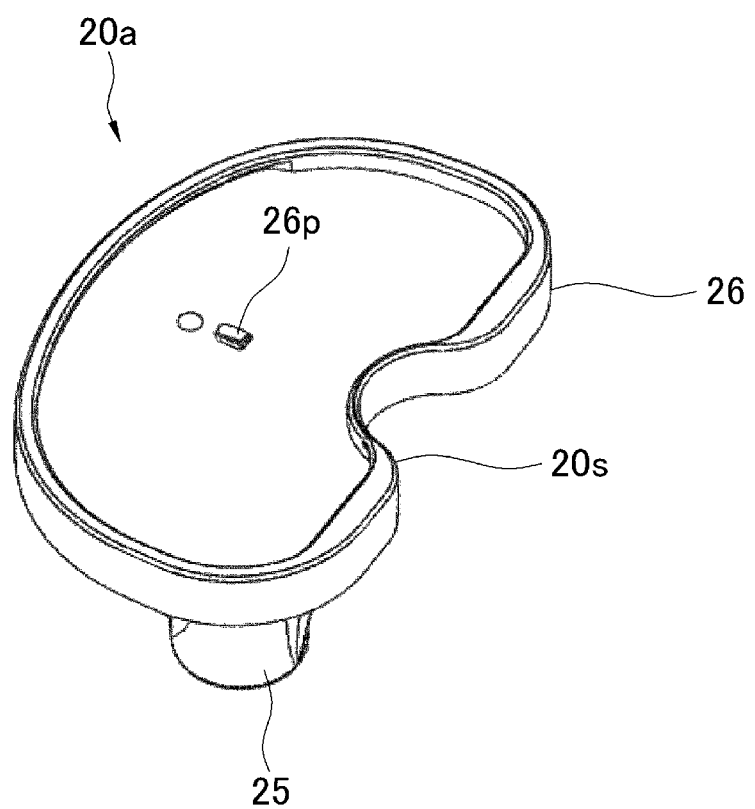
FIG. 19 is a perspective view schematically illustrating a base part 20a in the tibia member 20 of the ligament reconstruction type artificial knee joint 1 of the embodiment.

The other end of the artificial ligament 30 is coupled to a coupling member 31. As illustrated in FIGS. 14 and 15, the coupling member 31 is formed such that a section of the coupling member 31 is substantially similar to a section of the fixing hole 20h. The coupling member 31 is formed such that a height of the coupling member 31 is substantially equal to a thickness of the contact part 20b. Therefore, when the coupling member 31 is inserted in the fixing hole 20h such that a bottom surface of the coupling member 31 contacts with the top surface of the base plate 26, the top surface of the coupling member 31 is substantially flush with the top surface of the contact part 20b (see FIG. 1(B)).

The coupling member 31 includes through-holes at both ends thereof, and can be fixed to the top surface of the base plate 26 by insertion of screws in the through-holes.

As illustrated in FIGS. 1(B), 14, and 15, in the coupling member 31, a pair of through-holes 31h, 31h vertically piercing the coupling member 31 are made in addition to the through-holes in which the screws are inserted. The pair of through-holes 31h, 31h are made so as to be arrayed along a long axis direction of the coupling member 31. That is, the coupling member 31 has a structure, in which the artificial ligament 30 can be hooked on a beam portion 31s between the through-holes 31h, 31h when the artificial ligament 30 is inserted in the pair of through-holes 31h, 31h. A space in which the artificial ligament 30 is accommodated is provided in a lower portion of the beam portion 31s such that the artificial ligament 30 does not pop out from the bottom surface of the coupling member 31.

Therefore, in the above configuration, the artificial ligament 30 can be provided so as to couple the femur member 10 to the tibia member 20. That is, one end of the artificial ligament 30 is hooked on the engagement part 14. The other end of the artificial ligament 30 is coupled to (engaged with) the coupling member 31, and the coupling member 31 is inserted in the fixing hole 20h of the contact part 20b. When the coupling member 31 is fixed to the top surface of the base plate 26, the artificial ligament 30 can be provided so as to couple the femur member 10 to the tibia member 20. The coupling member 31 is inserted in the fixing hole 20h of the contact part 20b, the coupling member 31 is fixed to the top surface of the base plate 26, and the other end of the artificial ligament 30 is fixed to the tibia member 20. Hereinafter, sometimes this is referred to as "the other end of the artificial ligament 30 is coupled to the fixing hole 20h".

The engagement part 14 is formed at the position where the original anterior cruciate ligament ACL and the distal end DT of the original femur F are coupled together when the femur member 10 is mounted at the distal end DT of the femur F. The opening of the fixing hole 20h is located at the position where the original anterior cruciate ligament ACL and the original tibia E are coupled together when the tibia member 20 is mounted on the proximal end PE of the tibia E. Therefore, when both the ends of the artificial ligament 30 are coupled to the engagement part 14 and the fixing hole 20h, the artificial ligament 30 is disposed at the position of the original anterior cruciate ligament ACL. That is, the artificial ligament 30 can be disposed at the position where once the anterior cruciate ligament ACL is disposed in the knee joint replaced for the artificial knee joint.

The pair of engagement holes sg, sg in which one end of the artificial ligament 30 is disposed is vertically arrayed, and the pair of through-holes 31h, 31h of the coupling member 31 disposed in the fixing hole 20*h* is disposed so as to be arrayed in a posterior and anterior direction. Therefore, the artificial ligament 30 is twisted between the engagement part 14 and the coupling member 31 (that is, the fixing hole 20*h*).

Because of the above configuration, when the knee joint is replaced for the artificial knee joint 1 according to the invention, the artificial ligament 30 can be provided at the same position as the anterior cruciate ligament ACL in the original knee while a posterior cruciate ligament PCL is reconstructed. Accordingly, the artificial ligament 30 can act similarly to the anterior cruciate ligament (healthy ligament) in the knee before being replaced for the artificial knee joint 1.

Additionally, the artificial ligament 30 has the ring shape, and the artificial ligament 30 is twisted between both the ends thereof, so that motion of the artificial ligament 30 can come close to that of the healthy ligament when the knee is bent and stretched. When the knee is bent and stretched, a twisted state or a distance between both the ends of the artificial ligament 30 changes, and the tensile force generated by the artificial ligament also changes, so that the tensile force generated by the artificial ligament 30 can be brought close to that generated by the healthy ligament.

In the above example, the artificial ligament 30 has the ring shape, and is twisted between both the ends of the artificial ligament 30. This enables the artificial ligament 30 to surely generate the twist in association with the knee joint bending and stretching motion. When the knee is bent and stretched, the movement of the artificial ligament 30 is easily brought close to that of the healthy ligament. However, the artificial ligament 30 may not necessarily be twisted between both the ends thereof. That is, the artificial ligament 30 may be provided such that the twist is not generated or is slightly generated while the knee is stretched. Even in this case, when both the ends of the artificial ligament 30 are coupled to the femur member 10 and the tibia member 20 such that the twist is generated in association with the knee joint bending and stretching motion, the movement of the artificial ligament 30 can be brought close to that of the healthy posterior cruciate ligament in bending and stretching the knee.

In the above example, the artificial ligament 30 has the ring shape. However, the artificial ligament 30 may not necessarily have the ring shape. That is, both the ends of the artificial ligament 30 may be formed into the ring shape or the simple string shape. Even in this case, when the artificial ligament 30 is provided such that the twist or the tensile force is appropriately generated in the string-shaped portion in association with the knee joint bending and stretching motion, the movement of the artificial ligament 30 can be brought close to that of the healthy posterior cruciate ligament in bending and stretching the knee.

(Mounting Example of Artificial Knee Joint 1 of the Embodiment)

The work to mount the artificial knee joint 1 of the embodiment will be described below.

As to the knee on which the artificial knee joint 1 is mounted, the distal end DT of the femur F is partially cut off, and formed into the shape on which the femur member 10 can be mounted. Specifically, the medial condyle MC and lateral condyle LC of the femur F are formed into the shape that comes into close contact with inner surfaces of the medial condyle 11 and lateral condyle 12 of the femur member 10.

The proximal end PE of the tibia T is also partially cut off, and formed into the shape on which the base part 20*a* of the tibia member 20 can be mounted. Specifically, the proximal end PE of the tibia T is cut off such that an end surface of the proximal end PE of the tibia T becomes flat. Because the tibia member 20 includes the stem 25, a hole into which the stem 25 is inserted is also made in the end surface of the proximal end PE of the tibia T.

At this time, the anterior cruciate ligament ACL and the posterior cruciate ligament PCL are cut off in the ligaments connecting the distal end DT of the femur F and the proximal end PE of the tibia T.

In the case that the posterior cruciate ligament PCL is preserved, only the anterior cruciate ligament ACL is cut off.

Then the femur member 10 is mounted so as to cover the distal end DT of the femur F. Therefore, at the distal end DT of the femur F, the medial condyle MC and lateral condyle LC of the femur F are covered with the medial condyle 11 and lateral condyle 12 of the femur member 10.

One end of the artificial ligament 30 is previously hooked on the engagement part 14 before the femur member 10 is mounted on the distal end DT of the femur F. The other end of the artificial ligament 30 is also previously mounted on the coupling member 31.

The tibia member 20 is mounted on the proximal end PE of the tibia T. At this time, the tibia member 20 is mounted on the proximal end PE of the tibia T such that the stem 25 is inserted into the hole made in the end surface of the proximal end PE of the tibia T, and such that the bottom surface of the base plate 26 in the base part 20*a* of the tibia member 20 comes into surface-contact with the end surface of the proximal end PE of the tibia T. Therefore, at the proximal end PE of the tibia T, the medial condyle MC and lateral condyle LC of the tibia T are replaced for the medial condyle 21 and lateral condyle 22 of the contact part 20*b* of the tibia member 20. An intercondylar eminence E of the tibia T is replaced for the intercondylar eminence 23 of the contact part 20*b* of the tibia member 20.

(Reconstruction of Posterior Cruciate Ligament PCL)

The femur member 10 includes the gap 10*h* between the medial condyle 11 and the lateral condyle 12, and the notch 20*s* is formed between the medial condyle 21 and lateral condyle 22 in the rear portion of the tibia member 20. Therefore, a space communicating the proximal end PE of the tibia T and the distal end DT of the femur F with each other through the notch 20*s* and the gap 10*h* is formed. That is, the space is formed in the portion at which the posterior cruciate ligament PCL exists even if the femur member 10 and the tibia member 20 are mounted on the distal end DT of the femur F and the proximal end PE of the tibia T.

When the reconstruction ligament is disposed so as to pass through the notch 20*s* and the gap 10*h*, the posterior cruciate ligament PCL can be reconstructed. Specifically, at the distal end DT of the femur F, one of ends of the reconstruction ligament is joined to the position to which once one of ends of the original posterior cruciate ligament PCL is connected. On the other hand, at the proximal end PE of the tibia T, the other end of the reconstruction ligament is joined to the position to which once the other end of the original posterior cruciate ligament PCL is connected. Therefore, the reconstruction ligament is disposed at the position where once the original posterior cruciate ligament PCL exists, so that the posterior cruciate ligament PCL can be reconstructed by the reconstruction ligament.

In the case that the posterior cruciate ligament PCL is preserved, the posterior cruciate ligament PCL can be disposed in the notch 20*s* and the gap 10*h*. That is, the posterior cruciate ligament PCL can be disposed at the original position.

(Mounting of Artificial Ligament 30)

The coupling member 31 engaged with the other end of the artificial ligament 30 is inserted in the fixing hole 20h of the contact part 20b of the tibia member 20, and the coupling member 31 is fixed to the base plate 26 of the base part 20a using a screw. Therefore, the femur member 10 and the tibia member 20 are coupled together by the artificial ligament 30. The engagement part 14 is formed so as to be disposed at the position where the original anterior cruciate ligament ACL and the distal end DT of the original femur F are coupled together when the femur member 10 is mounted on the distal end DT of the femur F. The opening of the fixing hole 20h is formed so as to be disposed at the position where the original anterior cruciate ligament ACL and the original tibia E are coupled together when the tibia member 20 is mounted on the proximal end PE of the tibia E. Accordingly, the artificial ligament 30 can be disposed at the position where once the anterior cruciate ligament ACL is disposed in the knee joint replaced for the artificial knee joint.

As described above, one end of the artificial ligament 30 is engaged with the engagement part 14, and the coupling member 31 engaged with the other end of the artificial ligament 30 is fixedly inserted in the fixing hole 20h of the contact part 20b of the tibia member 20, so that the artificial ligament 30 can be mounted so as to couple the femur member 10 and the tibia member 20. Accordingly, the artificial ligament 30 is easy to mount, and a medical treatment time can be shortened.

The tensile force generated in the artificial ligament 30 can be adjusted by a change of the state in which the coupling member 31 is fixed to the fixing hole 20h of the tibia member 20. Accordingly, an initial state of the artificial ligament 30 can properly be adjusted according to a knee state of a patient. For example, in the case that the coupling member 31 is fixed to the top surface of the base plate 26 using a screw, the tensile force generated in the artificial ligament 30 can be adjusted by changing a screw tightening state. When the height of the coupling member 31 can be adjusted, the tensile force generated in the artificial ligament 30 can be adjusted even in the same screw tightening state. For example, a spacer is provided between the top surface of the base plate 26 and the coupling member 31. Therefore, the position (that is, the position relative to the contact part 20b) of the top surface of the coupling member 31 is adjusted by the spacer, so that the tensile force generated in the artificial ligament 30 can be adjusted even in the same screw tightening state.

The engagement part 14 and the opening of the fixing hole 20h are formed at the position where once the anterior cruciate ligament ACL is coupled to the distal end DT of the femur F in the knee replaced for the artificial knee joint 1 and the position where once the tibia member 20 is coupled to the proximal end PE of the tibia E in the knee replaced for the artificial knee joint 1, respectively. However, there is no particular limitation to a method for deciding the position where the engagement part 14 or the opening of the fixing hole 20h is provided. For example, the position of the anterior cruciate ligament ACL of a person on whom the artificial knee joint 1 is mounted is previously checked, and the position where the engagement part 14 or the fixing hole 20h is provided may be decided based on the check.

Figure 25:
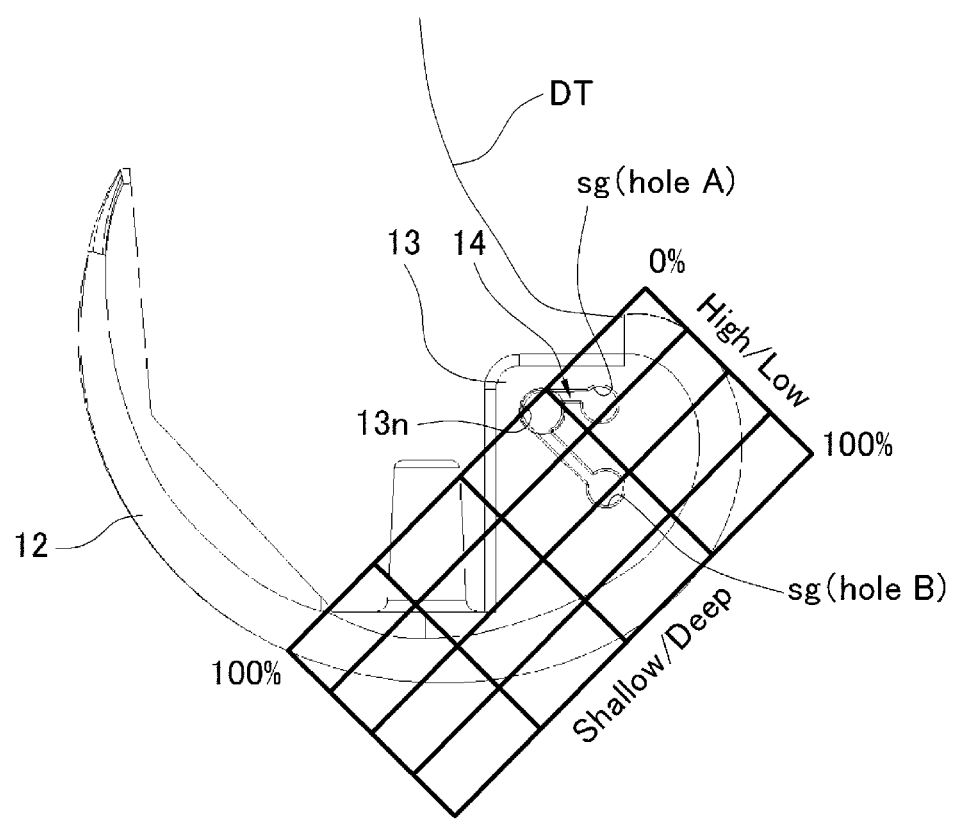
FIG. 25 is a view schematically illustrating a position at which the engagement part 14 of the femur member 10 is provided.
Figure 26:
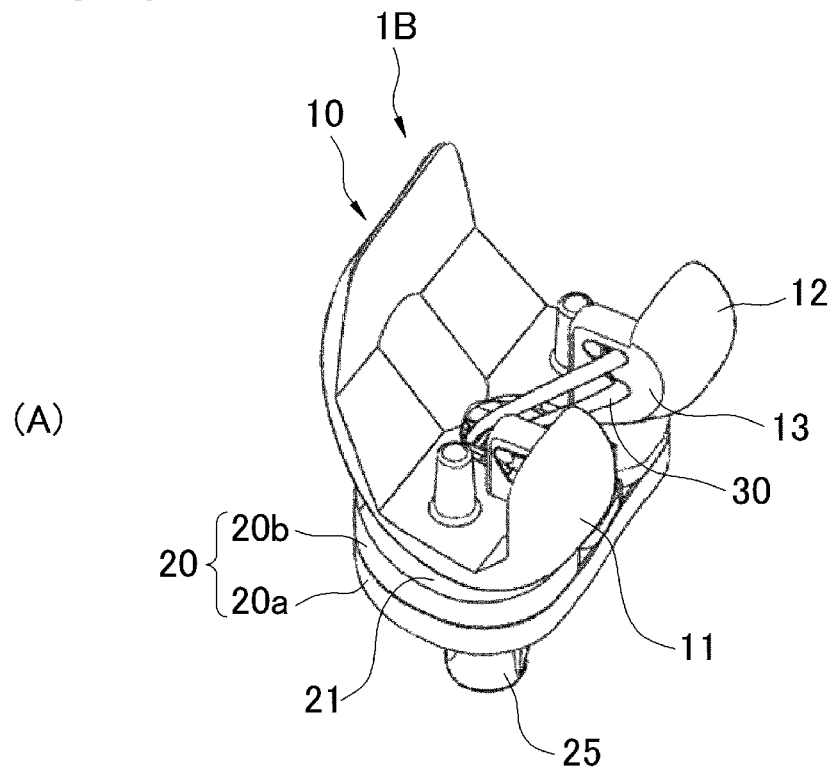
FIGS. 26(A) and 26(B) are perspective and sectional views schematically illustrating a ligament reconstruction type artificial knee joint 1B according to another embodiment, respectively.
Figure 26:
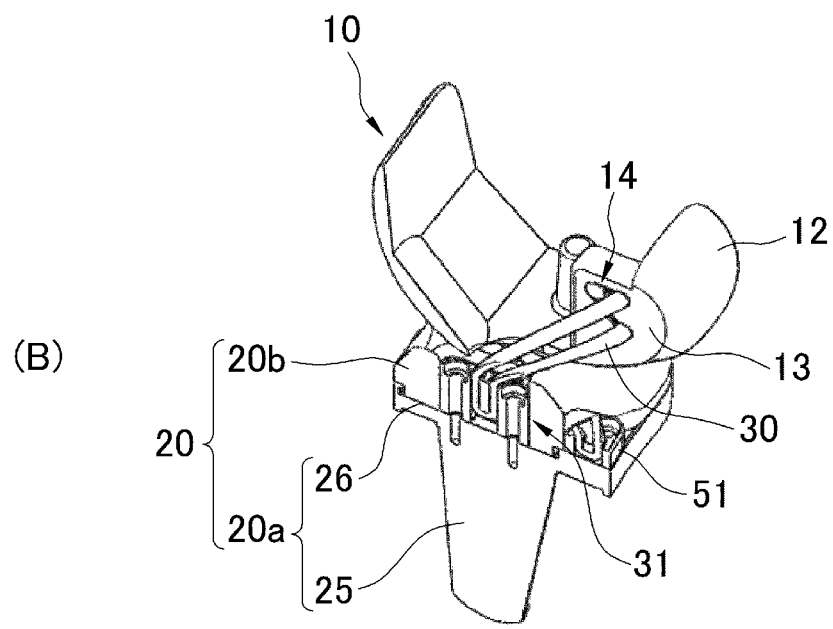

The positions of the anterior cruciate ligaments ACL of plural persons are measured, and the position where the engagement part 14 or the fixing hole 20h is provided may statistically be decided. For example, as illustrated in FIG. 25, a shallow/deep direction and a high/low direction from a front-side surface are defined in the femur member 10. In the engagement holes sg, sg of the engagement part 14, the upper engagement hole sg is referred to as a hole A, and the lower engagement hole sg is referred to as a hole B. The engagement part 14 is provided such that, when the femur member 10 is mounted on the distal end DT of the femur F, one end of the artificial ligament 30 is disposed in the hole A located ranging from about 12% to about 30% and the hole B located ranging from about 25% to about 40% in the shallow/deep direction, and in the hole A located ranging from about 10% to about 40% and the hole B located ranging from about 35% to about 60% in the high/low direction. The fixing hole 20h is made such that the other end of the artificial ligament 30 is disposed at the position ranging from about 33% to about 46% from the front and the position ranging from 0% to about 5% from the center of a right and left direction in the top surface of the contact part 20b of the tibia member 20. Therefore, when the artificial ligament 30 is simply mounted by the above method, the artificial ligament 30 can be disposed at the substantially same position as the position of the original anterior cruciate ligament ACL of the person on whom the artificial knee joint 1 is mounted.

Study results of the inventors show that, in bending and stretching the knee, an anterior cruciate ligament ACL of a person changes depending on the bending angle between the state in which the anterior cruciate ligament ACL is stretched by applying the tensile force and the state in which the tensile force is weakened to slightly relieve the anterior cruciate ligament ACL. It is also found that the change slightly depends on a distance from the center axis of the anterior cruciate ligament ACL or the position of the anterior cruciate ligament ACL. Therefore, in the case that the engagement part 14 and coupling member 21 having the above shapes are used, namely, in the case that two artificial ligaments 30 are disposed between the femur member 10 and the tibia member 20, the reconstructed anterior cruciate ligament ACL, namely, the two artificial ligaments 30 can be put in different tension states. Accordingly, the function of the reconstructed anterior cruciate ligament ACL, namely, the artificial ligament 30 can be brought close to that of the anterior cruciate ligament of the healthy person.

In addition to the disposition of the reconstructed anterior cruciate ligament ACL, when the tibia member 20 includes the shapes of the medial condyle 21 and lateral condyle 22 (to be described later) and the intercondylar eminence 23, the movement of the artificial ligament 30 can be brought closer to the movement of the original anterior cruciate ligament ACL of the person on whom the artificial knee joint 1 is mounted.

When the coupling member 31 is mounted on the fixing hole 20h of the tibia member 20, because the position of the pair of through-holes 31h, 31h depends slightly on sexuality or a race even within the above range, the position may be changed according to a corresponding category of each patient. For example, the tibia member 20 in which the fixing hole 20h is made is used such that the center of the fixing hole 20h (that is, the center of the coupling member 31, the middle of the pair of through-holes 31h, 31h in FIG. 15) is disposed at the position of 33% to 46% from the front in the top surface of the tibia member 20, and such that the center of the fixing hole 20h is disposed at the position of 0 to 5% from the center in the right and left direction in the top surface of the tibia member 20. When the coupling member 31 is fixedly inserted in the fixing hole 20h of the tibia member 20, the reconstruction ligament ACL can be disposed at the position of the anterior cruciate ligament ACL of a person on whom the artificial knee joint 1 is mounted.

As described above, the study results of the inventors show that, in the anterior cruciate ligament ACL, the tensile force generating status depends on the distance from the center axis when the knee is bent and stretched. In the normal anterior cruciate ligament ACL, it is found that the anterior cruciate ligament ACL is formed by plural bundles of ligaments, and that the tensile force generating status depends on each bundle when the knee is bent and stretched. Accordingly, in the case that the anterior cruciate ligament ACL to be reconstructed is formed by the plural ligament members (see FIGS. 41 to 46), the anterior cruciate ligament reconstructed using the artificial knee joint 1 can be brought closer to the function of the original anterior cruciate ligament ACL. In this case, the tensile force generated in each bundle is brought closer to the tensile force generated in the bundle of the ligaments disposed at the same position or the near position in the anterior cruciate ligament ACL to be reconstructed, so that the function closer to the original anterior cruciate ligament ACL can be exerted.

(Medial Condyle 21 and Lateral Condyle 22 of Tibia Member 20)

Although there is no limitation to the shapes of the medial condyle 21 and lateral condyle 22 of the tibia member 20, desirably the shapes of the medial condyle 21 and lateral condyle 22 are formed into the shape similar to the tibia E of a living body. Specifically, the medial condyle 21 is larger than the lateral condyle 22 in planar view, and while the top surface of the medial condyle 21 is formed into the concave shape (downward convex curved surface), desirably the top surface of the lateral condyle 22 is formed into a flat shape (see FIGS. 7 to 10).

In this case, even if the posterior cruciate ligament PCL is present while the anterior cruciate ligament ACL is absent, the knee becomes unstable because the lateral condyle 22 is formed into the flat surface. That is, the lateral condyle 12 of the femur member 10 slips back and forth or from side to side with respect to the lateral condyle 22 of the tibia member 20, and the knee cannot stably move. On the other hand, since the artificial knee joint 1 of the embodiment includes the artificial ligament 30 at the substantially same position as the original anterior cruciate ligament ACL, the lateral condyle 12 of the femur member 10 can be attracted toward the lateral condyle 22 of the tibia member 20 by the artificial ligament 30. Accordingly, even if the lateral condyle 22 is formed into the flat surface, the lateral condyle 12 of the femur member 10 can be moved while being in contact with the lateral condyle 22 of the tibia member 20. Additionally, force attracting the lateral condyle 12 of the femur member 10 toward the inside, namely, the side of the medial condyle 11 of the femur member 10 is also applied to lateral condyle 12. Therefore, in bending the knee, the movement of the lateral condyle 12 of the femur member 10 can be equalized to the natural movement (arc motion) of the knee.

More desirably the medial condyle 21 of the tibia member 20 tilts backward relative to the lateral condyle 22 while the surfaces of the medial condyle 21 and lateral condyle 22 tilt inward. In this case, when the posterior cruciate ligament PCL is present while the anterior cruciate ligament ACL is absent, the knee moves unstable. On the other hand, in the artificial knee joint 1 of the embodiment, the posterior cruciate ligament PCL is reconstructed, the artificial ligament 30 is provided at the substantially same position as the original anterior cruciate ligament ACL, and the medial condyle 21 and lateral condyle 22 of the tibia member 20 are formed into the above shape, which allows the artificial knee joint 1 to stably perform the movement closer to the natural knee.

For example, desirably the top surface of the medial condyle 21 tilts backward by about 3° to about 7° with respect to the top surface of the lateral condyle 22. When being mounted on the tibia T, desirably the tibia member 20 tilts inward by about 3° to about 7° with respect to a direction orthogonal to the axis direction of the tibia T (that is, about 3° to about 7° with respect to a direction orthogonal to the axis direction of the stem 25). The top surface of the medial condyle 21 used to determine a backward tilt angle means a surface connecting a front end and a rear end of the medial condyle 21 when the medial condyle 21 is viewed from the side surface. The top surface of the medial condyle 21 used to determine an inward tilt angle means a surface connecting a right end and a left end of the medial condyle 21 when the medial condyle 21 is viewed from the rear surface.

In the tibia member 20, desirably the peripheral portion of the medial condyle 21 and/or lateral condyle 22 is formed into a curved shape. That is, desirably the surface of the medial condyle 21 is continuously connected to the peripheral portion of the medial condyle 21 by the curved surface. Desirably the surface of the lateral condyle 22 is continuously connected to the peripheral portion of the lateral condyle 22 by the curved surface.

Figure 9:
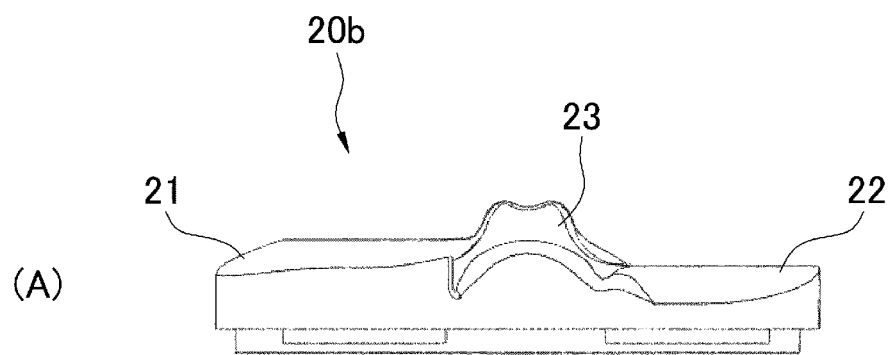
FIGS. 9(A) and 9(B) are rear and front views schematically illustrating the contact part 20b in the tibia member 20 of the ligament reconstruction type artificial knee joint 1 of the embodiment, respectively.
Figure 9:
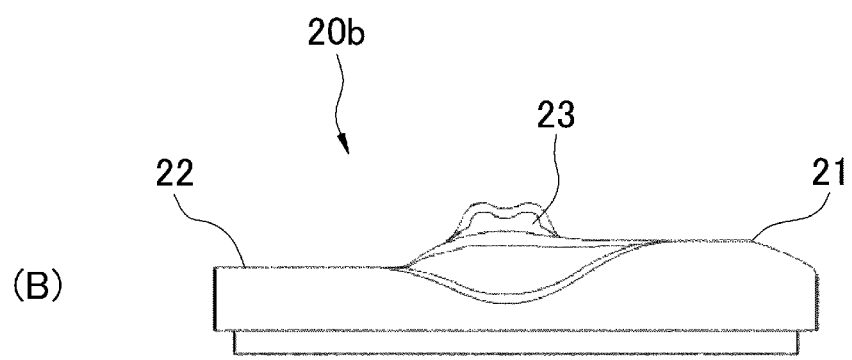
Figure 10:
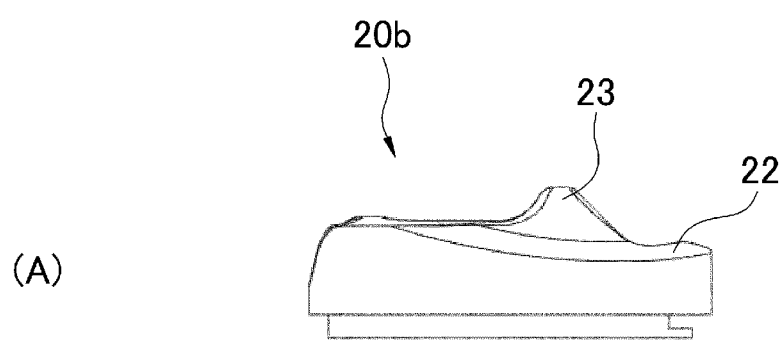
FIGS. 10(A) and 10(B) are right and left side views schematically illustrating the contact part 20b in the tibia member 20 of the ligament reconstruction type artificial knee joint 1 of the embodiment, respectively.
Figure 10:
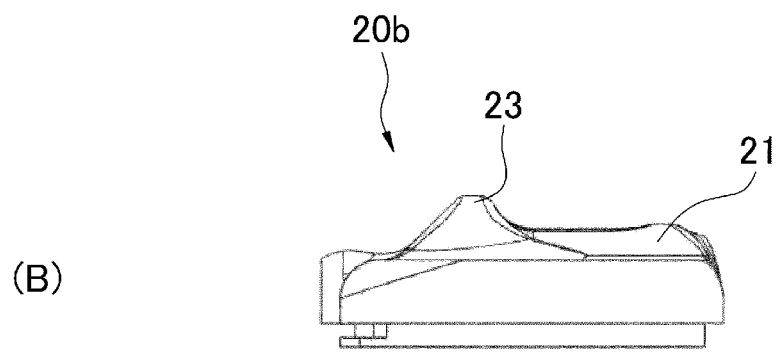

For example, as illustrated in FIGS. 9 and 10, desirably the portion in which the intercondylar eminence 23 and the medial condyle 21 and/or lateral condyle 22 are continuously connected to each other or the portion (in FIGS. 7 and 8, portions 21a and 22a) in which the intercondylar eminence 23 and the medial condyle 21 and/or lateral condyle 22 are continuously connected to other portions is formed into a downward concave curve. That is, in the tibia member 20, desirably the portion except for the portion in which the side surface, rear surface, and front surface of the tibia member 20 are continuously connected to the medial condyle 21 and/or lateral condyle 22 is formed into the downward concave curve.

As illustrated in FIGS. 7 to 10, desirably a boundary portion between the side surface and/or rear surface of the tibia member 20 and the lateral condyle 22 is formed into an outward convex surface. That is, desirably the tibia member 20 is formed so as to become a curved surface (that is, arc section) in which the lateral surface and/or rear surface of the tibia member 20 is smoothly connected to the lateral condyle 22 in the lateral portion and/or rear portion of the lateral condyle 22 of the tibia member 20.

When the peripheral portions of the medial condyle 21 and/or lateral condyle 22 are formed as described above, the edge loading can be reduced for the following reason.

The medial condyle 21 of the tibia member 20 is in contact with the surface of the medial condyle 11 of the femur member 10, and the relative position between the medial condyle 21 and the medial condyle 11 changes in bending the knee. At this time, the medial condyle 11 of the femur member 10 moves toward the edge (peripheral portion) of the medial condyle 21 of the tibia member 20 or the intercondylar eminence 23. A portion in which the medial condyle 11 of the femur member 10 and the medial condyle 21 of the tibia member 20 come into strong contact with each other is not generated when the peripheral portion of the medial condyle 21 of the tibia member 20 is formed as described above. Specifically, the state in which a contact area between the medial condyle 11 and the medial condyle 21 is reduced to extremely increase a surface pressure is not generated. That is, because the edge loading can be reduced, the damage of the medial condyle 11 of the femur member 10 and the medial condyle 21 of the tibia member 20 can be prevented to improve durability of the artificial knee joint 1.

Similarly, when the peripheral portion of the lateral condyle 22 of the tibia member 20 is formed as described above, the edge loading can be reduced between the lateral condyle 22 of the tibia member 20 and the lateral condyle 12 of the femur member 10. The damage of the lateral condyle 12 of the femur member 10 and the lateral condyle 22 of the tibia member 20 can be prevented to improve durability of the artificial knee joint 1.

In particular, when the peripheral portion of the lateral condyle 22 of the tibia member 20 is formed as described above, a post-operation movable range can be improved while the edge loading is reduced. Even if the knee joint is replaced for the artificial knee joint 1 of the embodiment, the movable range can be brought close to that of the healthy knee joint compared with the conventional artificial knee joint when the knee joint is moved (that is, in stretching, bending, or twisting the knee). For example, the deeply bending motion such as straight sitting is permitted.

In the shape of the curved surface in the boundary portion between the medial condyle 21 and/or lateral condyle 22 and its peripheral portion, there is no particular limitation to a curvature radius as long as the medial condyle 21 and/or the lateral condyle 22 is smoothly connected to the peripheral portion.

The curvature radius of the curved surface in the boundary portion may depend on the position.

The boundary portion between the side surface and/or rear surface and the medial condyle 21 and/or lateral condyle 22 may be formed into not the arc shape but the flat shape. That is, a corner formed between the side surface and/or rear surface and the medial condyle 21 and/or lateral condyle 22 may be chamfered. However, when the boundary portion is formed into the curved surface, the edge loading can be reduced compared with the chamfering, and the post-operation movable range can be improved, which is preferable.

In the embodiment, the side surface and/or rear surface and the lateral condyle 22 of the tibia member 20 are formed into the smoothly-connected curved surface. The boundary portion between the front surface and lateral condyle 22 of the tibia member 20 may also be formed into the smoothly-connected curved surface.

(Intercondylar Eminence 23)

In the tibia member 20, the intercondylar eminence 23 is formed between the medial condyle 21 and the lateral condyle 22 and between the fixing hole 20h and the notch 20s. Preferably the height of the intercondylar eminence 23 is formed substantially equal to that of the intercondylar eminence 23 in the knee before being replaced for the artificial knee joint 1. Force attracting the lateral condyle 12 of the femur member 10 onto the side of the medial condyle 21 of the tibia member 20 is generated when the artificial ligament 30 is provided at the substantially same position as the original anterior cruciate ligament ACL. When the lateral condyle 22 is formed into the flat surface, the lateral condyle 12 of the femur member 10 moves easily toward the inside. However, when the height of the intercondylar eminence 23 is formed as described above, the above-described movement of the lateral condyle 12 of the femur member 10 is limited, so that the knee replaced for the artificial knee joint 1 can be stabilized.

As used herein, the height of the intercondylar eminence 23 means a height from the top surface of the lateral condyle 22 of the tibia member 20. However, the height may not necessarily be equalized to that of the intercondylar eminence 23 in the knee before being replaced for the artificial knee joint 1. For example, the height may be set to about 70% to about 120% of height of the intercondylar eminence 23 in the knee before being replaced for the artificial knee joint 1.

A slight recess similar to the tibia T of a living body is provided at a leading end of the intercondylar eminence 23. The tensile force can properly be generated in the artificial ligament 30 interfering with the intercondylar eminence 23 by providing the recess. Particularly, as described above, in the case that the artificial ligament 30 is formed by the plural ligament members (see FIGS. 41 to 45), the provision of the slight recess changes the interference state in each ligament member when the plural ligament members interfere with the leading end of the intercondylar eminence 23. That is, the tensile force generated in each ligament member is adjusted so as to be in a proper state, so that the movement of the artificial ligament 30 (that is, the anterior cruciate ligament ACL) or the generated tensile force can be equalized to that of an anterior cruciate ligament of a human.

(Tibia Member 20)

In the tibia member 20, the base part 20a and the contact part 20b may integrally be formed. However, as described above, desirably the base part 20a (FIGS. 11 to 13) and the contact part 20b (FIGS. 7 to 10) are separately formed, and the tibia member 20 is formed by a combination of the base part 20a and the contact part 20b. For example, the medial condyle 21, the lateral condyle 22, the contact part 20b including the intercondylar eminence 23 may be formed so as to be detachably attached to the base part 20a. In this case, each region can be made of a material suitable for required functions. For example, the base part 20a in which strength is required can be made of a material having high biocompatibility and high rigidity (such as titanium and cobalt-chromium), and the contact part 20b can be made of a material having high sliding and wear-resistant properties (such as ultrahigh molecular polyethylene). Because each region can be made of a material suitable for the required function, the durability of the artificial knee joint 1 can be improved while the smooth movement of the artificial knee joint 1 is ensured.

Figure 11:
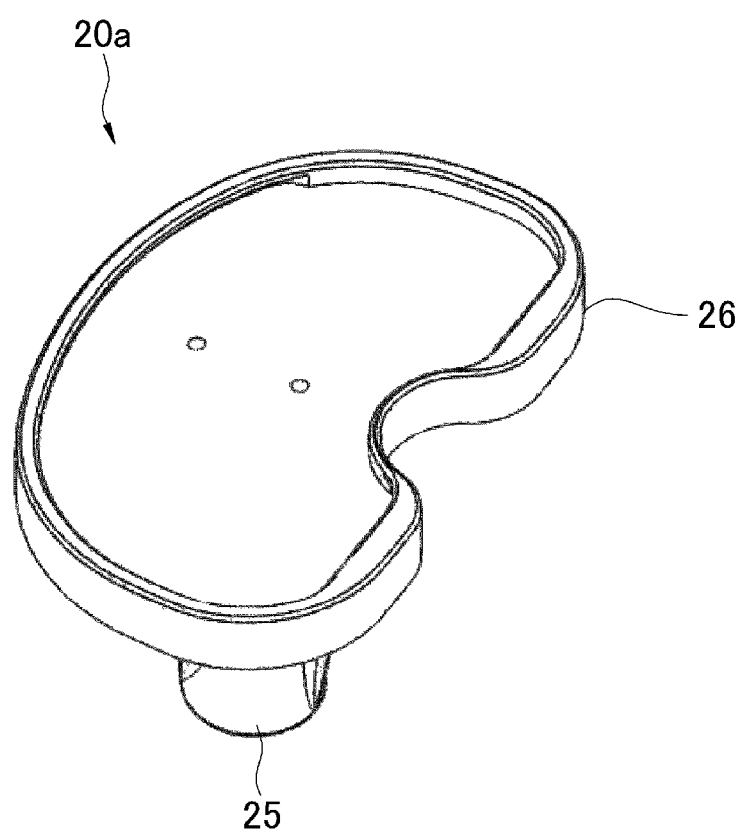
FIG. 11 is a perspective view schematically illustrating a base part 20a in the tibia member 20 of the ligament reconstruction type artificial knee joint 1 of the embodiment.

There is no particular limitation to the method for joining the base part 20a and the contact part 20b to each other. A known method for joining a portion corresponding to the base part 20a and a portion corresponding to the contact part 20b to each other in the conventional artificial knee joint can be adopted. For example, as illustrated in FIG. 11, a recess is provided in the top surface of the base part 20a, and an engagement part is formed in an inside wall of the recess. On the other hand, as illustrated in FIG. 10, a fitting portion fitted in the recess of the top surface of the base part 20a is provided in the lower surface of the contact part 20b, and a flange portion that engages with the engagement part is provided in the side surface of the fitting portion. The fitting portion of the contact part 20b is inserted in the recess of the top surface of the base part 20a to cause the flange portion to engage with the engagement part, which allows the base part 20a and the contact part 20b to be firmly fixed to each other. Even if the femur member 10 and the tibia member 20 move relative to each other, the base part 20a and the contact part 20b can be prevented from shifting or moving.

(Ligament Reconstruction Type Artificial Knee Joint 1B)

In the above example, the artificial knee joint 1 includes only the artificial ligament 30 acting as the anterior cruciate ligament. That is, the artificial knee joint 1 does not include the artificial ligament constituting the posterior cruciate ligament. Even in such cases, when the posterior cruciate ligament is preserved, or when the posterior cruciate ligament is reconstructed by a known method, both the cruciate ligaments can act like the healthy knee even if the knee is replaced for the artificial knee joint 1.

However, when the artificial knee joint 1 includes an artificially-formed posterior cruciate ligament (artificial posterior cruciate ligament), operativeness of the knee is easily adjusted when the knee is replaced for the artificial knee joint 1. A relatively positional relationship or interaction between the artificial ligament 30 acting as the anterior cruciate ligament and the artificial posterior cruciate ligament is easily adjusted compared with the case that the posterior cruciate ligament is reconstructed aside from the artificial knee joint 1.

The ligament reconstruction type artificial knee joint 1B (hereinafter, simply referred to as an artificial knee joint 1B) including an artificial posterior cruciate ligament 35 will be described below with reference to FIGS. 26 to 40.

In the artificial knee joint 1B, the description of the part having the configuration equivalent to the above artificial knee joint 1 (that is, the artificial knee joint 1 including only the artificial ligament 30 acting as the anterior cruciate ligament) is properly omitted.

In FIGS. 26 to 40, the artificial knee joint 1B for the right knee is described as a representative similarly to the artificial knee joint 1. For clarification of the structure, the femur F and the tibia T are omitted in FIGS. 26 to 40.

(Femur Member 10)

In the artificial knee joint 1B, similarly to the femur member 10 of the artificial knee joint 1, the lateral condyle inside wall 13 is provided inside the lateral condyle 12 of the femur member 10. The engagement part 14 engaged with one end of the artificial ligament 30 is provided in the lateral condyle inside wall 13.

On the other hand, in the artificial knee joint 1B, a medial condyle inside wall 15 is provided inside the medial condyle 11 of the femur member 10 as illustrated in FIG. 28(B). A posterior cruciate ligament engagement part 16 is provided in the medial condyle inside wall 15. The posterior cruciate ligament engagement part 16 is formed near a position where the original posterior cruciate ligament PCL and the distal end DT of the original femur F are coupled together when the femur member 10 is mounted on the distal end DT of the femur F.

Although the posterior cruciate ligament engagement part 16 differs from the engagement part 14 formed in the lateral condyle inside wall 13 in the dispositions of the pair of engagement holes sg, sg (to be described later), the posterior cruciate ligament engagement part 16 is substantially identical to the engagement part 14 in structure. That is, the structure in which the posterior cruciate ligament engagement part 16 is engaged with the artificial posterior cruciate ligament 35 is substantially identical to the structure in which the engagement part 14 is engaged with the artificial ligament 30.

Specifically, a groove 15g is provided in the medial condyle inside wall 15 so as to pierce the medial condyle inside wall 15. The groove 15g is formed such that a width of the groove 15g is thinner than a normal diameter of the artificial posterior cruciate ligament 35 (that is, a diameter in a state in which the tensile force is not substantially applied to the artificial posterior cruciate ligament 35). The groove 15g is formed into a substantial V-shape, and the substantially triangular posterior cruciate ligament engagement part 16 is formed in the medial condyle inside wall 15 by the groove 15g. The groove 15g is formed such that a leading end of the posterior cruciate ligament engagement part 16 is directed forward.

Figure 40:
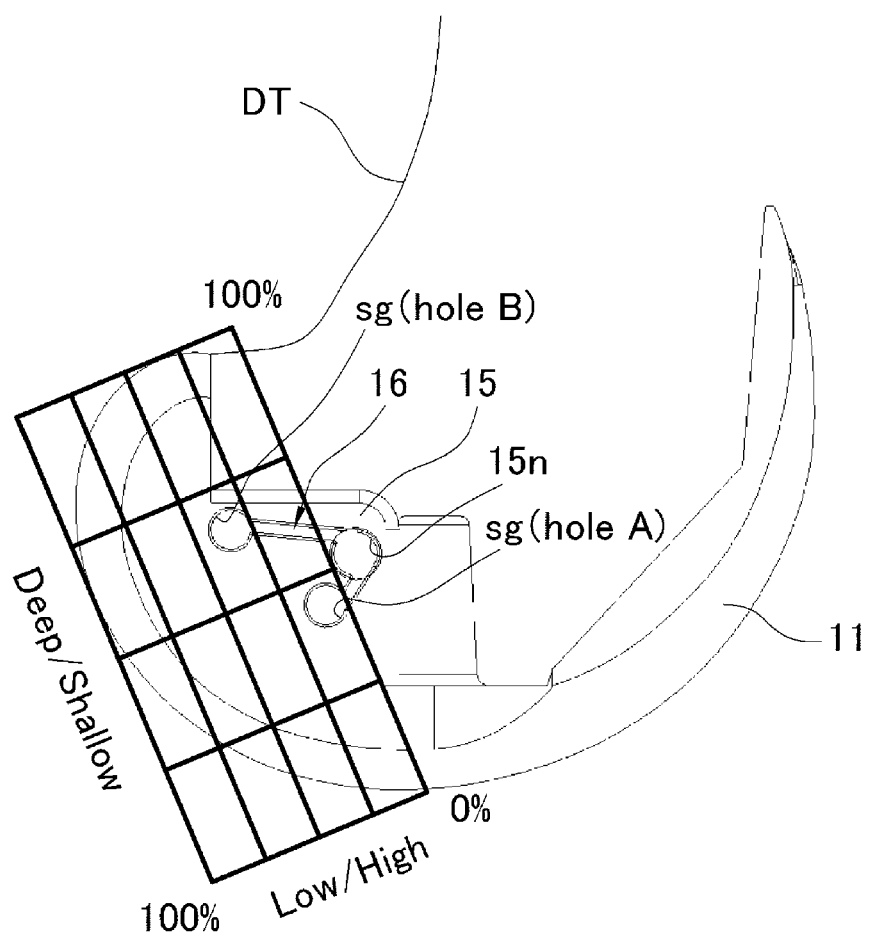
FIG. 40 is a view schematically illustrating a position at which a posterior cruciate ligament engagement part 16 of the femur member 10 is provided.
Figure 41:
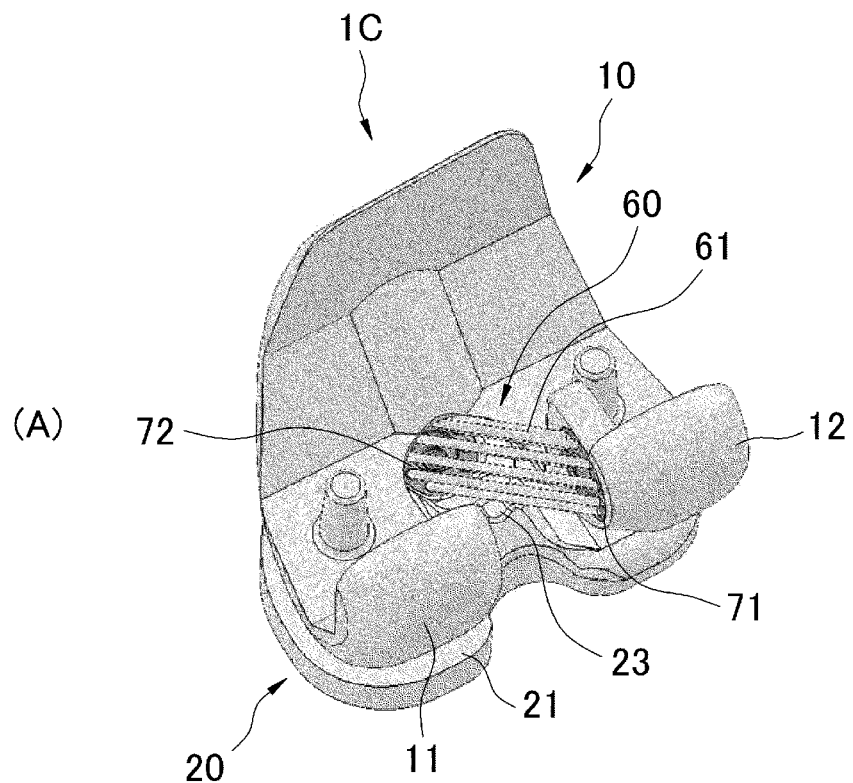
FIG. 41 is a view schematically illustrating a ligament reconstruction type artificial knee joint 1C according to another embodiment when the ligament reconstruction type artificial knee joint 1C is viewed from an obliquely rear side.
Figure 41:
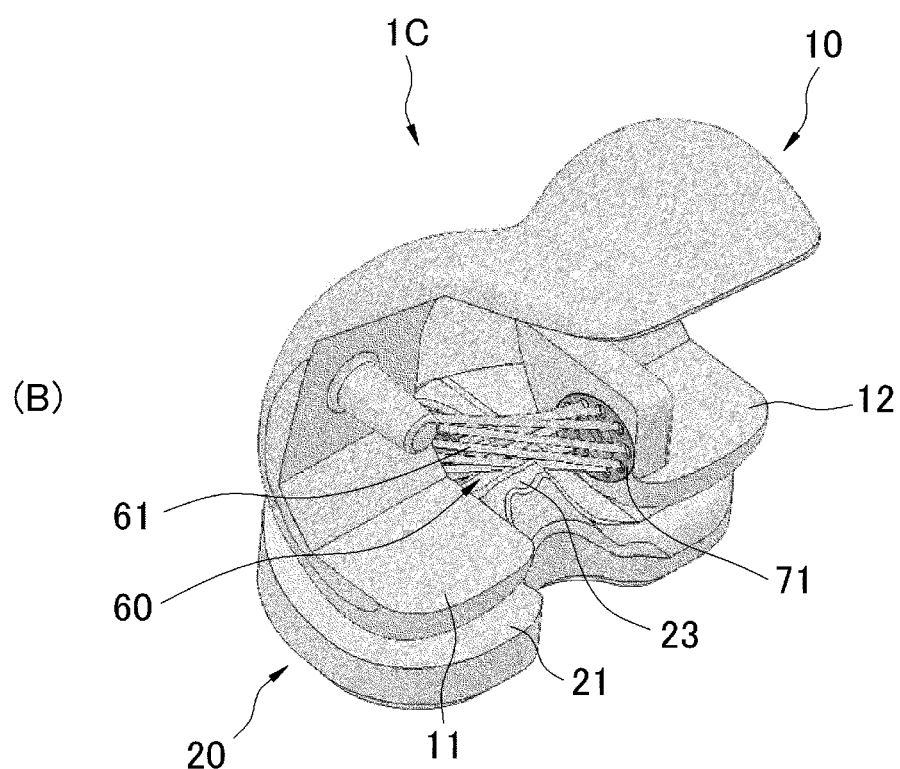
Figure 42:
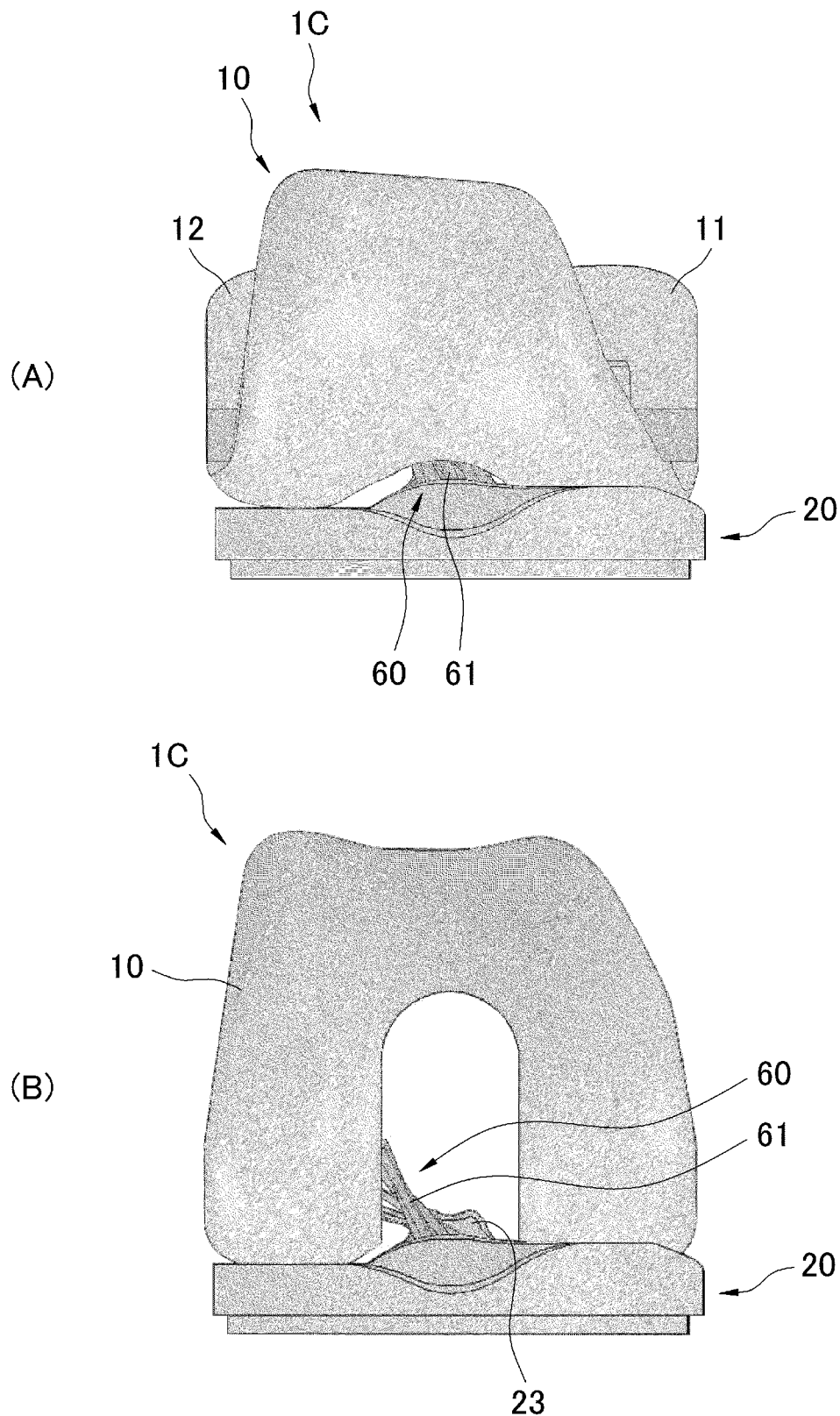
FIG. 42 is a front view schematically illustrating the ligament reconstruction type artificial knee joint 1C of another embodiment.
Figure 43:
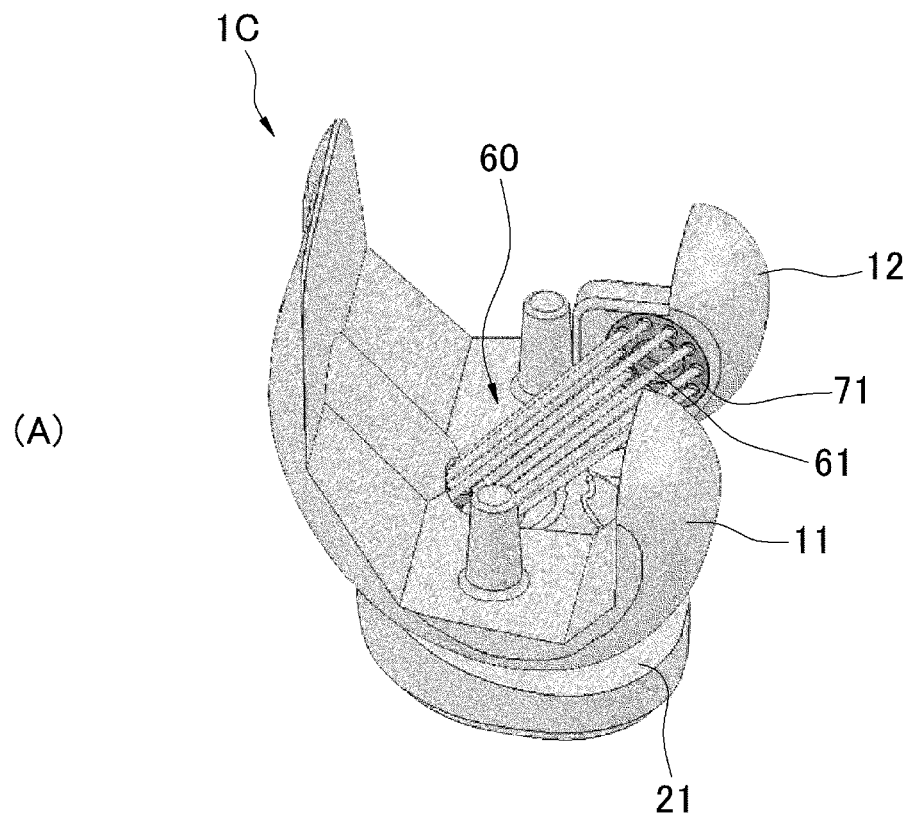
FIG. 43 is a view schematically illustrating the ligament reconstruction type artificial knee joint 1C of another embodiment when the ligament reconstruction type artificial knee joint 1C is viewed from an obliquely upper right side.
Figure 43:
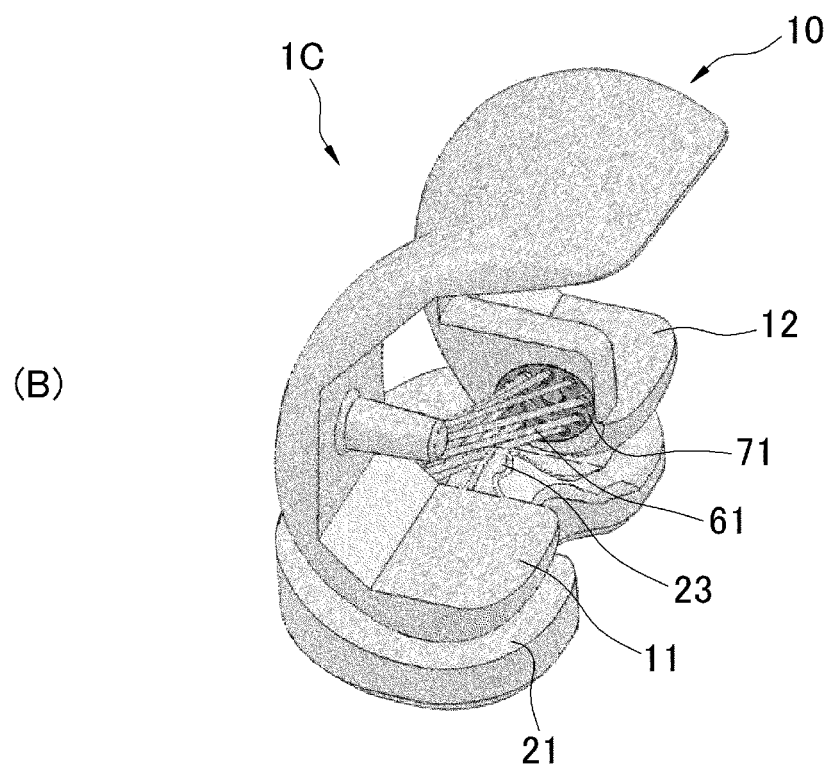
Figure 44:
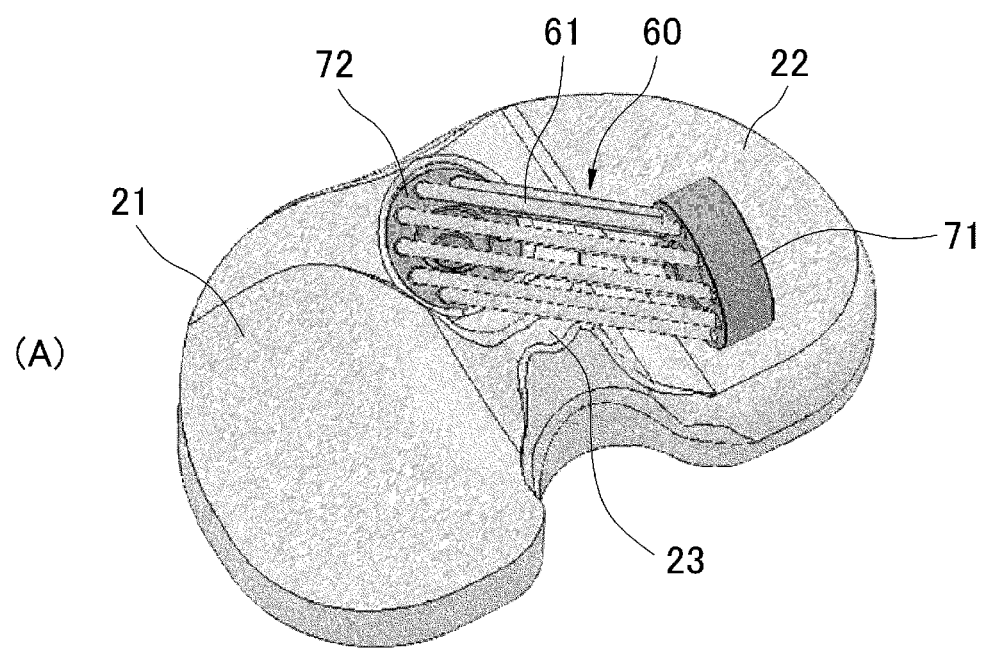
FIG. 44 is a view schematically illustrating the ligament reconstruction type artificial knee joint 1C of another embodiment while a femur member 11C is omitted.
Figure 44:
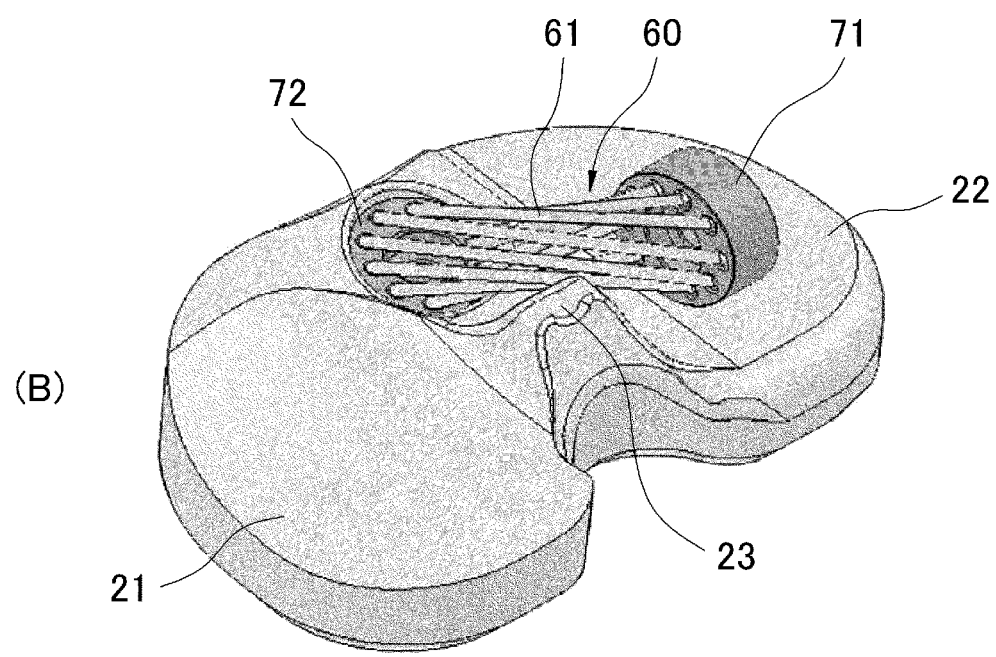
Figure 45:
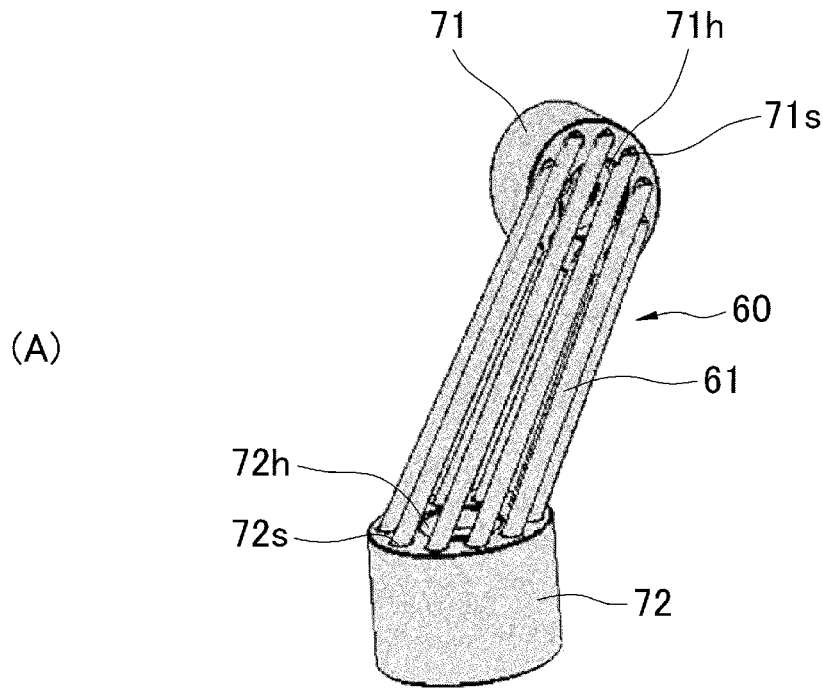
FIG. 45 is a view schematically illustrating only an artificial ligament 60, a femur coupling member 71, and a tibia coupling member 72 of the ligament reconstruction type artificial knee joint 1C of another embodiment.
Figure 45:
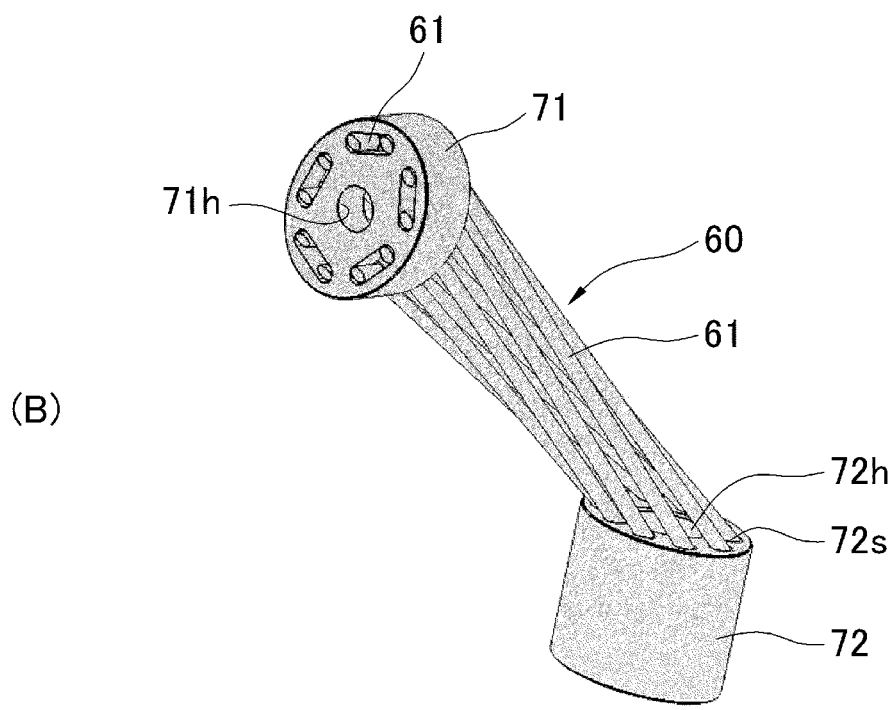

The pair of engagement holes sg, sg, which are separated from each other in the posterior and anterior direction while having different heights, is made at a base end (that is, both ends of the groove 15g) of the posterior cruciate ligament engagement part 16 (see FIG. 40). More specifically, the pair of engagement holes sg, sg is provided such that the rear-side engagement hole sg is slightly higher than the front-side engagement hole sg. The pair of engagement holes sg, sg is made such that a diameter of the pair of engagement holes sg, sg is substantially equal to the normal diameter of the artificial posterior cruciate ligament 35 (that is, the diameter in the state in which the tensile force is not substantially applied to the artificial posterior cruciate ligament 35). When the pair of engagement holes sg, sg is made, the artificial posterior cruciate ligament 35 can be coupled to the posterior cruciate ligament engagement part 16 in the state in which the artificial posterior cruciate ligament 35 is properly positioned.

Desirably a boundary portion between the pair of engagement holes sg, sg and a rear surface of the posterior cruciate ligament engagement part 16 is formed into a curved shape. In this case, the damage of the artificial posterior cruciate ligament 35 can be suppressed compared with the case that the boundary portion is formed into an edge shape.

There is no particular limitation to a shape or a size of the pair of engagement holes sg, sg and a position where the pair of engagement holes sg, sg is provided, and a positional relationship between the engagement holes sg, sg as long as the artificial posterior cruciate ligament 35 is engaged. In the case that the groove bg is provided in the rear surface of the medial condyle inside wall 15 similarly to the engagement part 14, the artificial posterior cruciate ligament 35 can firmly be engaged with the posterior cruciate ligament engagement part 16 even if the engagement hole sg is not necessarily made. In the case that the pair of engagement holes sg, sg is not mode, desirably the groove 15g is formed such that the width of the groove 15g is substantially equal to the normal diameter of the artificial posterior cruciate ligament 35.

Similarly to the engagement part 14, desirably the groove bg is formed in a rear surface (that is, the surface contacting with the inner surface of the medial condyle 11) of the medial condyle inside wall 15 (see FIG. 24). Specifically, desirably the groove bg is formed so as to connect the pair of engagement holes sg, sg to each other. In this case, the groove bg is formed such that the width and depth of the groove bg are slightly longer than a shaft diameter of the artificial posterior cruciate ligament 35. When one end of the artificial posterior cruciate ligament 35 is hooked on the pair of engagement holes sg, sg, the artificial posterior cruciate ligament 35 is perfectly accommodated in the groove bg, and the artificial posterior cruciate ligament 35 does not protrude from the rear surface of the medial condyle inside wall 15. Accordingly, when the groove bg is provided, the artificial posterior cruciate ligament 35 and the inner surface of the medial condyle 11 contact with each other to prevent the damage of the artificial posterior cruciate ligament 35. Alternatively, the pair of engagement holes sg, sg is not made, but the groove bg may be provided. Even in this case, the artificial posterior cruciate ligament 35 can be coupled to the posterior cruciate ligament engagement part 16 while positioned by the groove bg. As described above, desirably the groove 15g is formed such that the width of the groove 15g is substantially equal to the normal diameter of the artificial posterior cruciate ligament 35. Of course, in the case that the groove bg is provided together with the pair of engagement holes sg, sg, the artificial posterior cruciate ligament 35 can more stably be positioned.

Desirably the boundary portion between the pair of engagement holes sg, sg and the groove bg is formed into the curved shape. In this case, the damage of the artificial posterior cruciate ligament 35 can be suppressed compared with the case that the boundary portion is formed into an edge shape.

The groove bg may not necessarily be provided, as long as the artificial posterior cruciate ligament 35 can be disposed so as not to contact with the inner surface of the medial condyle 11 when one end of the artificial posterior cruciate ligament 35 is hooked on the pair of engagement holes sg, sg.

It is not necessary that the width and depth of the groove bg be kept constant between both ends of the groove bg (that is, between the pair of engagement holes sg, sg), but the width and depth of the groove bg may be change depending on the position. For example, the depth of the groove may increase at both the end of the groove bg, and decrease in the middle between both the end. That is, the bottom of the groove may be formed into a ridge-like curved surface having a vertex in a middle portion. In this case, the damage of the artificial posterior cruciate ligament 35 due to the interference with the inside of the groove bg can be suppressed.

When the pair of engagement holes sg, sg or the groove bg is provided as described above, the artificial posterior cruciate ligament 35 is accommodated in the pair of engagement holes sg, sg or the groove bg, so that the artificial posterior cruciate ligament 35 can be prevented from being detached from the posterior cruciate ligament engagement part 16. That is, when one of or both the pair of engagement holes sg, sg and the groove bg are provided, the pair of engagement holes sg, sg or the groove bg can act as a detachment preventing mechanism.

However, similarly to the engagement part 14, desirably the mechanism (detachment preventing mechanism) that prevents the artificial posterior cruciate ligament 35 from being detached from the posterior cruciate ligament engagement part 16 is provided in the groove 15g in addition to the pair of engagement holes sg, sg and the groove bg. For example, a female screw hole 15n is made between both the ends (a portion, such as the leading end of the posterior cruciate ligament engagement part 16, which is located between the pair of engagement holes sg, sg (see FIG. 24)) of the groove 15g. A male screw member 16n (for example, a set screw in which a male screw is formed in an outer surface) that can be engaged with the female screw hole 15n is provided. In this case, when the male screw member 16n is engaged with the female screw hole 15n, the groove 15g can be separated into two holes by the male screw member 15n. The male screw member 16n is engaged with the female screw hole 15n while one end of the artificial posterior cruciate ligament 35 is disposed so as to pass through the position where one hole in the groove 15g is made from the front surface of the medial condyle inside wall 15 toward the rear surface, and so as to return from the rear surface of the medial condyle inside wall 15 to the front surface through the position where the other hole in the groove 15g is made. Therefore, one end of the artificial posterior cruciate ligament 35 can be prevented from being detached from the posterior cruciate ligament engagement part 16. That is, the detachment preventing mechanism can be constructed with the female screw hole 15n and the male screw member 16n.

In the configuration constructed with the female screw hole 15n and the male screw member 16n, there is no particular limitation to the shape and size of the male screw member 15n. However, desirably the male screw member 15n is the set screw, and the length in the axial direction of the male screw member 15n is substantially equal to the thickness of the posterior cruciate ligament engagement part 16. The use of the set screw can prevent the male screw member 16n from interfering with a peripheral member or a bone even if the male screw member 16n is mounted on the posterior cruciate ligament engagement part 16.

The detachment preventing mechanism is not limited to the configuration constructed with the female screw hole 15n and the male screw member 16n as long as the groove 15g can be separated into the two holes. For example, a rubber member may be pushed in the groove 15g to separate the groove 15g into the two holes.

(Tibia Member 20)

In the artificial knee joint 1B, the tibia member 20 is formed by the combination of the base part 20a and the contact part 20b similarly to the tibia member 20 of the artificial knee joint 1. The base part 20a and contact part 20b of the tibia member 20 of the artificial knee joint 1B are substantially identical to the base part 20a and contact part 20b of the tibia member 20 of the artificial knee joint 1 in the structure, but the base part 20a and contact part 20b of the artificial knee joint 1B differs from the base part 20a and contact part 20b of the artificial knee joint 1 in the notch 20s formed in the rear surface of each of the artificial knee joints. That is, in the artificial knee joint 1B, the notch piercing the base part 20a is not provided, but a coupling member fixing part 20t is provided in the base part 20a. That is, in the tibia member 20 of the artificial knee joint 1B, the coupling member fixing part 20t is provided as if it was the bottom of the notch 20s of the contact part 20b when the notch 20s of the contact part 20b is viewed from above (from the side of the femur F).

(Artificial Posterior Cruciate Ligament 35)

Figure 27:
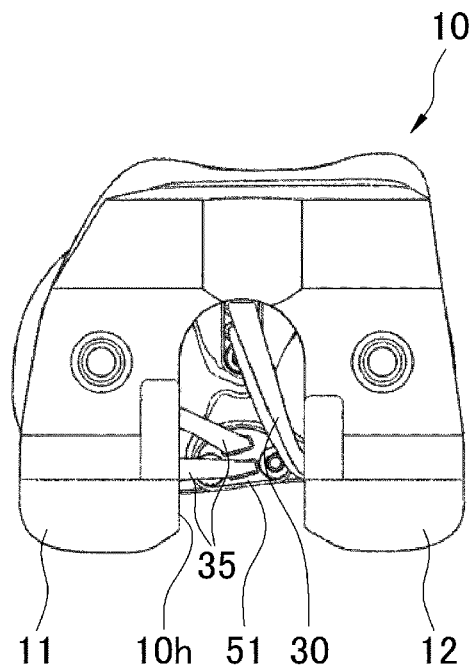
FIGS. 27(A) and 27(B) are plan and bottom views schematically illustrating the ligament reconstruction type artificial knee joint 1B of another embodiment, respectively.
Figure 27:
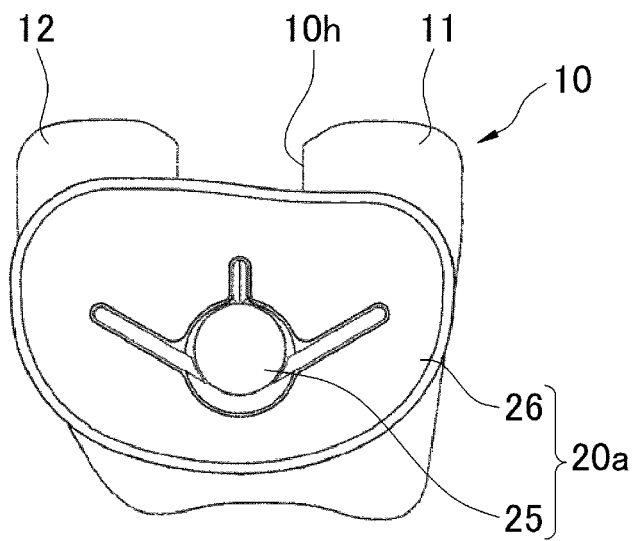
Figure 28:
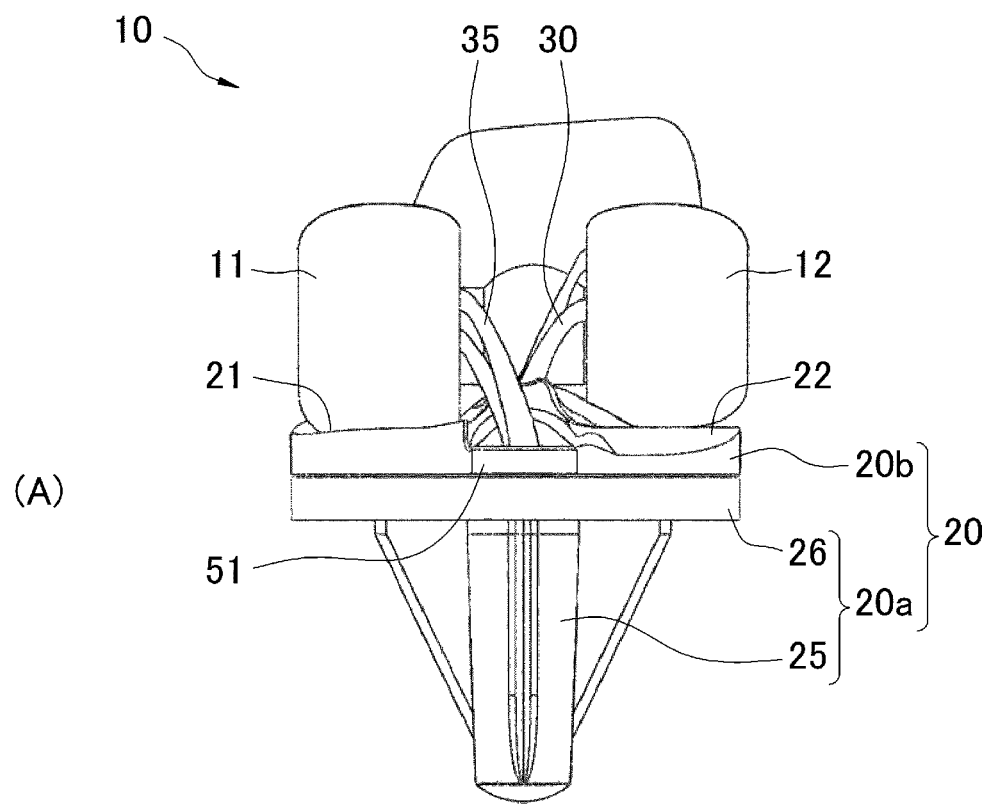
FIGS. 28(A) and 28(B) are rear and right-side views schematically illustrating the ligament reconstruction type artificial knee joint 1B of another embodiment, respectively.
Figure 28:
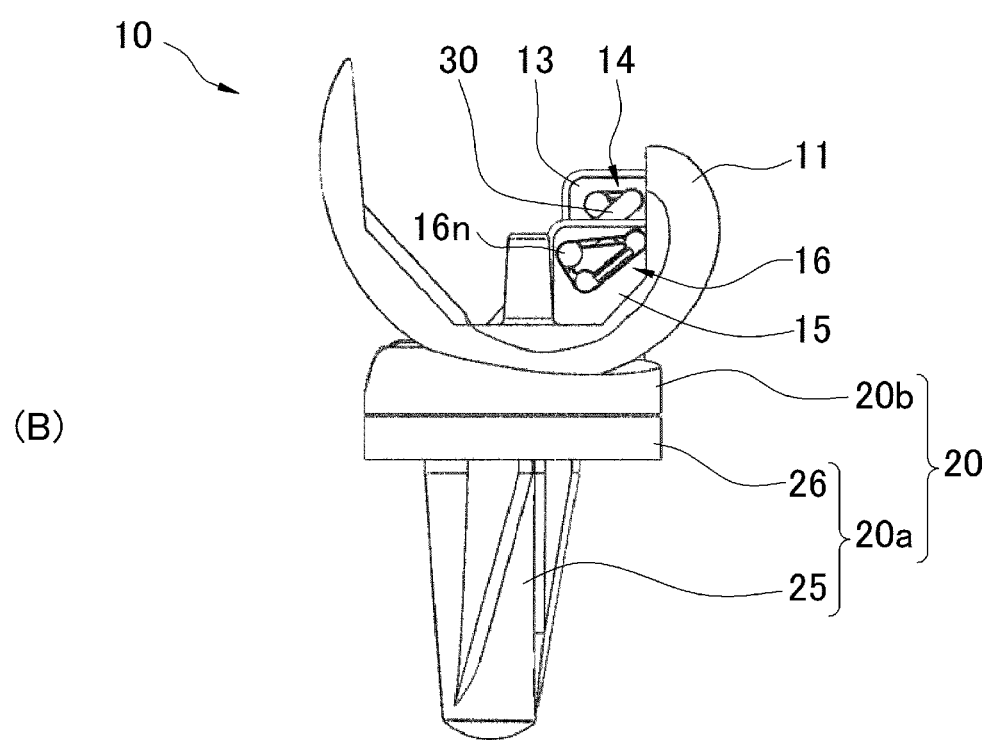
Figure 29:
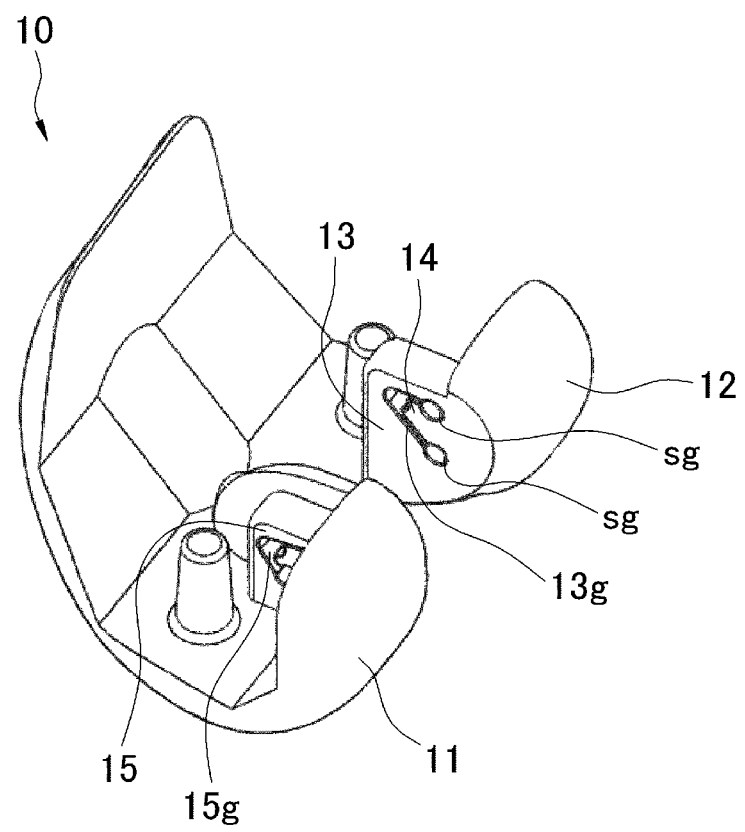
FIG. 29 is a perspective view schematically illustrating the femur member 10 of the ligament reconstruction type artificial knee joint 1B of another embodiment.
Figure 30:
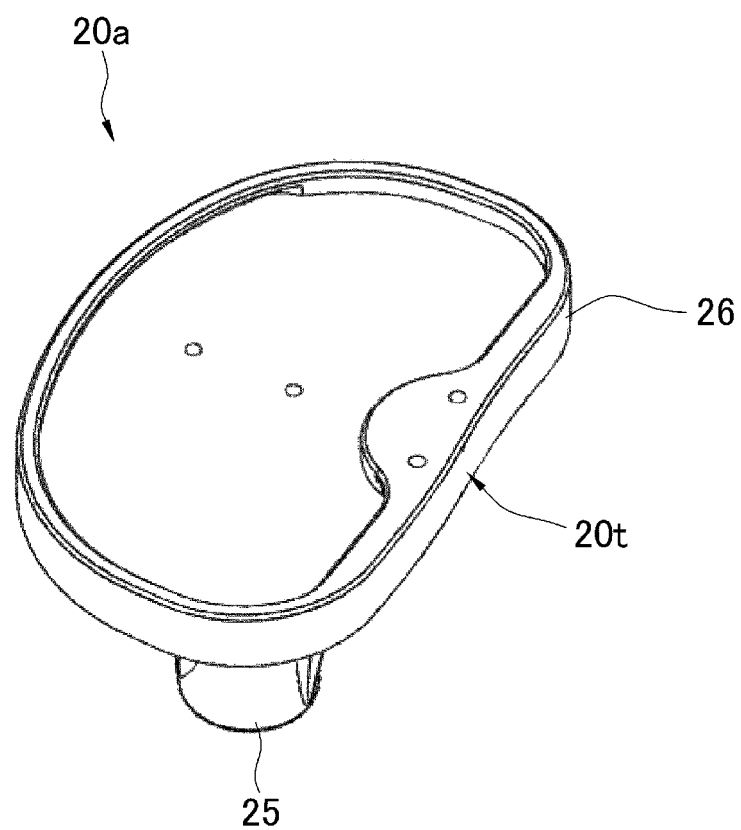
FIG. 30 is a perspective view schematically illustrating a base part 20a in a tibia member 20 of the ligament reconstruction type artificial knee joint 1B of another embodiment.
Figure 31:
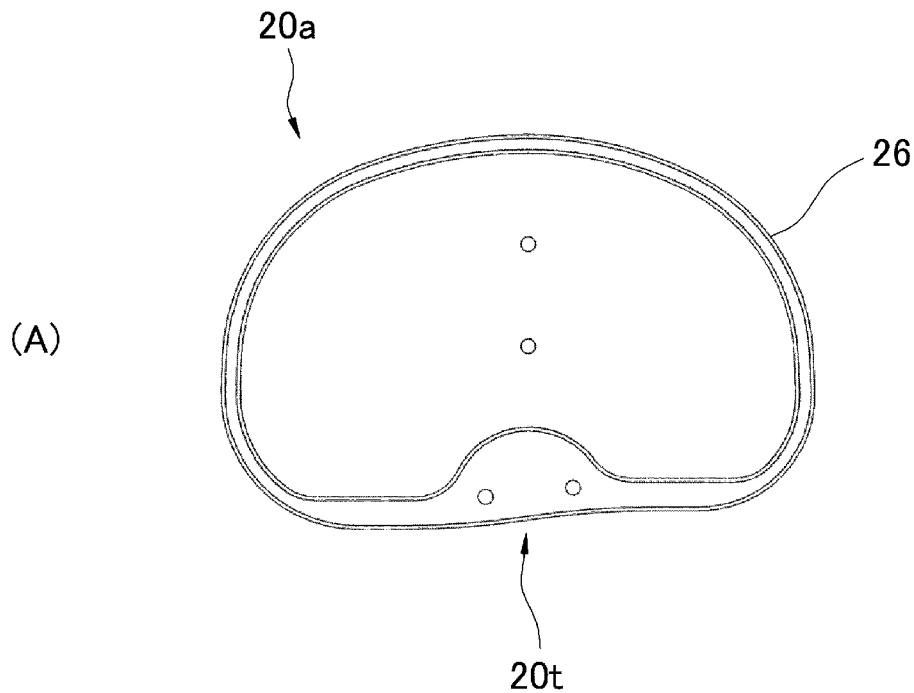
FIGS. 31(A) and 31(B) are plan and bottom views schematically illustrating the base part 20a in the tibia member 20 of the ligament reconstruction type artificial knee joint 1B of another embodiment, respectively.
Figure 31:
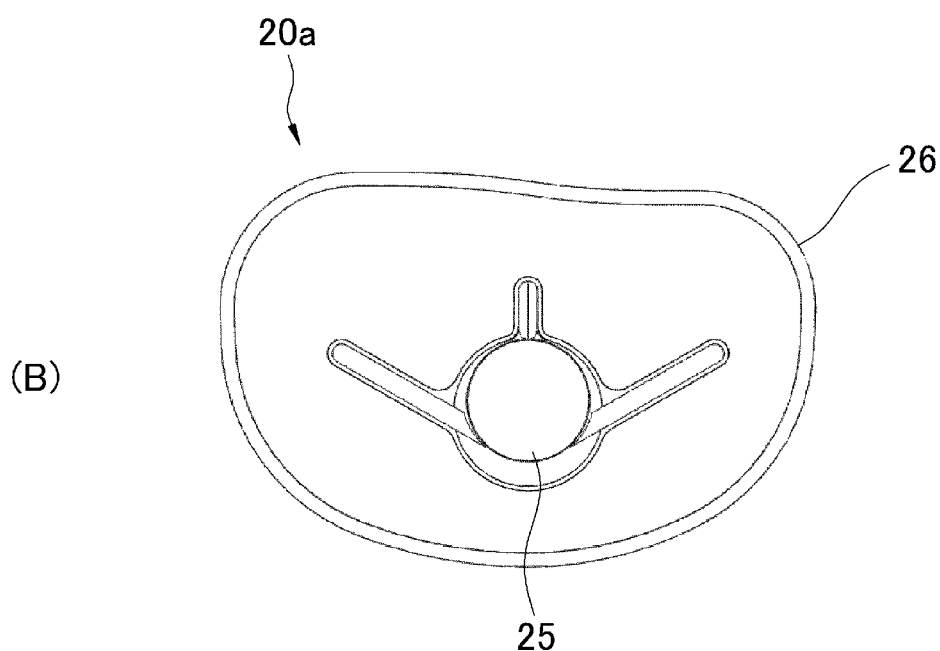

As illustrated in FIGS. 27 and 28, the artificial posterior cruciate ligament 35 is provided between the medial condyle inside wall 15 of the femur member 10 and the contact part 20b of the tibia member 20. The artificial posterior cruciate ligament 35 is a string-shaped member that is artificially made from a material such as polyester similarly to the artificial ligament 30. The artificial posterior cruciate ligament 35 is formed into a ring shape.

One end of the artificial posterior cruciate ligament 35 is engaged with the posterior cruciate ligament engagement part 16 formed in the medial condyle inside wall 15 of the femur member 10. Specifically, the artificial posterior cruciate ligament 35 is hooked on the posterior cruciate ligament engagement part 16 so as to be disposed at the positions of the pair of engagement holes sg, sg of the groove 15g.

The other end of the artificial posterior cruciate ligament 35 is coupled to the posterior cruciate ligament coupling member 51. A section of the posterior cruciate ligament coupling member 51 is formed into the substantially same shape as the coupling member fixing part 20t. Additionally, the posterior cruciate ligament coupling member 51 is disposed such that the front-side face of the posterior cruciate ligament coupling member 51 contacts closely with the rear surface of the notch 20s of the contact part 20b.

The posterior cruciate ligament coupling member 51 includes through-holes at both ends in a longitudinal direction of the posterior cruciate ligament coupling member 51. In other words, the posterior cruciate ligament coupling member 51 includes the through-holes in portions, which are located at both the ends in a width direction of the artificial knee joint 1B when the posterior cruciate ligament coupling member 51 is mounted on the coupling member fixing part 20t. The screws are inserted in the through-holes, which allows the posterior cruciate ligament coupling member 51 to be fixed to the top surface of the coupling member fixing part 20t. Hereinafter, in the posterior cruciate ligament coupling member 51, a direction that is substantially parallel to the width direction of the artificial knee joint 1B of the posterior cruciate ligament coupling member 51 when the posterior cruciate ligament coupling member 51 is mounted on the coupling member fixing part 20t is referred to as a longitudinal direction of the posterior cruciate ligament coupling member 51. A direction orthogonal to the longitudinal direction of the posterior cruciate ligament coupling member 51 is referred to as a width direction of the posterior cruciate ligament coupling member 51.

Figure 32:
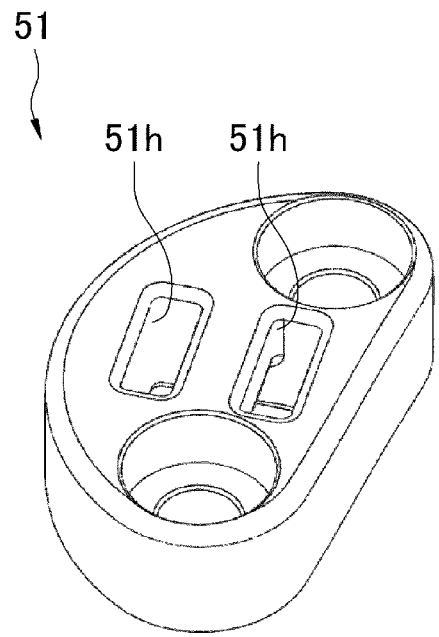
FIGS. 32(A) and 32(B) are perspective and longitudinally sectional views schematically illustrating a posterior cruciate ligament coupling member 51, respectively.
Figure 32:
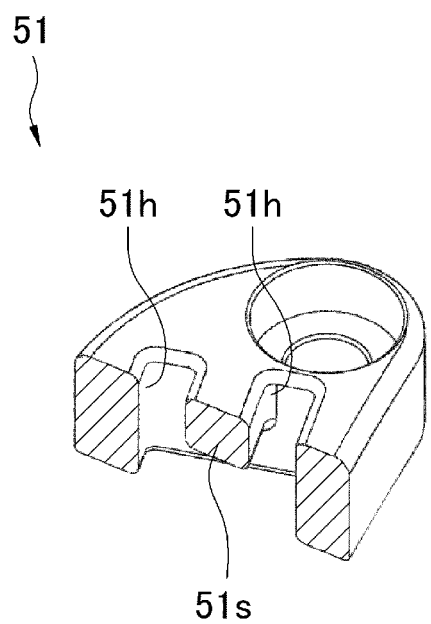
Figure 33:
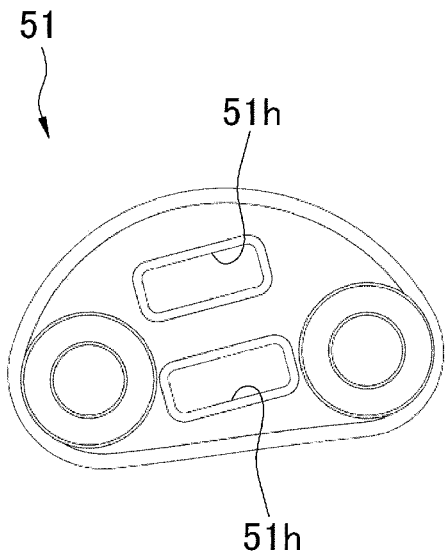
FIGS. 33(A) and 33(B) are plan and bottom views schematically illustrating the posterior cruciate ligament coupling member 51, respectively.
Figure 33:
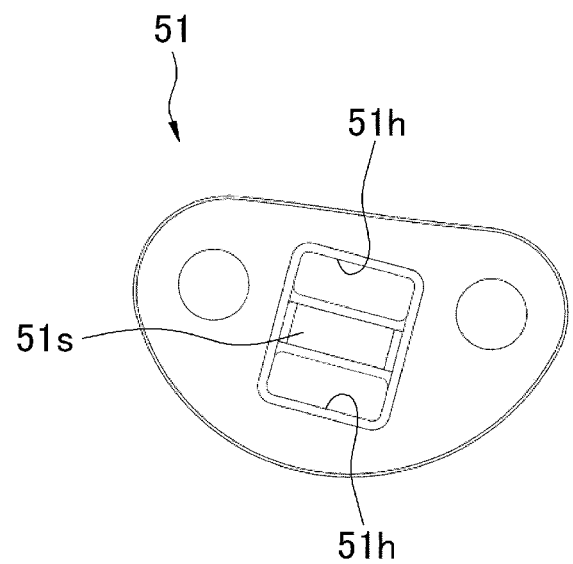
Figure 34:
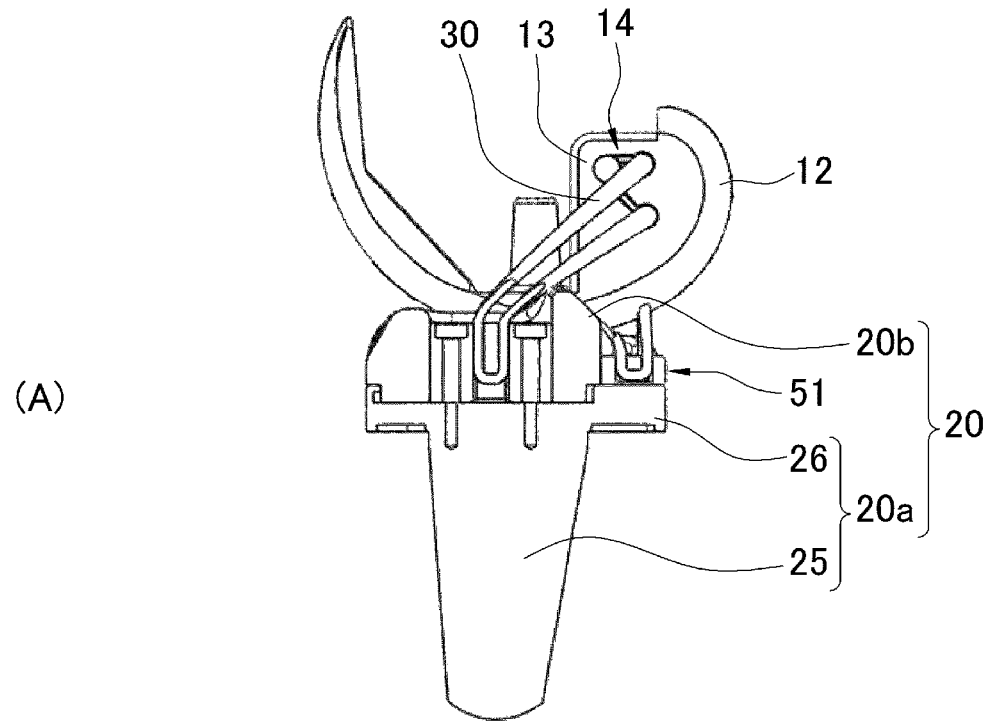
FIGS. 34(A) and 34(B) are left and right sectional views schematically illustrating the ligament reconstruction type artificial knee joint 1B of another embodiment, respectively.
Figure 34:
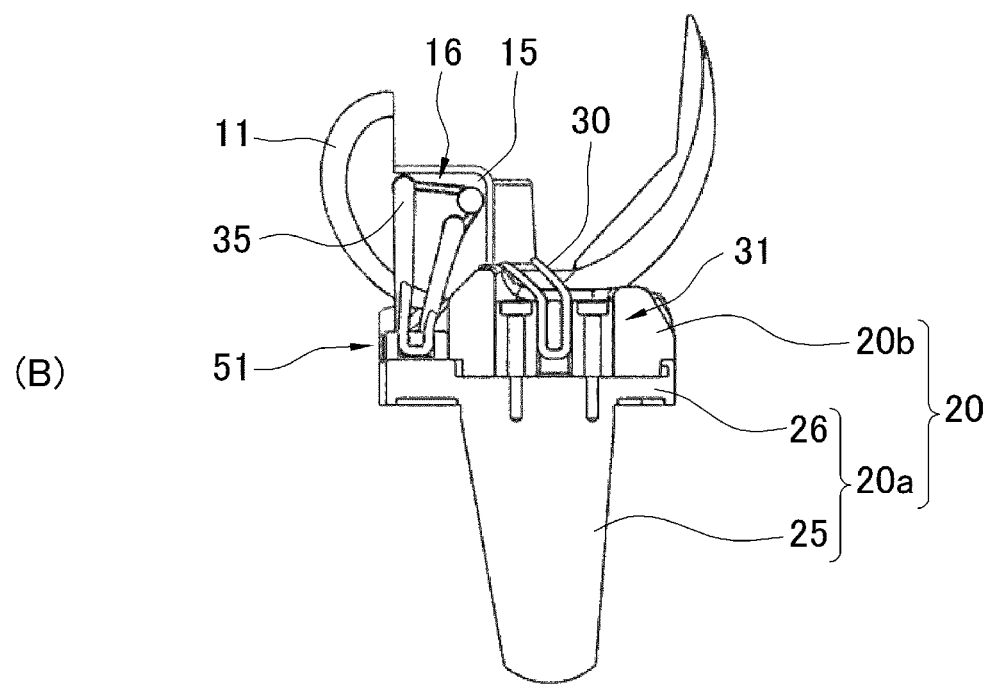
Figure 35:
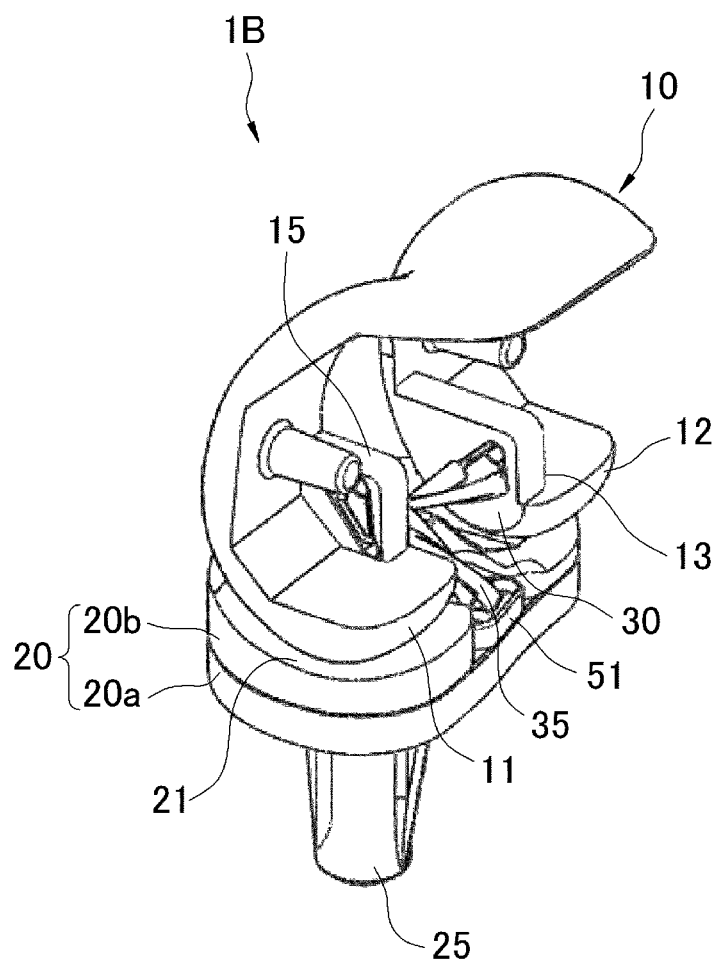
FIG. 35 is a perspective view schematically illustrating a state in which the ligament reconstruction type artificial knee joint 1B of another embodiment is bent by 90 degrees.
Figure 36:
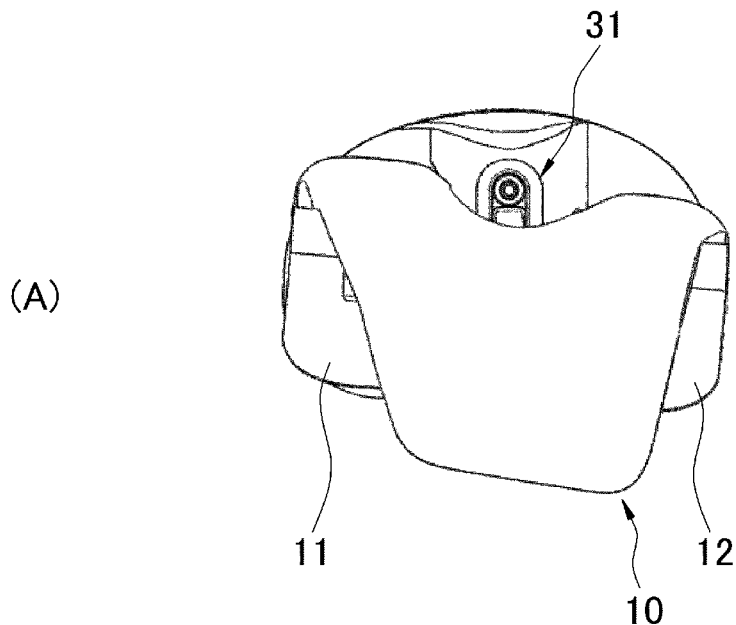
FIGS. 36(A) and 36(B) are plan and bottom views schematically illustrating the state in which the ligament reconstruction type artificial knee joint 1B of another embodiment is bent by 90 degrees, respectively.
Figure 36:
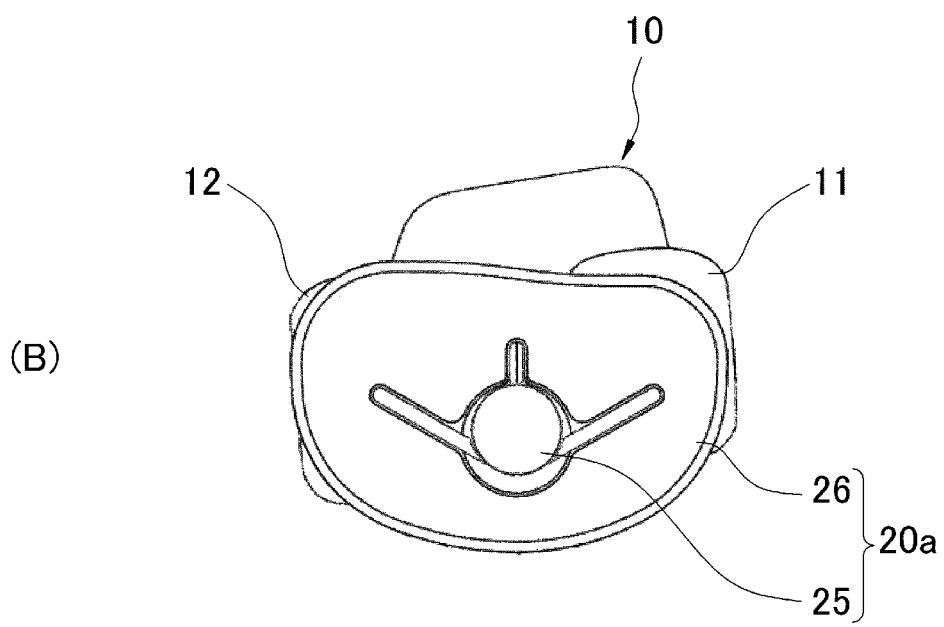
Figure 37:
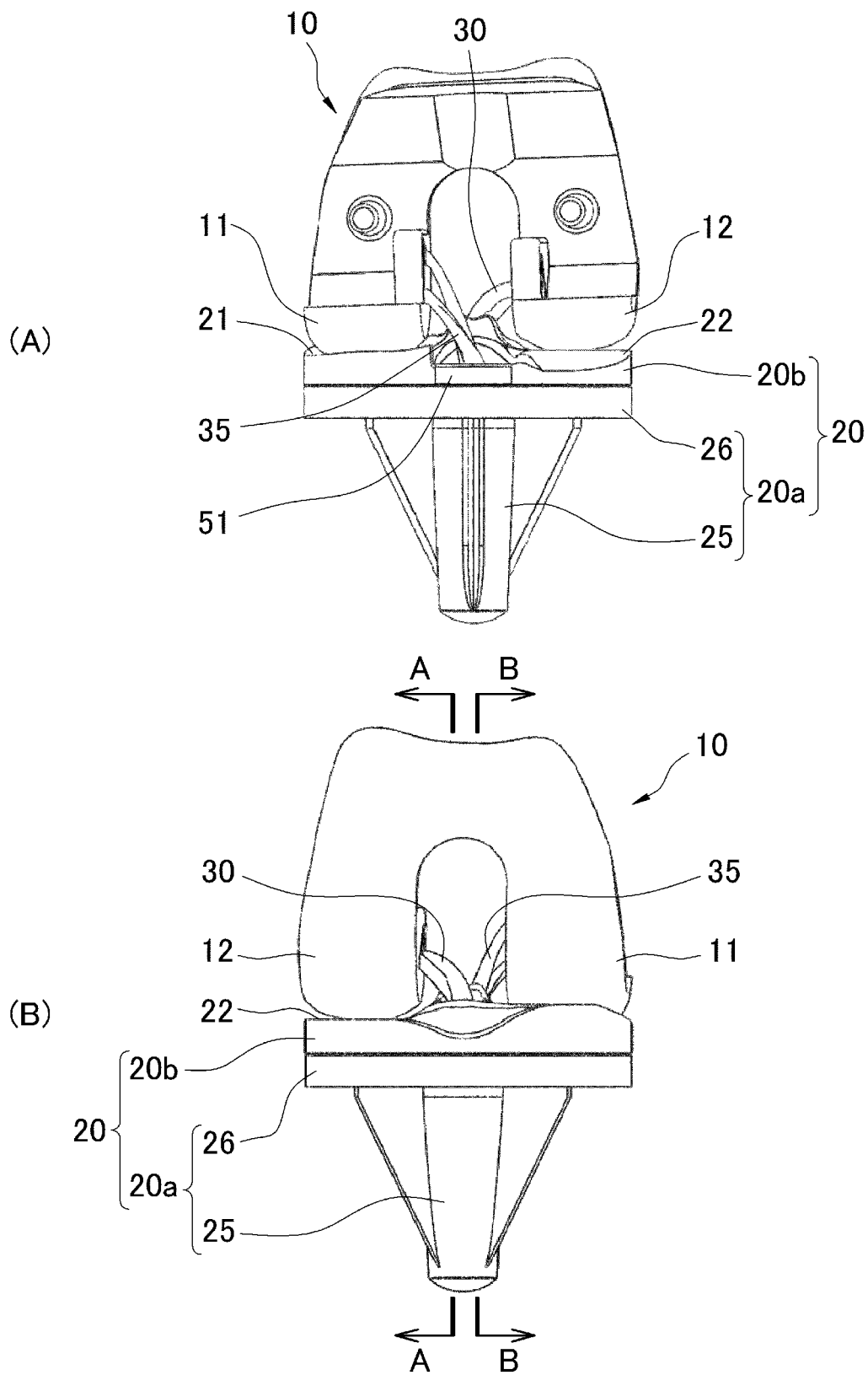
FIGS. 37(A) and 37(B) are rear and front views schematically illustrating the state in which the ligament reconstruction type artificial knee joint 1B of another embodiment is bent by 90 degrees, respectively.
Figure 38:
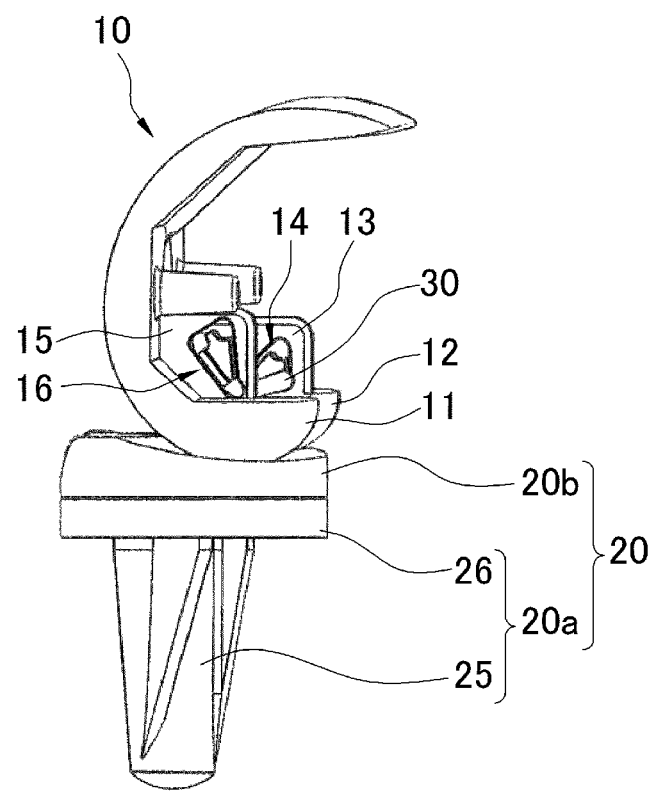
FIGS. 38(A) and 38(B) are right and left side views schematically illustrating the state in which the ligament reconstruction type artificial knee joint 1B of another embodiment is bent by 90 degrees, respectively.
Figure 38:
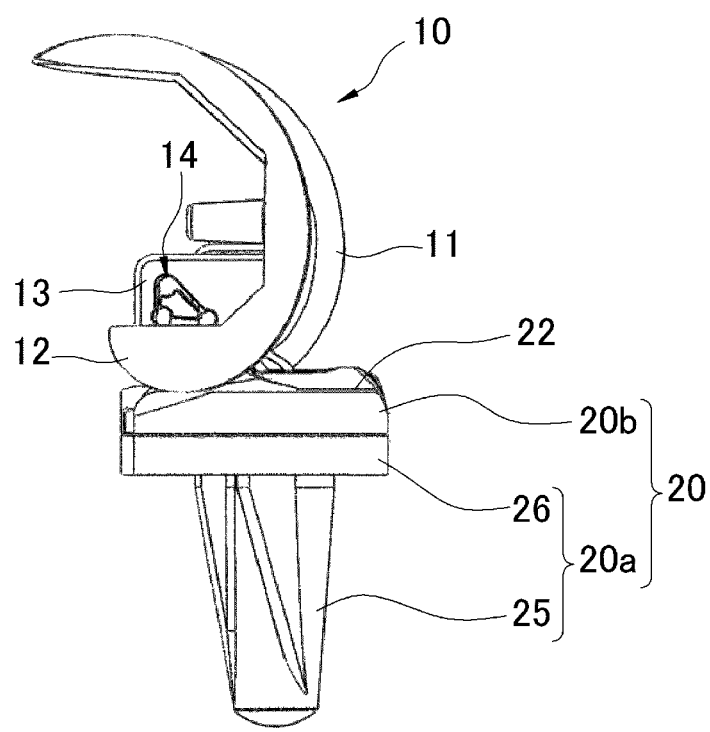
Figure 39:
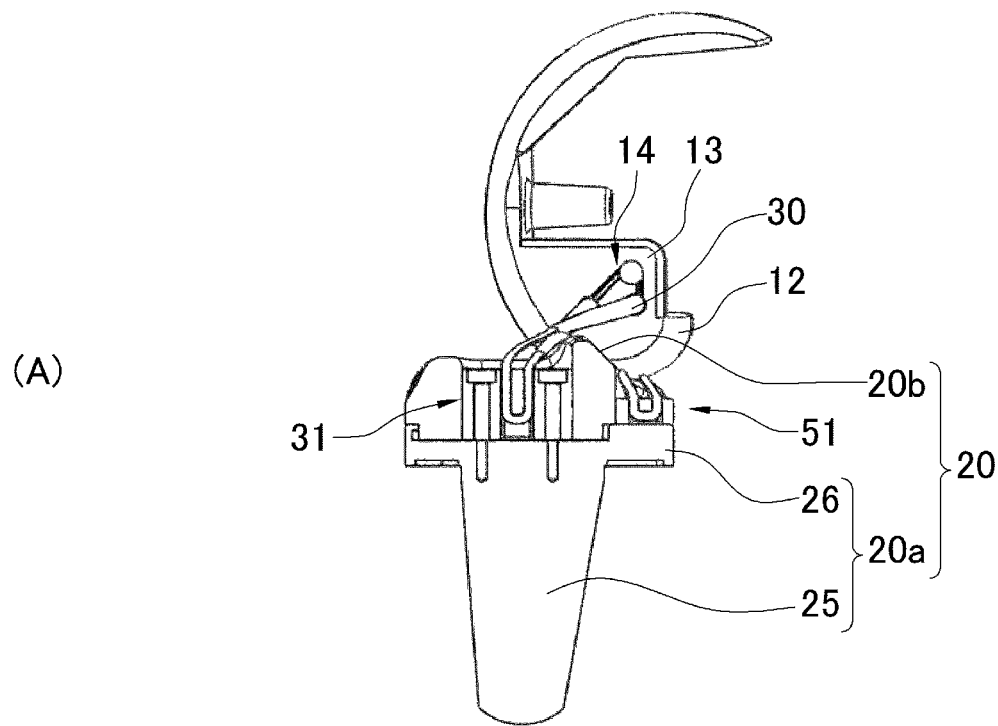
FIG. 39(A) is a sectional view taken along a line A-A in FIG. 37(B)
FIG. 39(B) is a sectional view taken along a line B-B in FIG. 37(B).
Figure 39:
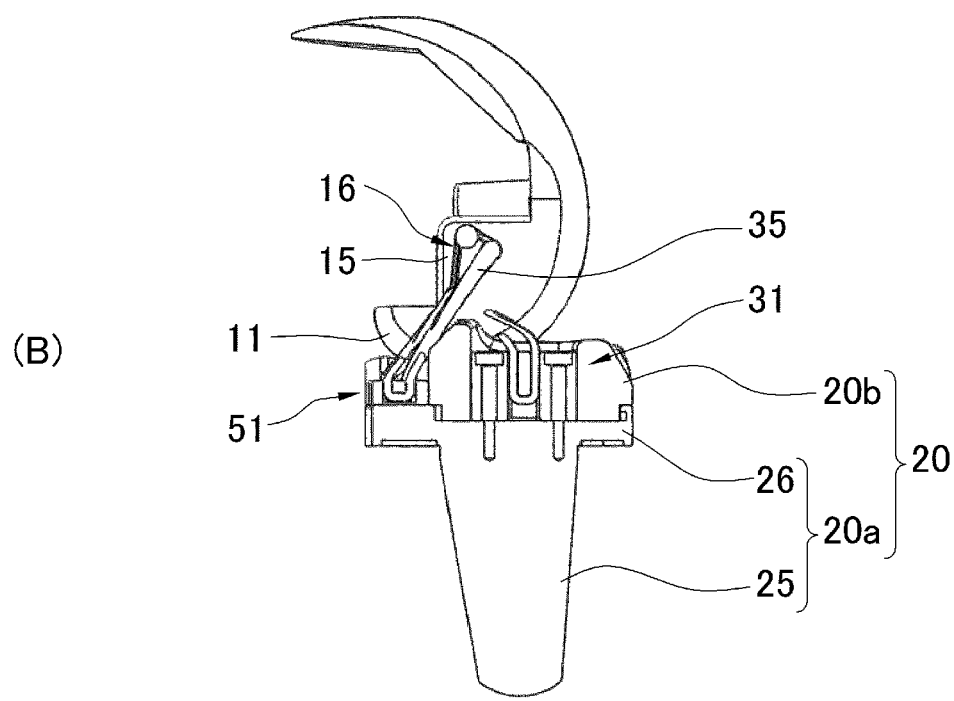

As illustrated in FIGS. 32 and 33, in the posterior cruciate ligament coupling member 51, a pair of through-holes 51h, 51h vertically piercing the posterior cruciate ligament coupling member 51 are made in addition to the through-holes in which the screws are inserted. The pair of through-holes 51h, 51h are made so as to be arrayed along the direction orthogonal to the longitudinal direction of the posterior cruciate ligament coupling member 51, namely, the width direction of the posterior cruciate ligament coupling member 51. In other words, the pair of through-holes 51h, 51h is provided so as to be arrayed in the posterior and anterior direction of the artificial knee joint 1B when the posterior cruciate ligament coupling member 51 is mounted on the coupling member fixing part 20t. That is, the posterior cruciate ligament coupling member 51 has a structure, in which the artificial posterior cruciate ligament 35 can be hooked on a beam portion 51s between the through-holes 51h, 51h when the artificial posterior cruciate ligament 35 is inserted in the pair of through-holes 51h, 51h. A space in which the artificial posterior cruciate ligament 35 is accommodated is provided in a lower portion of the beam portion 51s such that the artificial posterior cruciate ligament 35 does not pop out from the bottom surface of the posterior cruciate ligament coupling member 51.

Therefore, in the above configuration, the artificial posterior cruciate ligament 35 can be provided so as to couple the femur member 10 to the tibia member 20. That is, one end of the artificial posterior cruciate ligament 35 is hooked on the posterior cruciate ligament engagement part 16. The other end of the artificial posterior cruciate ligament 35 is coupled to (engaged with) the posterior cruciate ligament coupling member 51, and the posterior cruciate ligament coupling member 51 is disposed in the notch 20s of the contact part 20b. When the posterior cruciate ligament coupling member 51 is fixed to the top surface of the coupling member fixing part 20t, the artificial posterior cruciate ligament 35 can be provided so as to couple the femur member 10 to the tibia member 20. The posterior cruciate ligament coupling member 51 is disposed in the notch 20s of the contact part 20b, the posterior cruciate ligament coupling member 51 is fixed to the top surface of the coupling member fixing part 20t, and the other end of the artificial posterior cruciate ligament 35 is fixed to the tibia member 20. Hereinafter, sometimes this is referred to as "the other end of the artificial posterior cruciate ligament 35 is coupled to the notch 20s".

The posterior cruciate ligament engagement part 16 is formed at the position where the original posterior cruciate ligament PCL and the distal end DT of the original femur F are coupled together when the femur member 10 is mounted on the distal end DT of the femur F. The notch 20s is formed at the position through which the original posterior cruciate ligament PCL passes when the tibia member 20 is mounted on the proximal end PE of the tibia E. Therefore, when both the ends of the artificial posterior cruciate ligament 35 are coupled to the posterior cruciate ligament engagement part 16 and the notch 20s, the artificial ligament 30 is disposed at the position of the original posterior cruciate ligament PCL. That is, the artificial posterior cruciate ligament 35 can be disposed at the position where once the posterior cruciate ligament PCL is disposed in the knee joint replaced for the artificial knee joint.

Because of the above configuration, when the knee joint is replaced for the artificial knee joint 1B of another embodiment, the posterior cruciate ligament PCL can be reconstructed, and the artificial posterior cruciate ligament 35 can be provided at the same position as the posterior cruciate ligament PCL in the original knee.

According to the artificial knee joint 1B of another embodiment, not only the artificial ligament 30 acts as the anterior cruciate ligament (healthy ligament) in the knee before being replaced for the artificial knee joint 1B, but also the artificial posterior cruciate ligament 35 can substantially act as the posterior cruciate ligament (healthy ligament) in the knee before being replaced with the artificial knee joint 1B.

Additionally, the artificial posterior cruciate ligament 35 is formed into the ring shape, one end of the artificial posterior cruciate ligament 35 is engaged with the pair of engagement holes sg, sg arrayed in the posterior and anterior direction of the knee, and the other end is engaged with the pair of through-holes 51h, 51h arrayed in the posterior and anterior direction of the knee in the posterior cruciate ligament coupling member 51. Therefore, in bending and stretching the knee, the twist can be generated in the artificial posterior cruciate ligament 35 in association with the knee joint bending and stretching motion (see FIGS. 37 and 39). The movement of the artificial posterior cruciate ligament 35 can be brought closer to that of the healthy ligament in bending and stretching the knee. The twist generated in the artificial posterior cruciate ligament 35 or the distance between both the ends of the artificial posterior cruciate ligament 35 changes depending on the bent and stretched status of the knee and the tensile force generated in the artificial ligament 35 changes, so that the tensile force generated in the artificial ligament 35 can be brought close to that generated by the healthy ligament.

In the above example, the artificial posterior cruciate ligament 35 has the ring shape. However, the artificial posterior cruciate ligament 35 may not necessarily have the ring shape. That is, both the ends of the artificial posterior cruciate ligament 35 are formed into the ring shape but a portion between the ends may have the simple string shape. Even in this case, when the artificial posterior cruciate ligament 35 is provided such that the twist or the tensile force is generated in the string-shaped portion in association with the knee joint bending and stretching motion, the movement of the artificial posterior cruciate ligament 35 can be brought close to that of the healthy posterior cruciate ligament in bending and stretching the knee.

(Mounting Example of Artificial Knee Joint 1B of another Embodiment)

Work to mount the artificial knee joint 1B of another embodiment will be described below.

The description in mounting the artificial knee joint 1B including only the artificial ligament 30 is properly omitted.

As to the knee on which the artificial knee joint 1B is mounted, the distal end DT of the femur F and the proximal end PE of the tibia T are partially cut off, and formed into the shapes on which the femur member 10 and the base part 20a of the tibia member 20 can be mounted. At this time, the anterior cruciate ligament ACL and the posterior cruciate ligament PCL, which connect the distal end DT of the femur F and the proximal end PE of the tibia T, are cut off.

Then the femur member 10 is mounted so as to cover the distal end DT of the femur F. Therefore, at the distal end DT of the femur F, the medial condyle MC and lateral condyle LC of the femur Fare covered with the medial condyle 11 and lateral condyle 12 of the femur member 10.

One end of the artificial ligament 30 is previously hooked on the engagement part 14 before the femur member 10 is mounted on the distal end DT of the femur F. The coupling member 31 is previously mounted on the other end of the artificial ligament 30.

Similarly, one end of the artificial posterior cruciate ligament 35 is previously hooked on the posterior cruciate ligament engagement part 16 before the femur member 10 is mounted on the distal end DT of the femur F. The posterior cruciate ligament coupling member 51 is also previously mounted on the other end of the artificial posterior cruciate ligament 35.

(Mounting of Artificial Ligament 30)

In the artificial ligament 30 and the artificial posterior cruciate ligament 35, since the other end of the artificial posterior cruciate ligament 35 is located on the outside (rear side), the artificial ligament 30 is mounted first. Specifically, the coupling member 31 engaged with the other end of the artificial ligament 30 is inserted in the fixing hole 20h of the contact part 20b of the tibia member 20. When the coupling member 31 is fixed to the base plate 26 of the base part 20a using a screw, the femur member 10 and the tibia member 20 are coupled together by the artificial ligament 30. That is, the artificial ligament 30 can be disposed at the position where once the anterior cruciate ligament ACL is disposed in the knee joint replaced for the artificial knee joint 1B.

(Mounting of Artificial Posterior Cruciate Ligament 35)

The artificial posterior cruciate ligament 35 is mounted when the artificial ligament 30 is mounted. Specifically, the posterior cruciate ligament coupling member 51 engaged with the other end of the artificial posterior cruciate ligament 35 is disposed in the notch 20s of the tibia member 20. At this time, the posterior cruciate ligament coupling member 51 is disposed such that the front-side face of the posterior cruciate ligament coupling member 51 contacts closely with the rear surface of the notch 20s of the contact part 20b. The posterior cruciate ligament coupling member 51 is fixed to the coupling member fixing part 20t using a screw. Therefore, the femur member 10 and the tibia member 20 are coupled together by not only the artificial ligament 30 but also the artificial posterior cruciate ligament 35. The posterior cruciate ligament engagement part 16 is formed so as to be disposed at the position where the original posterior cruciate ligament PCL and the distal end DT of the original femur F are coupled together when the femur member 10 is mounted on the distal end DT of the femur F. The notch 20s is formed so as to be disposed at the position where the original posterior cruciate ligament PCL and the original tibia E are coupled together when the tibia member 20 is mounted on the proximal end PE of the tibia E. Accordingly, the artificial posterior cruciate ligament 35 can be disposed at the position where once the posterior cruciate ligament PCL is disposed in the knee joint replaced for the artificial knee joint 1B.

As described above, one end of the artificial ligament 30 is engaged with the engagement part 14, and the coupling member 31 engaged with the other end of the artificial ligament 30 is fixedly inserted in the fixing hole 20h of the contact part 20b of the tibia member 20, so that the artificial ligament 30 can be mounted so as to couple the femur member 10 and the tibia member 20.

Similarly, one end of the artificial posterior cruciate ligament 35 is engaged with the posterior cruciate ligament engagement part 16, and the posterior cruciate ligament coupling member 51 engaged with the other end of the artificial posterior cruciate ligament 35 is fixedly disposed in the notch 20s of the tibia member 20, so that the artificial posterior cruciate ligament 35 can be mounted so as to couple the femur member 10 and the tibia member 20.

Accordingly, the medical treatment time can be shortened even if both the artificial ligament 30 and the artificial posterior cruciate ligament 35 are mounted.

The artificial ligament 30 and the artificial posterior cruciate ligament 35 are disposed at the positions where once the anterior cruciate ligament ACL and the posterior cruciate ligament PCL exist in the knee replaced for the artificial knee joint 1B, so that the relative position between the artificial ligament 30 and the artificial posterior cruciate ligament 35 can be brought close to that of the original knee.

When the mounting states of the artificial ligament 30 and artificial posterior cruciate ligament 35 are adjusted, the tensile force generated in each ligament can be adjusted to the proper state. Not only the relative position between the artificial ligament 30 and the artificial posterior cruciate ligament 35 but also the relative force relationship between the artificial ligament 30 and the artificial posterior cruciate ligament 35 can be brought close to those of the original knee.

The adjustment of the tensile force generated in the artificial ligament 30 or artificial posterior cruciate ligament 35 can be performed by the following method. The case that the coupling member 31 or the posterior cruciate ligament coupling member 51 is screwed to the top surface of the base plate 26 or coupling member fixing part 20t is considered by way of example. In this case, the tensile force generated in the artificial ligament 30 or artificial posterior cruciate ligament 35 can be adjusted by changing the screw tightening state. When the height of the coupling member 31 or posterior cruciate ligament coupling member 51 can be adjusted, the tensile force generated in the artificial ligament 30 or artificial posterior cruciate ligament 35 can be adjusted even in the same screw tightening state. For example, a spacer is provided between the top surface of the base plate 26 and the coupling member 31 or between the top surface of the coupling member fixing part 20t and the posterior cruciate ligament coupling member 51. Therefore, the position (that is, the position relative to the contact part 20b) of the top surface of the coupling member 31 or posterior cruciate ligament coupling member 51 is adjusted by the spacer, so that the tensile force generated in the artificial ligament 30 or artificial posterior cruciate ligament 35 can be adjusted even in the same screw tightening state.

The engagement part 14 and the opening of the fixing hole 20h are formed at the position where once the anterior cruciate ligament ACL is coupled to the distal end DT of the femur F in the knee replaced for the artificial knee joint 1B and the position where once the tibia member 20 is coupled to the proximal end PE of the tibia E in the knee replaced for the artificial knee joint 1B, respectively. However, there is no particular limitation to a method for deciding the position where the engagement part 14 or the opening of the fixing hole 20h. The method described in mounting the artificial knee joint 1B including only the artificial ligament 30 acting as the anterior cruciate ligament ACL can be adopted.

The posterior cruciate ligament engagement part 16 is formed at the position where once the posterior cruciate ligament PCL is coupled to the distal end DT of the femur F in the knee replaced for the artificial knee joint 1B, and the notch 20s is formed at the position where once the posterior cruciate ligament PCL is disposed in the knee replaced for the artificial knee joint 1B. However, there is no particular limitation to a method for deciding the position to which the posterior cruciate ligament engagement part 16 is coupled or the position where the notch 20s is provided. For example, the position of the posterior cruciate ligament PCL of a person on whom the artificial knee joint 1B is mounted is previously checked, and the position where the posterior cruciate ligament engagement part 16 or the notch 20s is provided may be decided based on the check. The positions of the posterior cruciate ligaments PCL of plural persons are measured, and the position where the posterior cruciate ligament engagement part 16 or the notch 20s is provided may statistically be decided. For example, as illustrated in FIG. 40, a shallow/deep direction and a high/low direction from a front-side surface are defined in the femur member 10. In the engagement holes sg, sg of the posterior cruciate ligament engagement part 16, the front engagement hole sg is referred to as a hole A, and the rear engagement hole sg is referred to as a hole B. The posterior cruciate ligament engagement part 16 is provided such that, when the femur member 10 is mounted on the distal end DT of the femur F, one end of the artificial posterior cruciate ligament 35 is disposed in the hole A located ranging from about 15% to about 50% and the hole B located ranging from about 30% to about 75% in the shallow/deep direction, and in the hole A located ranging from about 0% to about 35% and the hole B located ranging from about 25% to about 70% in the high/low direction. The notch 20s is formed such that the other end of the artificial posterior cruciate ligament 35 is disposed at the position ranging from about 0% to about 10% from the center of the right and left direction in the top surface of the contact part 20b of the tibia member 20. Therefore, when the artificial posterior cruciate ligament 35 is simply mounted by the above method, the artificial posterior cruciate ligament 35 can be disposed at the substantially same position as the position of the original posterior cruciate ligament PCL of the person on whom the artificial knee joint 1B is mounted.

(Another Example in which Artificial Ligament 30 is Twisted)

The method for putting the ring-shaped artificial ligament 30 in the twisted state between the engagement part 14 and the fixing hole 20h is not limited to the above configuration. In the above example, the pair of engagement holes sg, sg is made in the engagement part 14 so as to be vertically separated from each other, and the pair of through-holes 31h, 31h of the coupling member 31 is made so as to be arrayed in the posterior and anterior direction. Alternatively, even if the pair of through-holes 31h, 31h of the coupling member 31 is made so as to be arrayed in the right and left direction, the ring-shaped artificial ligament 30 can be put in the twisted state between the engagement part 14 and the fixing hole 20h. Alternatively, the pair of engagement holes sg, sg is made so as to be separated from each other in the posterior and anterior direction, and the pair of through-holes 31h, 31h of the coupling member 31 is made so as to be arrayed in the right and left direction. Even in this case, the ring-shaped artificial ligament 30 can be put in the twisted state between the engagement part 14 and the fixing hole 20h. That is, the direction in which the pair of engagement holes sg, sg is arrayed only has to be non-parallel to the direction in which the pair of through-holes 31h, 31h of the coupling member 31 is arrayed. When the direction in which the pair of engagement holes sg, sg is arrayed is non-parallel to the direction in which the pair of through-holes 31h, 31h of the coupling member 31 is arrayed, the ring-shaped artificial ligament 30 can be put in the twisted state between the engagement part 14 and the fixing hole 20h.

(Another Example in which Artificial Posterior Cruciate Ligament 35 is Twisted)

Similarly, in the case that the ring-shaped artificial posterior cruciate ligament 35 is mounted while twisted between the posterior cruciate ligament engagement part 15 and the notch 20s, there is no particular limitation to the method for twisting the artificial posterior cruciate ligament 35. Like the above example, the pair of engagement holes sg, sg is made in the posterior cruciate ligament engagement part 15 such that the pair of engagement holes sg, sg is separated from each other along the posterior and anterior direction while differing slightly from each other in the height, and the pair of through-holes 51h, 51h of the posterior cruciate ligament coupling member 51 is disposed so as to be arrayed in the posterior and anterior direction. Even in this case, the twist is slightly generated in the artificial posterior cruciate ligament 35. Alternatively, the pair of through-holes 51h, 51h of the posterior cruciate ligament coupling member 51 is disposed so as to be arrayed in the right and left direction. Even in this case, the ring-shaped artificial posterior cruciate ligament 35 can be put in the twisted state between the posterior cruciate ligament engagement part 15 and the notch 20s. That is, when the direction in which the pair of engagement holes sg, sg is arrayed is non-parallel to the direction in which the pair of through-holes 51h, 51h of the posterior cruciate ligament coupling member 51 is arrayed, the ring-shaped artificial posterior cruciate ligament 35 can be put in the twisted state between the posterior cruciate ligament engagement part 15 and the notch 20s.

(Another Example of Coupling Member 31)

The coupling member 31 including the pair of through-holes 31h, 31h is described in the above example. However, the coupling member 31 only has to have the structure in which the other end of the ring-shaped artificial ligament 30 is coupled or engaged, but there is no particular limitation to the structure. For example, structures in FIGS. 21 to 23 may be adopted.

Figure 21:
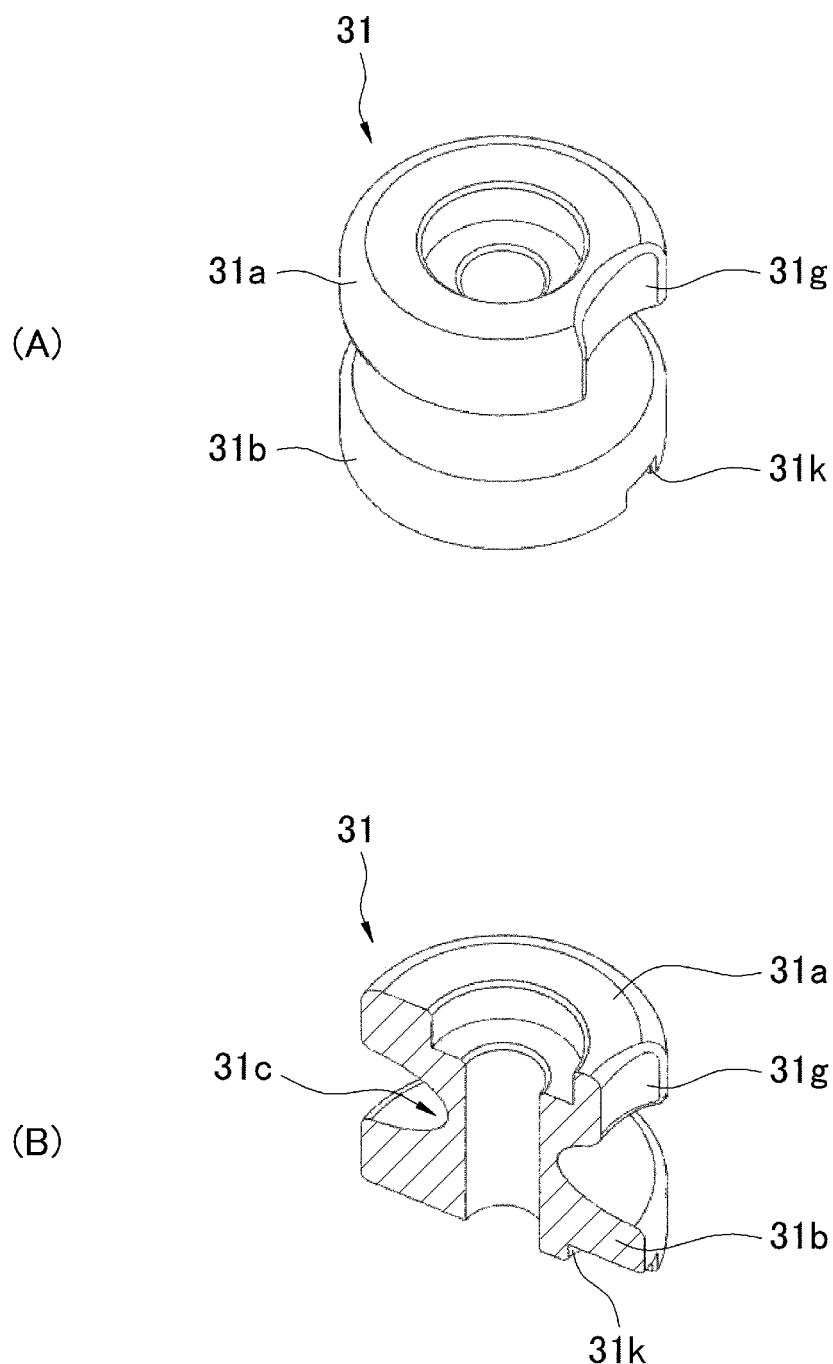
FIGS. 21(A) and 21(B) are perspective and longitudinally sectional views schematically illustrating a coupling member 31 of another embodiment, respectively.
Figure 22:
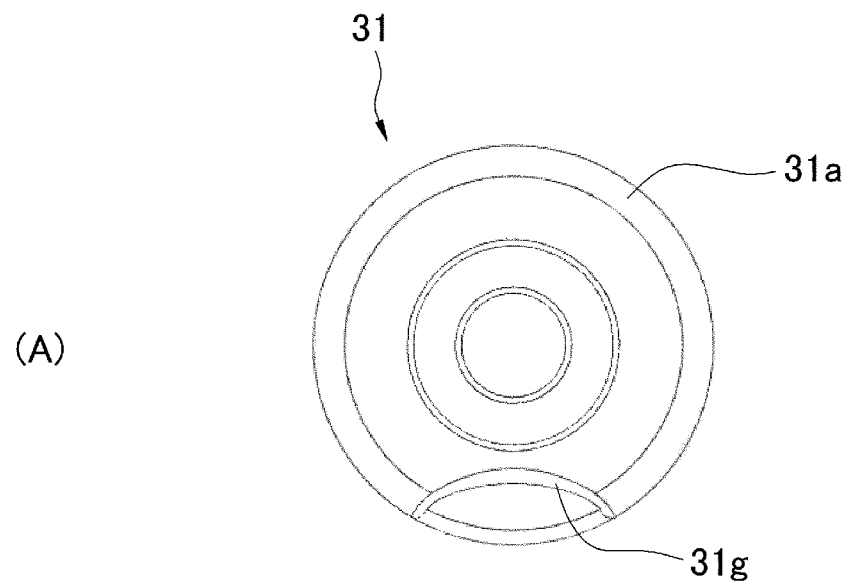
FIGS. 22(A) and 22(B) are plan and bottom views schematically illustrating the coupling member 31 of another embodiment, respectively.
Figure 22:
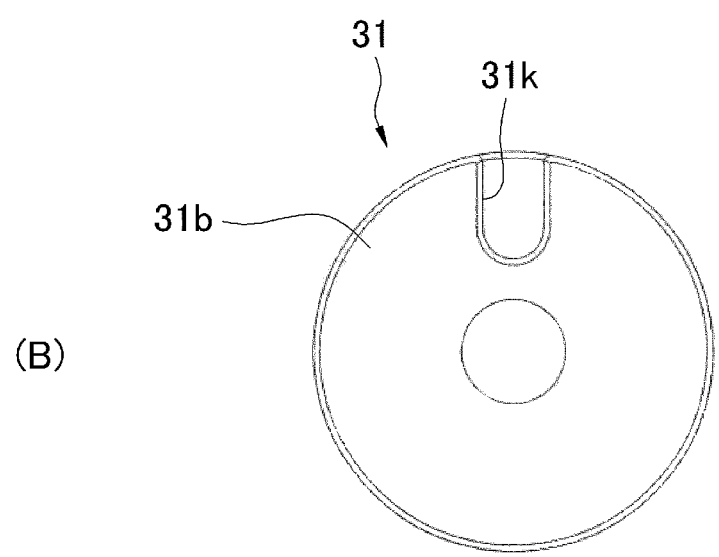
Figure 23:
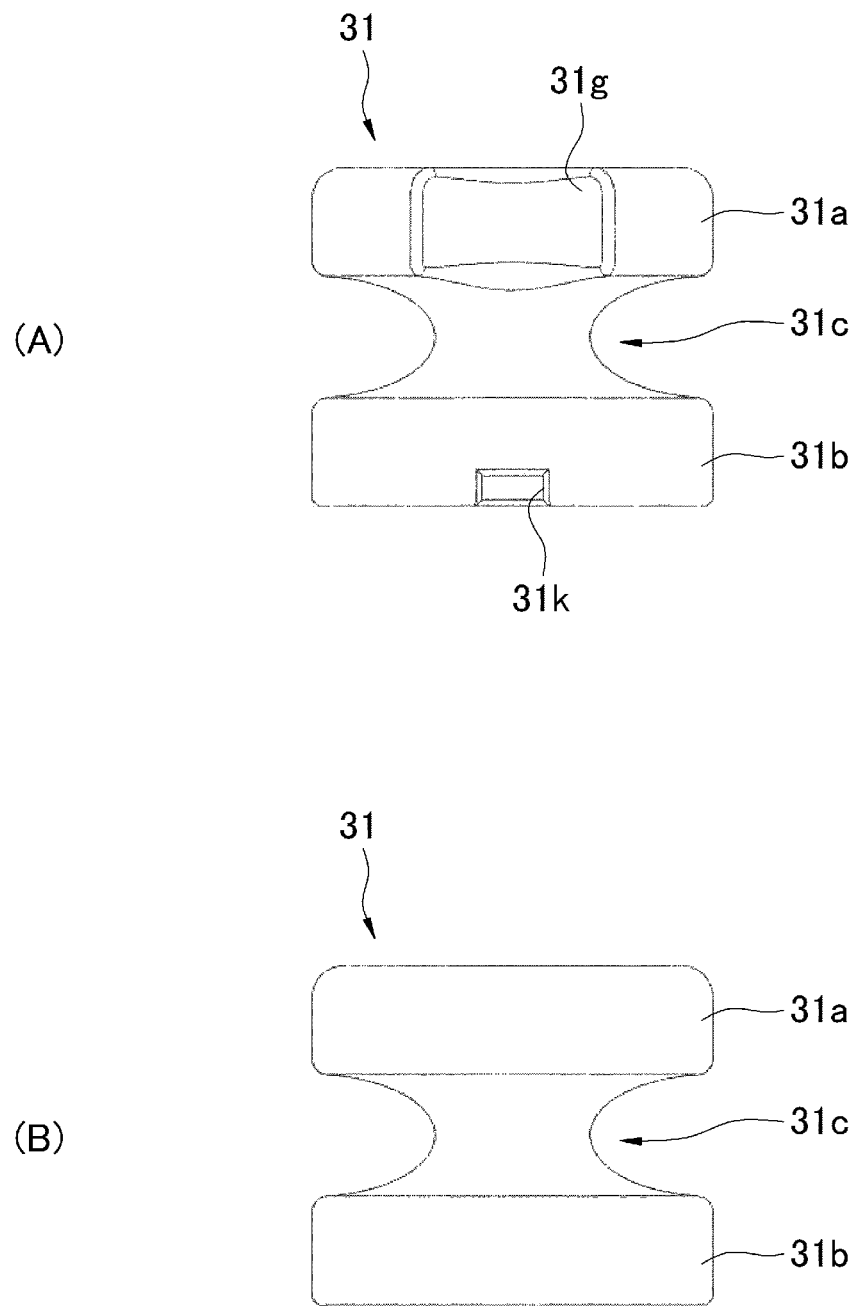
FIGS. 23(A) and 23(B) are front and rear views schematically illustrating the coupling member 31 of another embodiment, respectively.

In FIGS. 21 to 23, the coupling member 31 is formed into a hand drum shape having a substantially circular shape in section. As used herein, the hand drum shape means one in which a diameter of a central portion in an axial direction is smaller than a diameter of each of both ends in the axial direction. That is, the coupling member 31 includes enlarged-diameter parts 31a, 31b at both ends of the coupling member 31 and a narrow part 31c between the enlarged-diameter parts 31a, 31b. The narrow part 31c is one on which the other end of the artificial ligament 30 is hooked.

A notch 31g is provided in a side surface of the enlarged-diameter part (in FIGS. 21 and 23, the enlarged-diameter part 31a), which is located on the upper side when the coupling member 31 is mounted in the fixing hole 20h, in the enlarged-diameter parts 31a, 31b at both the ends of the coupling member 31. The notch 31g constitutes a passage, through which the artificial ligament 30 is made to pass between the coupling member 31 and the inner surface of the fixing hole 20h when the coupling member 31 is mounted in the fixing hole 20h.

Figure 20:
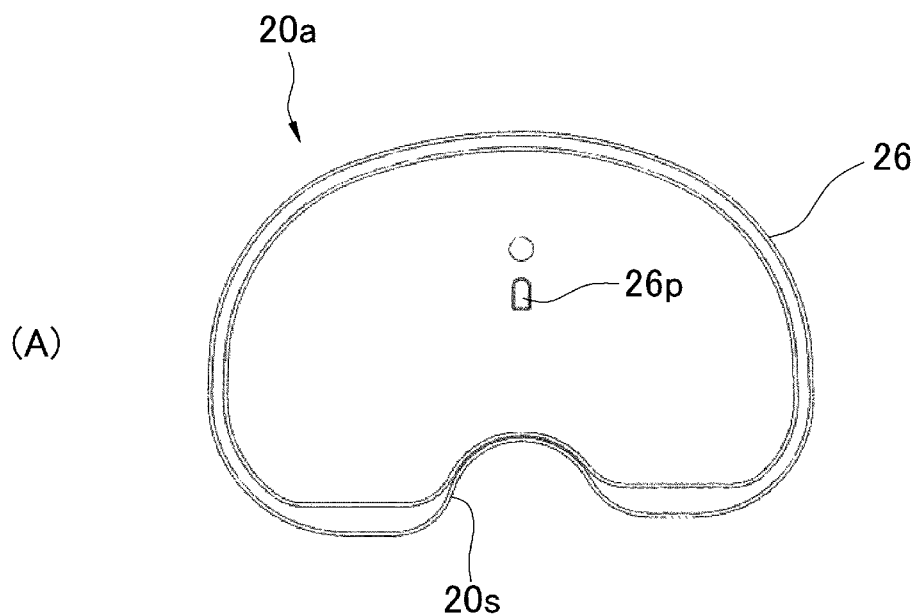
FIGS. 20(A) and 20(B) are plan and bottom views schematically illustrating the base part 20a in the tibia member 20 of the ligament reconstruction type artificial knee joint 1 of another embodiment, respectively.
Figure 20:
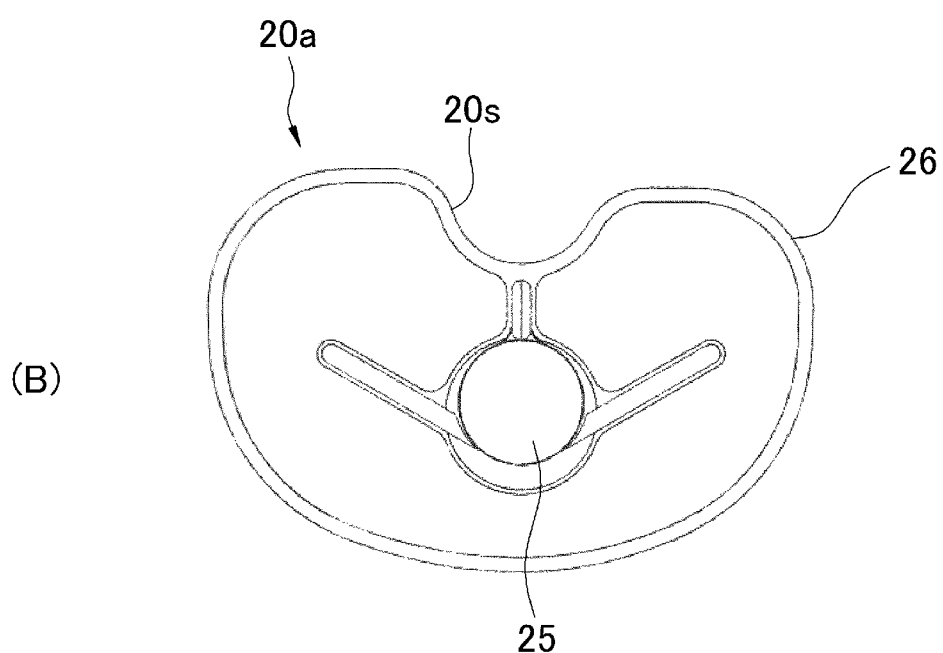

On the other hand, a notch 31k is also provided on the side (in FIGS. 21 and 23, the enlarged-diameter part 31b), which is located on the lower side (the side of the base plate 26) when the coupling member 31 is mounted in the fixing hole 20h, in the enlarged-diameter parts 31a, 31b at both the ends of the coupling member 31. The notch 31k is engaged with a protrusion 26p (see FIG. 20) of the base plate 26 to position the coupling member 31 when the coupling member 31 is mounted in the fixing hole 20h. Specifically, the notch 31k and the protrusion 26p of the base plate 26 are provided such that the coupling member 31 is mounted in the fixing hole 20h while the notch 31g of the enlarged-diameter part 31a is located on the opposite side to the lateral condyle inside wall 13 of the femur member 10.

The use of the coupling member 31 having the above structure can fix the other end of the artificial ligament 30 to the tibia member 20 when the other end of the artificial ligament 30 is hooked on the narrow part 31c to fix the coupling member 31 into the fixing hole 20h. The ring-shaped artificial ligament 30 can be put in the twisted state between the engagement part 14 and the fixing hole 20h.

The through-hole piercing the center of the coupling member 31 is one in which a screw is inserted to fix the coupling member 31 to the base plate 26.

(Another Example of Coupling Member 51)

In the above example, the section of the posterior cruciate ligament coupling member 51 has the substantially same shape as the coupling member fixing part 20t, and the front-side surface of the posterior cruciate ligament coupling member 51 is formed so as to be in close contact with the rear surface of the notch 20s of the contact part 20b. However, the posterior cruciate ligament coupling member 51 may have another shape as long as the other end of the artificial posterior cruciate ligament 35 can be fixed to the coupling member fixing part 20t.

For example, the section of the posterior cruciate ligament coupling member 51 may have the shape different from that of the coupling member fixing part 20t while the front-side surface of the posterior cruciate ligament coupling member 51 is in close contact with the rear surface of the notch 20s of the contact part 20b. However, when the section of the posterior cruciate ligament coupling member 51 has the substantially same shape as the coupling member fixing part 20t, a step is not formed at a boundary (a boundary in the rear surface of the tibia member 20) between the coupling member fixing part 20t and the posterior cruciate ligament coupling member 51. Therefore, friction between the artificial knee joint 1B and a muscle around the joint can be desirably reduced.

The section of the posterior cruciate ligament coupling member 51 may have the substantially same shape as the posterior cruciate ligament coupling member 51 while the front-side surface of the posterior cruciate ligament coupling member 51 is not in close contact with the rear surface of the notch 20s of the contact part 20b. However, the posterior cruciate ligament coupling member 51 can stably be fixed when the front-side surface of the posterior cruciate ligament coupling member 51 is in close contact with the rear surface of the notch 20s of the contact part 20b. That is, the other end of the artificial posterior cruciate ligament 35 can stably be fixed to the tibia member 20.

(Another Method for Fixing Artificial Ligament 30 and Artificial Posterior Cruciate Ligament 35)

There is no particular limitation to the method for fixing both the ends of the artificial ligament 30 to the lateral condyle inside wall 13 of the femur member 10 and the tibia member 20. For example, members such as screws may be fixed to both the ends of the artificial ligament 30, and the screws may be engaged with the lateral condyle inside wall 13 of the femur member 10 and the contact part 20b of the tibia member 20 to fix both the ends of the artificial ligament 30.

Similarly, there is no particular limitation to the method for fixing both the ends of the artificial posterior cruciate ligament 35 to the medial condyle inside wall 15 of the femur member 10 and the tibia member 20. For example, members such as screws may be fixed to both the ends of the artificial posterior cruciate ligament 35, and the screws may be engaged with the medial condyle inside wall 15 of the femur member 10 and the base part 20a or contact part 20b of the tibia member 20 to fix both the ends of the artificial posterior cruciate ligament 35.

(Another Artificial Ligament 30 and another Artificial Posterior Cruciate Ligament 35)

The artificial ligament 30 and the artificial posterior cruciate ligament 35 are not necessarily formed into the ring shape. For example, the artificial ligament 30 and the artificial posterior cruciate ligament 35 are integrated into one string shape, a ring-shaped portion is provided at each of both ends of the string, and the ring-shaped portion may be coupled to or engaged with the engagement part 14 or posterior cruciate ligament engagement part 16, the coupling member 31, and the posterior cruciate ligament coupling member 51.

(Others)

The artificial knee joint 1 including only the artificial ligament 30 acting as the anterior cruciate ligament and the artificial knee joint 1B including both the artificial ligament 30 and the artificial posterior cruciate ligament 35 are described in the above example. Alternatively, the artificial ligament 30 is not provided in the artificial knee joint of the present invention, but the artificial knee joint may include only the artificial posterior cruciate ligament 35. Even in this case, the artificial knee joint including the anterior cruciate ligament and the posterior cruciate ligament can be obtained by the reconstruction of the anterior cruciate ligament by another method.

(Ligament Reconstruction Type Artificial Knee Joint 1C of Embodiment)

In the ligament reconstruction type artificial knee joints 1, 1B of the above embodiments, one or two artificial ligaments are provided, and the artificial ligament has the ring shape. Alternatively, the artificial ligament may be constructed with plural ligament members.

An anterior cruciate ligament in a knee of a healthy person has a certain degree of section, and a surface having a certain area in the anterior cruciate ligament is fixed to a femur or a tibia. Additionally, an anterior cruciate ligament exerts a fluctuation in tensile force like an assembly of plural bundles of ligaments. That is, the plural bundles of ligaments are gathered together to form the anterior cruciate ligament, and each bundle of ligaments exerts a different fluctuation in tensile force in bending and stretching the knee due to an interference state with the intercondylar eminence 23 or a difference of a relative position between the bundles of ligaments. Accordingly, when the artificial ligament is constructed with plural ligament members, the function close to the knee of the healthy person is easily exerted even if the knee is replaced for the artificial knee joint.

In the case that the artificial ligament is constructed with the plural ligament members, the artificial ligament can be coupled to the lateral condyle inside wall 13 of the femur member 10 and the tibia member 20 by the following method.

As illustrated in FIGS. 41 to 45, the artificial ligament 60 is constructed with plural ligament members 61. One end of the plural ligament members 61 is coupled to a femur coupling member 71, and the other end is coupled to a tibia coupling member 72.

The femur coupling member 71 is formed into a substantially cylindrical shape, and a fixing through-hole 71*h* is made in a central portion of the femur coupling member 71. When the femur coupling member 71 is inserted in the femur fixing hole made in the femur member 10 while the screw is inserted in the through-hole 71*h*, the femur coupling member 71 can be screwed to the femur member 10 and the femur DT. That is, the femur coupling member 71 can be fixed to the femur member 10 or the femur DT. Additionally, when the femur coupling member 71 is fixedly inserted in the femur fixing hole, the through-hole 71*h* is made such that the center of the femur coupling member 71 is substantially matched with the position where once the anterior cruciate ligament exists in the knee replaced for the artificial knee joint on the inside of the lateral condyle of the femur member 10.

The method for fixing the femur coupling member 71 to the femur member 10 or the femur DT is not limited to the screw clamp, but various methods can be adopted. For example, the femur coupling member 71 can be fixed to the femur member 10 or the femur DT using an adhesive. Even in this case, when the femur coupling member 71 is inserted in the femur fixing hole, the femur coupling member 71 is formed such that the center of the femur coupling member 71 is substantially matched with the position where once the anterior cruciate ligament exists in the knee replaced for the artificial knee joint on the inside of the lateral condyle of the femur member 10.

In the femur coupling member 71, plural ligament insertion holes 71*s* are made around the through-hole 71*h* in order to fixedly insert the ligament members 61. The plural ligament insertion holes 71*s* are made as many as the ligament members 61 on the surface side of the femur coupling member 71, namely, on the side located in the surface when the femur coupling member 71 is mounted on the femur member 10. On the surface side of the femur coupling member 71, the plural ligament insertion holes 71*s* are made so as to surround the center of the femur coupling member 71. On the surface side of the femur coupling member 71, the portion in which the plural ligament insertion holes 71*s* are disposed is provided such that the anterior cruciate ligament of the healthy knee has the substantially same area as a range (coupling surface) coupled to the inside of the lateral condyle of the femur. That is, the plural ligament insertion holes 71*s* are made such that the center of the femur coupling member 71 is surrounded by the plural ligament members 61 when the ligament members 61 are disposed in the plural ligament insertion holes 71*s*, and such that the area of the portion surrounded by the plural ligament members 61 is substantially equal to the area in which the anterior cruciate ligament of the healthy knee is coupled to the inside of the lateral condyle of the femur.

As described above, in the femur coupling member 71, when the femur coupling member 71 is fixedly inserted in the femur fixing hole, the through-hole 71*h* is made such that the center of the femur coupling member 71 is substantially matched with the position where once the anterior cruciate ligament exists in the knee replaced for the artificial knee joint on the inside of the lateral condyle of the femur member 10. Accordingly, when the plural ligament insertion holes 71*s* are made to fixedly insert the femur coupling member 71 in the femur fixing hole, one end of each of the plural ligament members 61 is disposed within a certain range including the center of the position where once the anterior cruciate ligament exists in the knee replaced for the artificial knee joint on the inside of the lateral condyle of the femur member 10.

On the other hand, a groove connecting the adjacent ligament insertion holes 71*s* to each other is provided on the rear surface side of the femur coupling member 71. Similarly to the coupling member 31, the femur coupling member 71 has the structure in which the ligament member 61 is hooked on the portion between the adjacent ligament insertion holes 71*s* when the ligament member 61 is made to pass through the adjacent ligament insertion holes 71*s*.

A space in which the ligament member 61 is accommodated is provided between the adjacent ligament insertion holes 71*s* such that the ligament member 61 does not pop out from the rear surface of the femur coupling member 71.

The femur coupling member 71 does not necessarily have the structure in which the ligament member 61 is hooked between the adjacent ligament insertion holes 71*s* as long as the ligament member 61 can be held so as not to pop out. For example, a member may be provided at one end of the ligament member 61 so as not to be able to pass through the ligament insertion hole 71*s*, or a mechanism (such as a protrusion engaged with the ligament member 61) may be provided so as to hold one end of the ligament member 61.

On the other hand, the tibia coupling member 72 has the substantially same shape as the femur coupling member 71.

That is, the tibia coupling member 72 is also formed into the substantially cylindrical shape, and a fixing through-holes 72*h* is made in a central portion of the tibia coupling member 72. When the tibia coupling member 72 is inserted in the tibia fixing hole made in the tibia member 20 while the screw is inserted in the through-hole 72*h*, tibia coupling member 72 can be fixedly screwed to the tibia member 20 and the tibia PE. Additionally, the through-hole 72*h* is formed such that when the tibia coupling member 72 is fixedly inserted in the tibia fixing hole, the center of the tibia coupling member 72 is substantially matched with the position where once the anterior cruciate ligament exists in the knee replaced for the artificial knee joint on the upper side of the tibia member 20.

The method for fixing the tibia coupling member 72 to the tibia member 20 or the tibia PE is not limited to the screw clamp, but various methods can be adopted. For example, the femur coupling member 71 can be fixed to the femur member 10 or the tibia PE using an adhesive. Even in this case, when the tibia coupling member 72 is inserted in the tibia fixing hole, the tibia coupling member 72 is formed such that the center of the tibia coupling member 72 is substantially matched with the position where once the anterior cruciate ligament exists in the knee replaced for the artificial knee joint on the upper side of the tibia member 20.

The tibia coupling member 72 also includes plural ligament insertion holes 72*s* around the through-hole 72*h* in order to fixedly insert the ligament members 61. The plural ligament insertion holes 72*s* are made as many as the through-holes 71*h* of the femur coupling member 71. The plural ligament insertion holes 72*s* are made as many as the ligament members 61 on the surface side of the tibia coupling member 72, namely, on the side located in the top surface when the tibia coupling member 72 is mounted on the tibia member 20. On the surface side of the tibia coupling member 72, the plural ligament insertion holes 72s are made so as to surround the center of the tibia coupling member 72. On the surface side of the tibia coupling member 72, the portion in which the plural ligament insertion holes 72s are disposed is provided such that the anterior cruciate ligament of the healthy knee has the substantially same area as a range (coupling surface) coupled to the top surface of the tibia. That is, the plural ligament insertion holes 72s are made such that the center of the tibia coupling member 72 is surrounded by the plural ligament members 61 when the ligament members 61 are disposed in the plural ligament insertion holes 72s, and such that the area of the portion surrounded by the plural ligament members 61 is substantially equal to the area in which the anterior cruciate ligament of the healthy knee is coupled to the top surface of the tibia.

As described above, in the tibia coupling member 72, when the tibia coupling member 72 is fixedly inserted in the femur fixing hole, the through-hole 72h is made such that the center of the tibia coupling member 72 is substantially matched with the position where once the anterior cruciate ligament exists in the knee replaced for the artificial knee joint in the top surface of the tibia member 20. Accordingly, when the plural ligament insertion holes 72s are made to fixedly insert the tibia coupling member 72 in the tibia fixing hole as described above, one end of each of the plural ligament members 61 is disposed within a certain range including the center of the position where once the anterior cruciate ligament exists in the knee replaced for the artificial knee joint in the top surface of the tibia member 20.

On the other hand, similarly to the femur coupling member 71, a groove connecting the adjacent ligament insertion holes 72s to each other is provided on the rear surface side of the tibia coupling member 72. Similarly to the coupling member 31 or the femur coupling member 71, the tibia coupling member 72 has the structure in which the ligament member 61 is hooked on the portion between the adjacent ligament insertion holes 72s when the ligament member 61 is made to pass through the adjacent ligament insertion holes 72s.

A space in which the ligament member 61 is accommodated is provided between the adjacent ligament insertion holes 72s such that the ligament member 61 does not pop out from the rear surface of the tibia coupling member 72.

The tibia coupling member 72 does not necessarily have the structure in which the ligament member 61 is hooked between the adjacent ligament insertion holes 72s as long as the ligament member 61 can be held so as not to pop out. For example, a member may be provided at one end of the ligament member 61 so as not to be able to pass through the ligament insertion hole 72s, or a mechanism (such as a protrusion engaged with the ligament member 61) may be provided so as to hold one end of the ligament member 61.

In the above shape, as described above, when the femur coupling member 71 is fixedly inserted in the femur fixing hole, the center of the femur coupling member 71 is substantially matched with the position where once the anterior cruciate ligament exists in the knee replaced for the artificial knee joint on the inside of the lateral condyle of the femur member 10. When the tibia coupling member 72 is fixedly inserted in the tibia fixing hole, the center of the tibia coupling member 72 is substantially matched with the position where once the anterior cruciate ligament exists in the knee replaced for the artificial knee joint on the upper side of the tibia member 20.

One end of each of the plural ligament members 61 of the artificial ligament 60 is disposed in a certain range including the center of the position where once the anterior cruciate ligament exists in the knee replaced for the artificial knee joint on the inside of the lateral condyle of the femur member 10. The other end of each of the plural ligament members 61 of the artificial ligament 60 is disposed in a certain range including the center of the position where once the anterior cruciate ligament exists in the knee replaced for the artificial knee joint on the upper side of the tibia member 20. Therefore, in bending and stretching the knee, the interference state with the intercondylar eminence 23 and the twisted state vary depending on the position where each ligament member 61 is provided, and the tensile force generated in the ligament member 61 can exert a different fluctuation. The plural ligament members 61 of the artificial ligament 60 acts as the plural bundles of ligaments constituting the anterior cruciate ligament of the healthy person, so that the fluctuation in tensile force similar to the anterior cruciate ligament of the healthy person can be generated. That is, each ligament member 61 properly generates the tensile force in bending and stretching the knee joint, so that the movement of the knee replaced for artificial joint can be brought close to that of the healthy knee.

The femur coupling member 71 or the tibia coupling member 72 may be fixed to the femur member 10 or the tibia member 20 such that a part of or all the plural ligament members 61 of the artificial ligament 60 are twisted while the femur coupling member 71 or the tibia coupling member 72 is mounted on the femur member 10 or the tibia member 20. Specifically, in association with the movement to bend and stretch the knee, the twist is generated or released in a part of or all the plural ligament members 61 of the artificial ligament 60. On the other hand, the initial twist may be generated in a part of or all the plural ligament members 61 while the knee is stretched.

In the above example, the femur coupling member 71 and the tibia coupling member 72 have the substantially cylindrical shape. However, there is no particular limitation to the shapes of the femur coupling member 71 and the tibia coupling member 72, but various shapes can be adopted. For example, the femur coupling member 71 and the tibia coupling member 72 may be formed into an elliptical shape in section, a quadrangle shape in section, or a triangular shape in section.

Additionally, with respect to the center of the femur coupling member 71 or tibia coupling member 72, the plural ligament members 61 of the artificial ligament 60 may be disposed at equal intervals (equal angle interval) or an interval between the ligament members 61 may be changed according to the position.

Practical Example

The function of the normal anterior cruciate ligament was evaluated, the simulation was performed by an image matching method (see Ishimaru M, Hino K, Miura H etc, J Orthop Res. 2014 May; 32 (5): 619-26. doi: 10.1002/jor.22596.) developed by the inventors in order to verify the position, where the artificial ligament is coupled to the femur member and the tibia member to exert the function of the anterior cruciate ligament in the normal knee, when the artificial knee joint of the present invention was used, and a relationship among a load on the knee of a living body, the knee bending angle under a dynamic condition, and the ligament length (a distance between one end at which the anterior cruciate ligament is joined to the femur and one end at which the anterior cruciate ligament is joined to the tibia, hereinafter simply referred to as a ligament length) was obtained.

Figure 46:
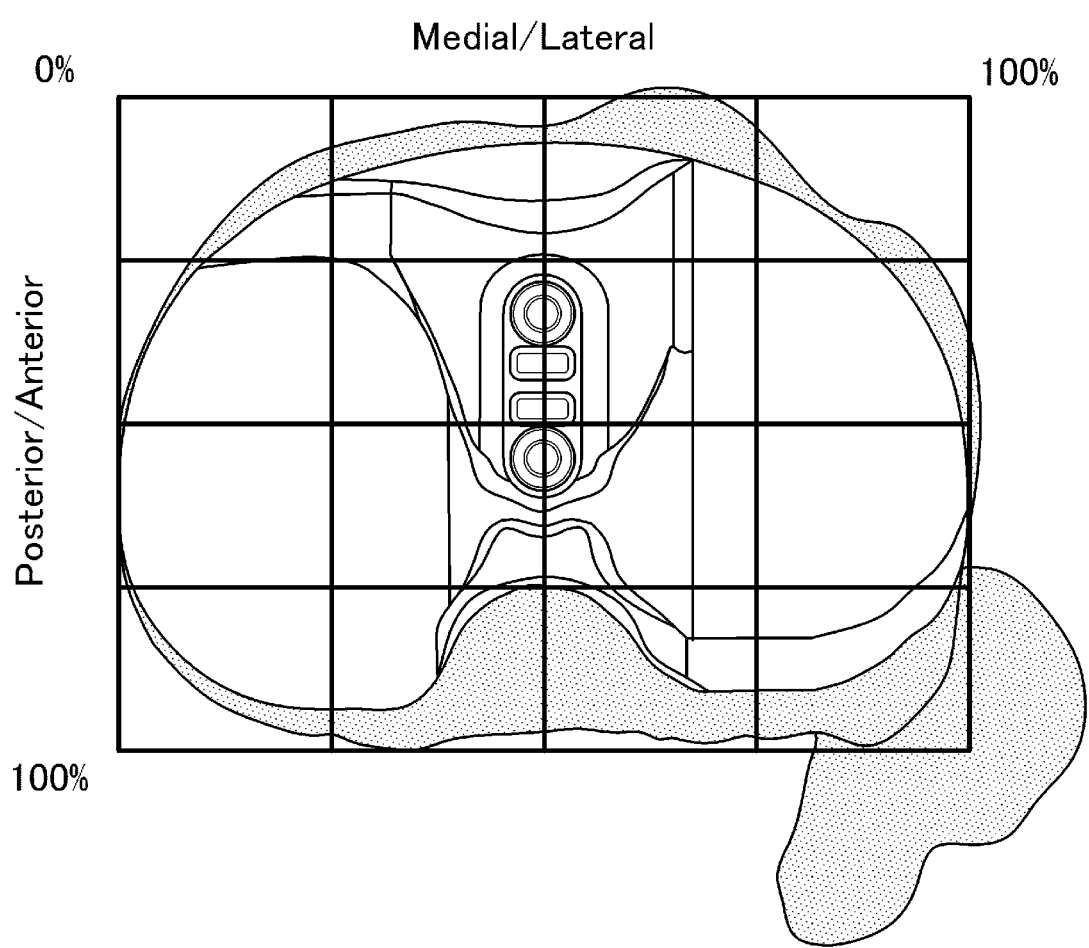
FIG. 46 is a view illustrating a joining position (a coupling member mounting position on a tibia side) relationship between the anterior cruciate ligament and the tibia in a simulation of a practical example.
Figure 47:
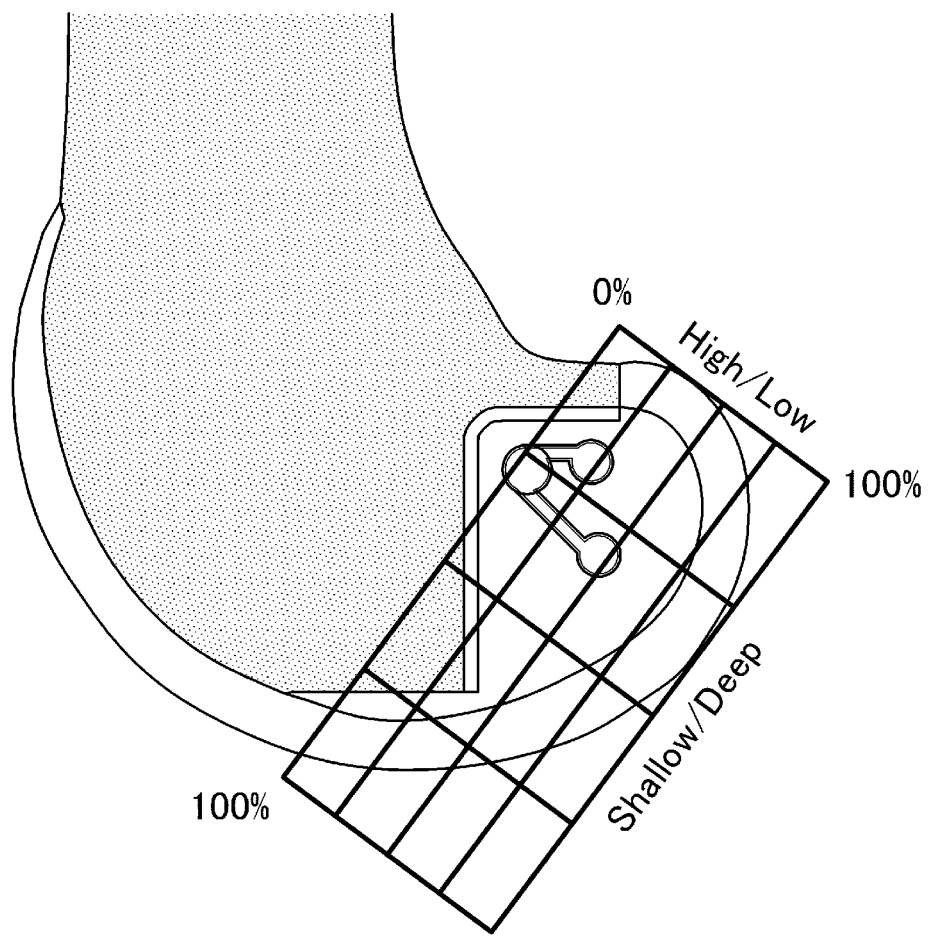
FIG. 47 is a view illustrating a joining position (the position of the engagement part) relationship between the anterior cruciate ligament and the femur in the simulation of the practical example.
Figure 48:
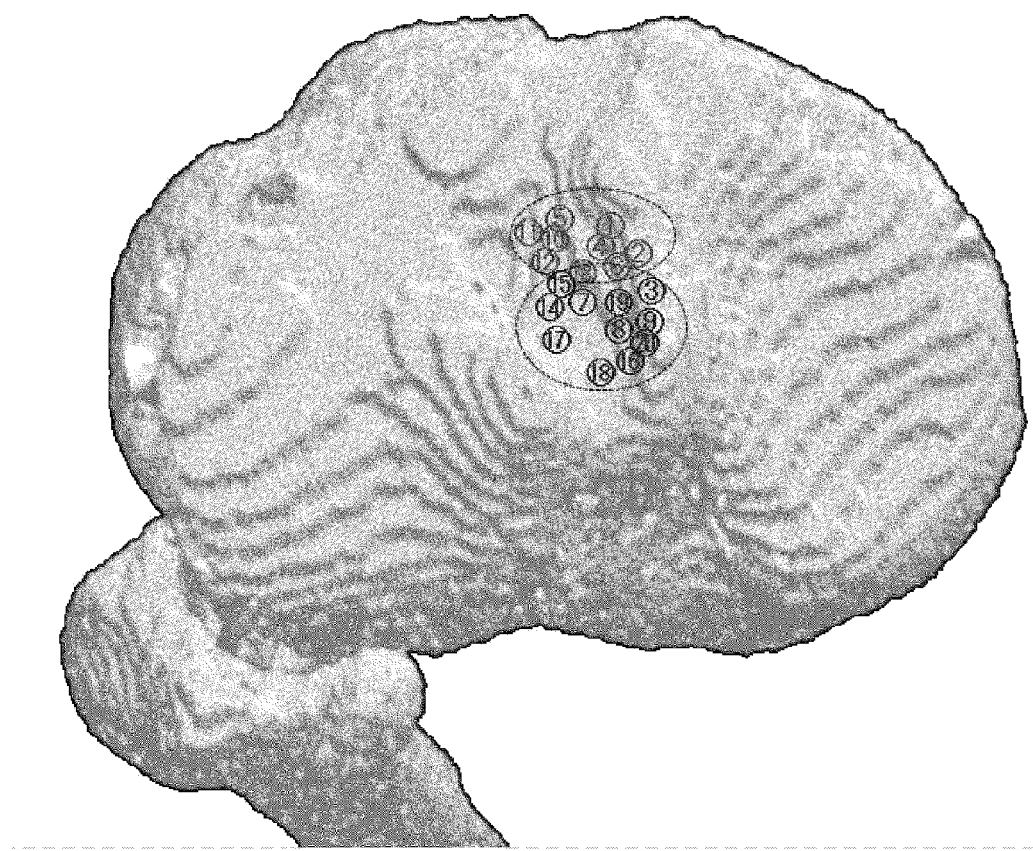
FIG. 48 is a view illustrating the joining position relationship between the anterior cruciate ligament and the tibia in the simulation of the practical example.
Figure 49:
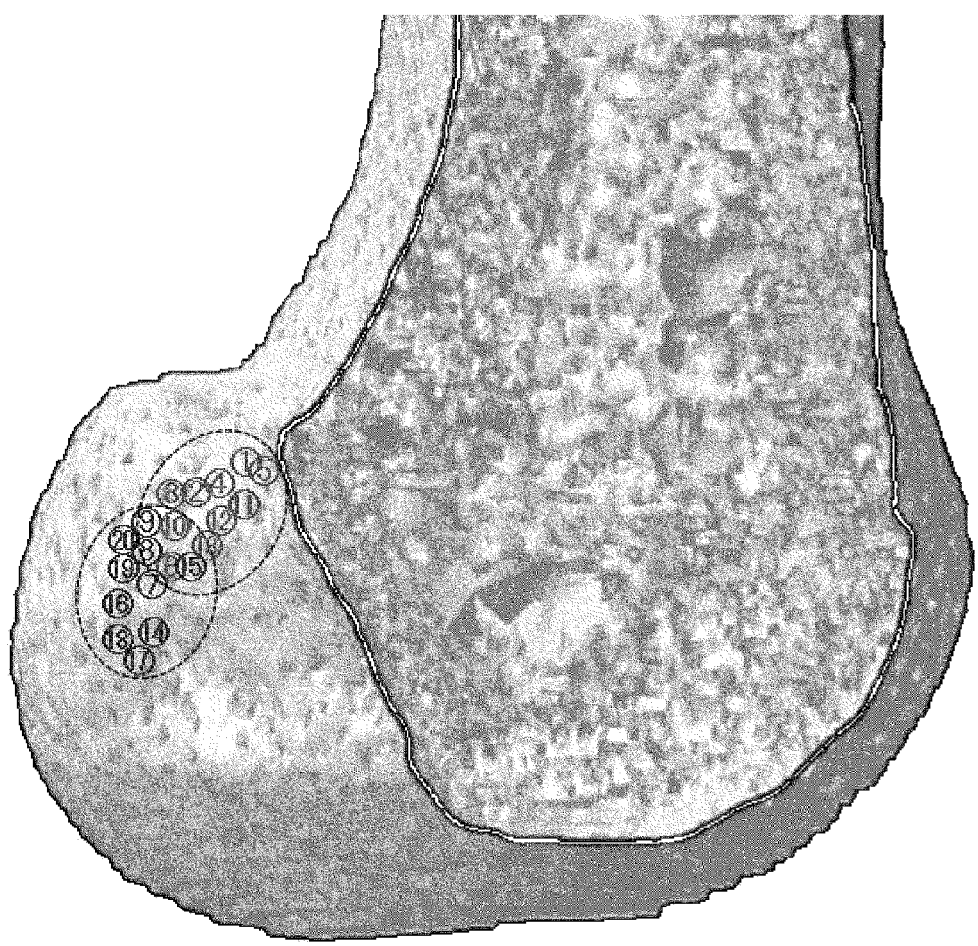
FIG. 49 is a view illustrating the joining position relationship between the anterior cruciate ligament and the femur in the simulation of the practical example.

In a practical example, the relationship between the knee bending angle and the length of each bundle (1 to 20) of anterior cruciate ligaments was simulated with respect to the case that one end of each of the plural bundles (1 to 20) of anterior cruciate ligaments was disposed at the position where the coupling member is disposed in the tibia member (see FIGS. 46 and 48) while the other end of each of the plural bundles (1 to 20) of anterior cruciate ligaments was disposed at the position where the engagement part is disposed in the femur member (see FIGS. 47 and 49).

That is, in the simulation, one end of each of the plural bundles (1 to 20) of anterior cruciate ligaments was disposed within the position of 25% to 50% from the front surface and the position of 0 to 10% from right to left from the center in the right and left direction in the posterior and anterior direction of the tibia member 20 in a coordinate in FIG. 46. In a coordinate in FIG. 47, the other end of each of the plural bundles (1 to 20) of anterior cruciate ligaments was disposed within the position of 12% to 40% from the front surface in a shallow/deep direction and the position of 10% to 60% in a high/low direction in the front surface direction of the femur.

In FIGS. 47 and 49, the position of each numerical character indicates the position where the bundles are joined to each other, and the positions having the same numerical character are joined to each other. Numerical characters 1 to 10 indicate a group (AM group) located on the front side of the anterior cruciate ligament, and numerical characters 11 to 20 indicate a group (PL group) located on the rear side of the anterior cruciate ligament.

FIGS. 50 to 60 illustrate results.

Figure 50:
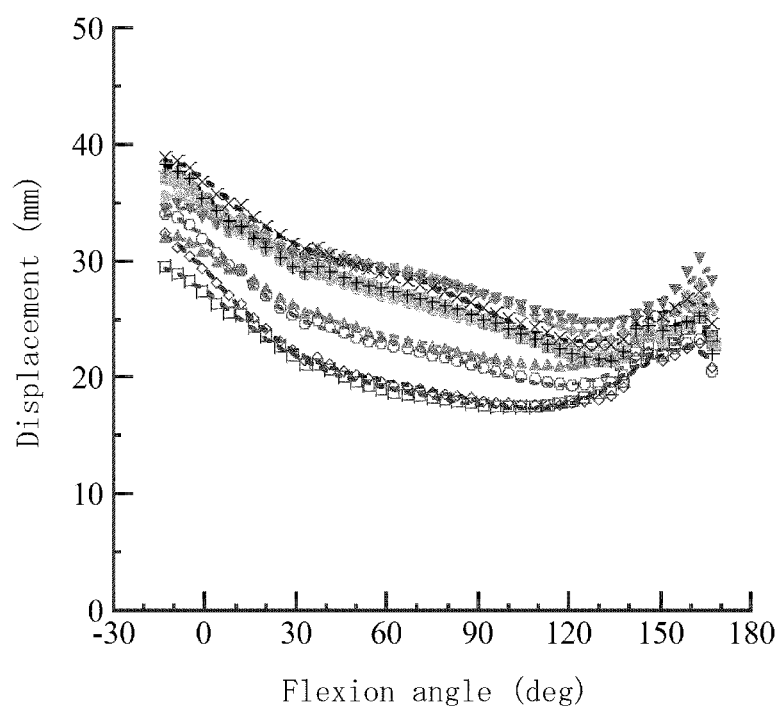
FIG. 50 is a view illustrating a relationship between a bending angle of the knee and a length of the ligament in the practical example.
Figure 51:
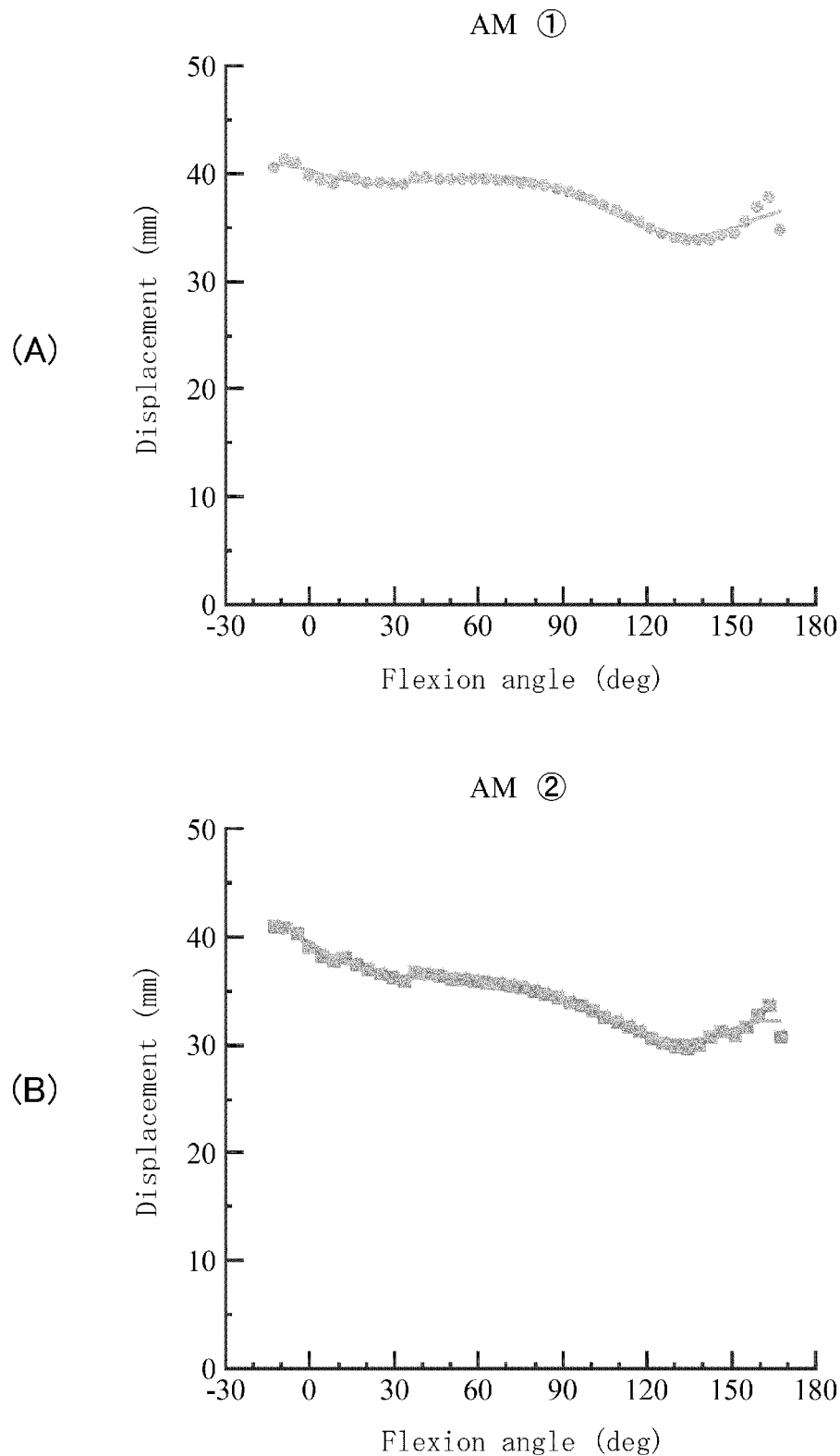
FIG. 51 is a view illustrating a relationship between the bending angle of the knee and the length of the ligament in the practical example.
Figure 52:
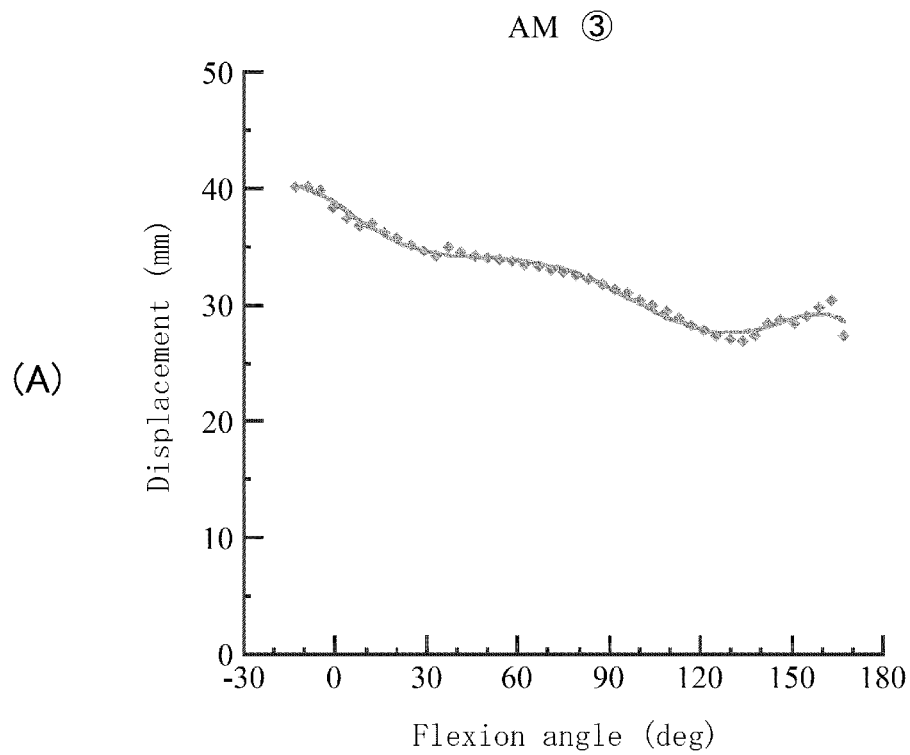
FIG. 52 is a view illustrating a relationship between the bending angle of the knee and the length of the ligament in the practical example.
Figure 52:
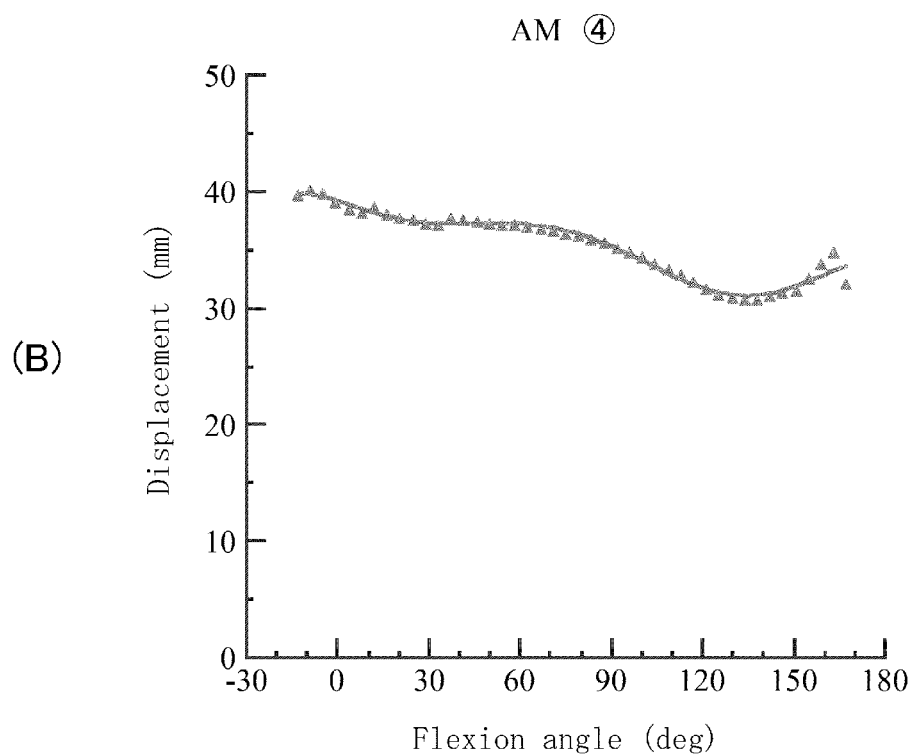
Figure 53:
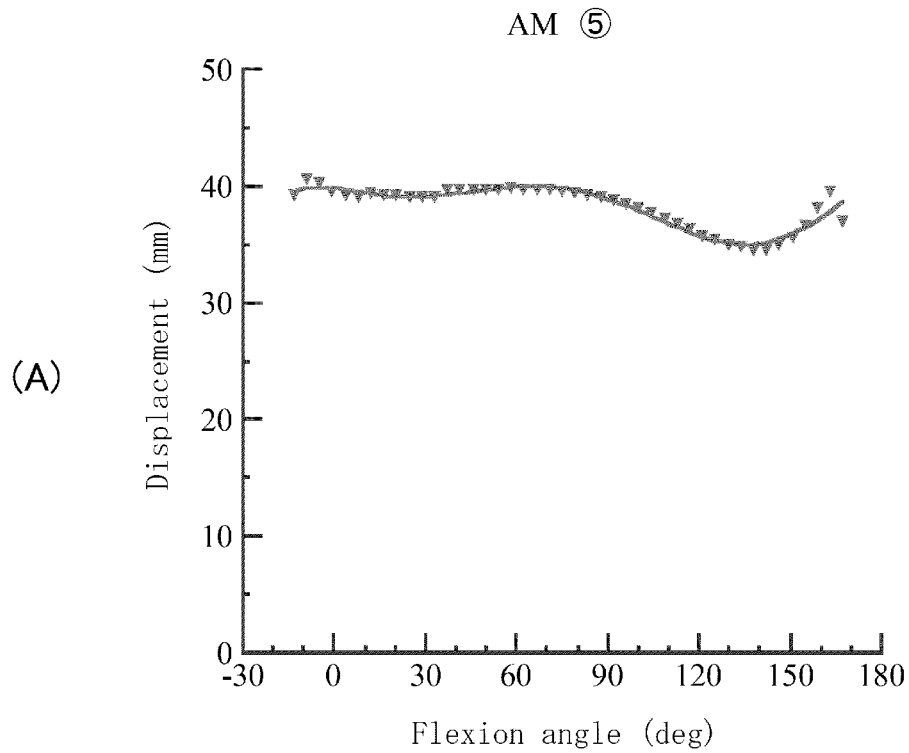
FIG. 53 is a view illustrating a relationship between the bending angle of the knee and the length of the ligament in the practical example.
Figure 53:
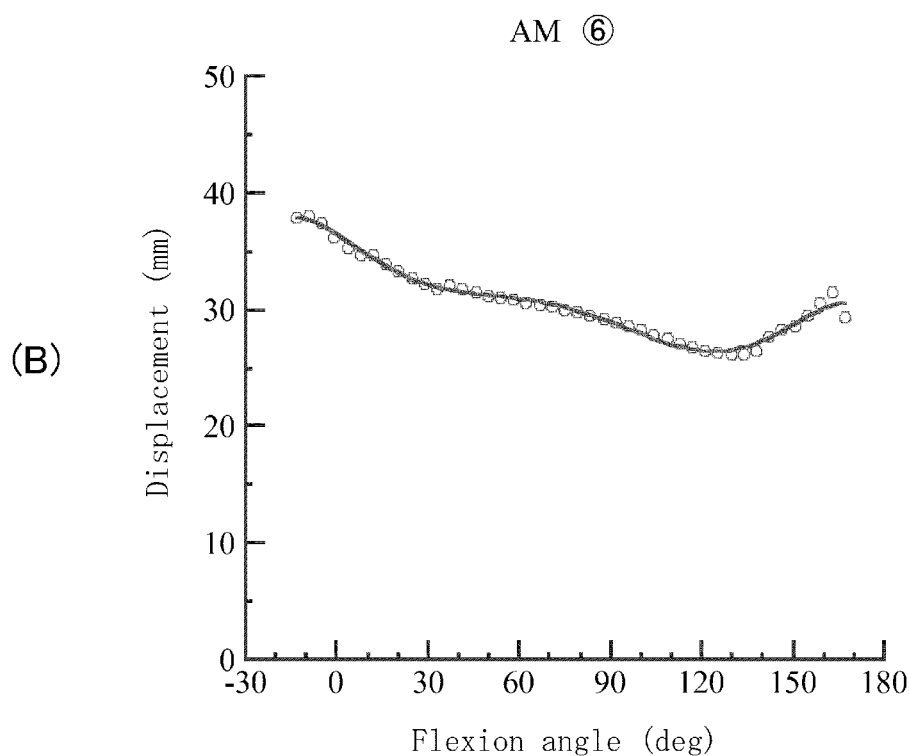
Figure 54:
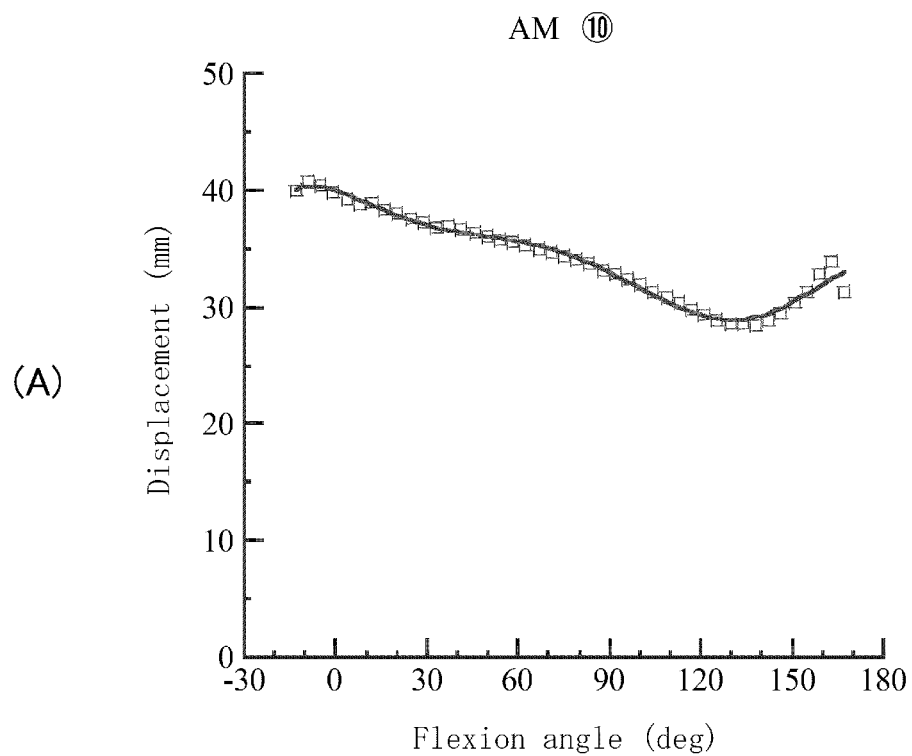
FIG. 54 is a view illustrating a relationship between the bending angle of the knee and the length of the ligament in the practical example.
Figure 54:
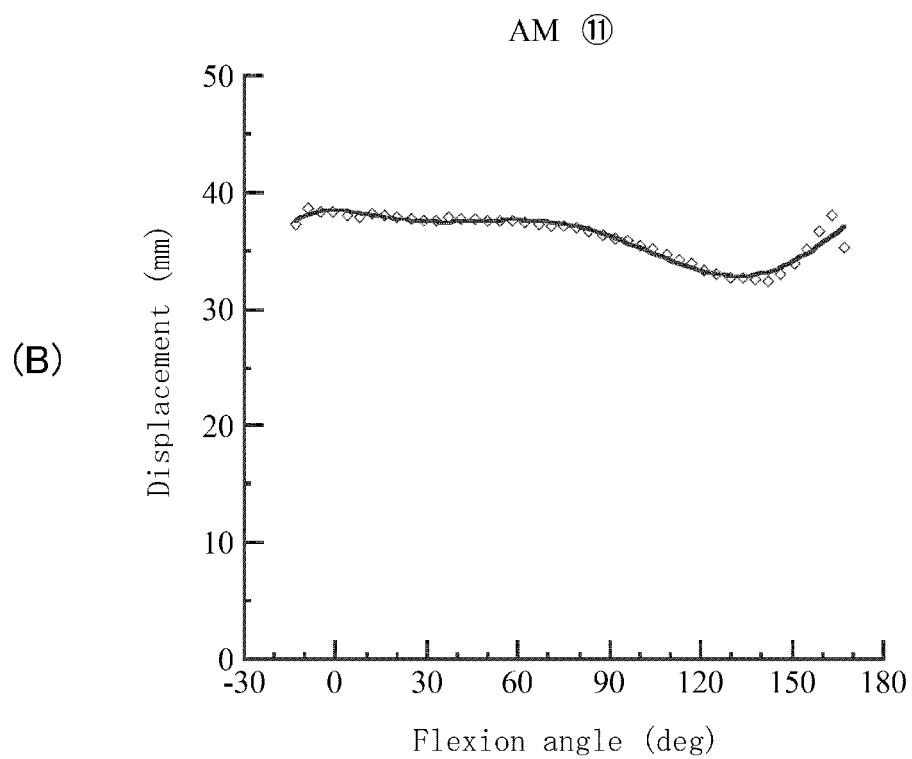
Figure 55:
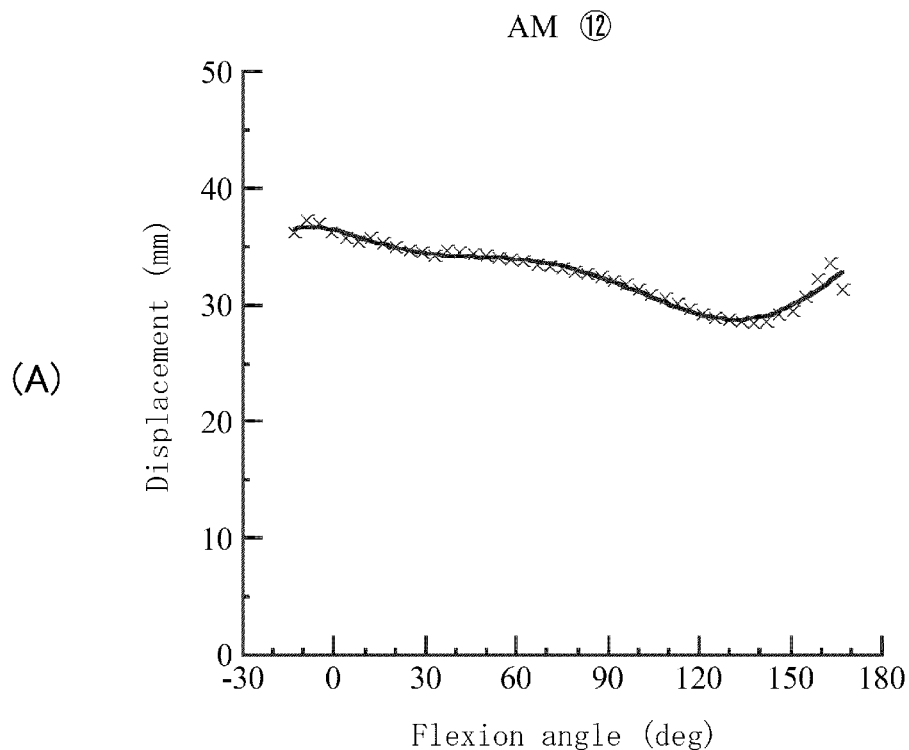
FIG. 55 is a view illustrating a relationship between the bending angle of the knee and the length of the ligament in the practical example.
Figure 55:
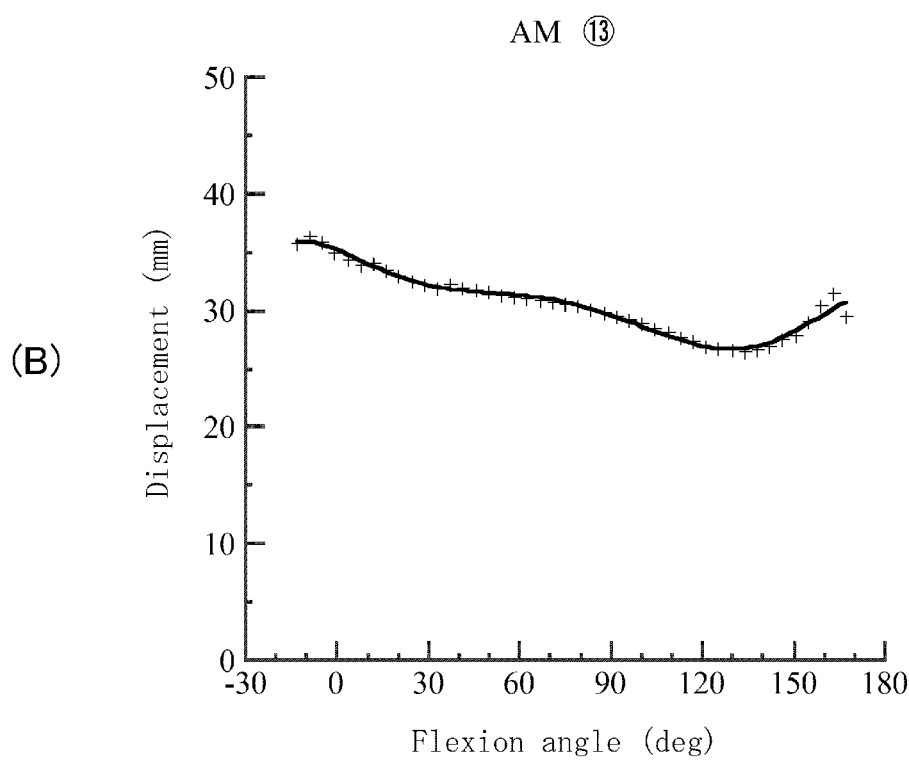
Figure 56:
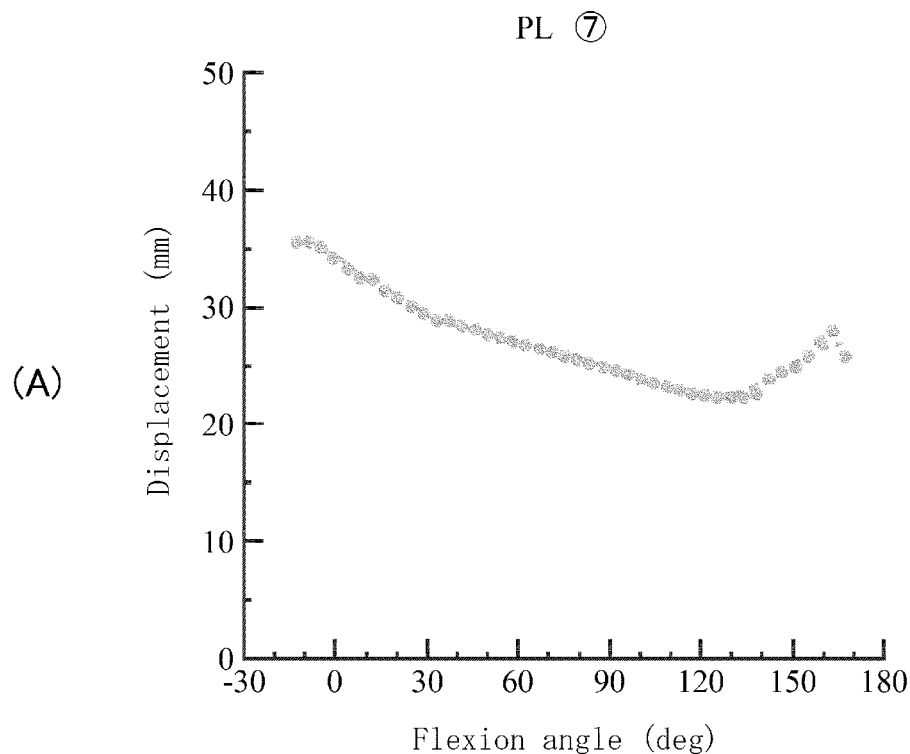
FIG. 56 is a view illustrating a relationship between the bending angle of the knee and the length of the ligament in the practical example.
Figure 56:
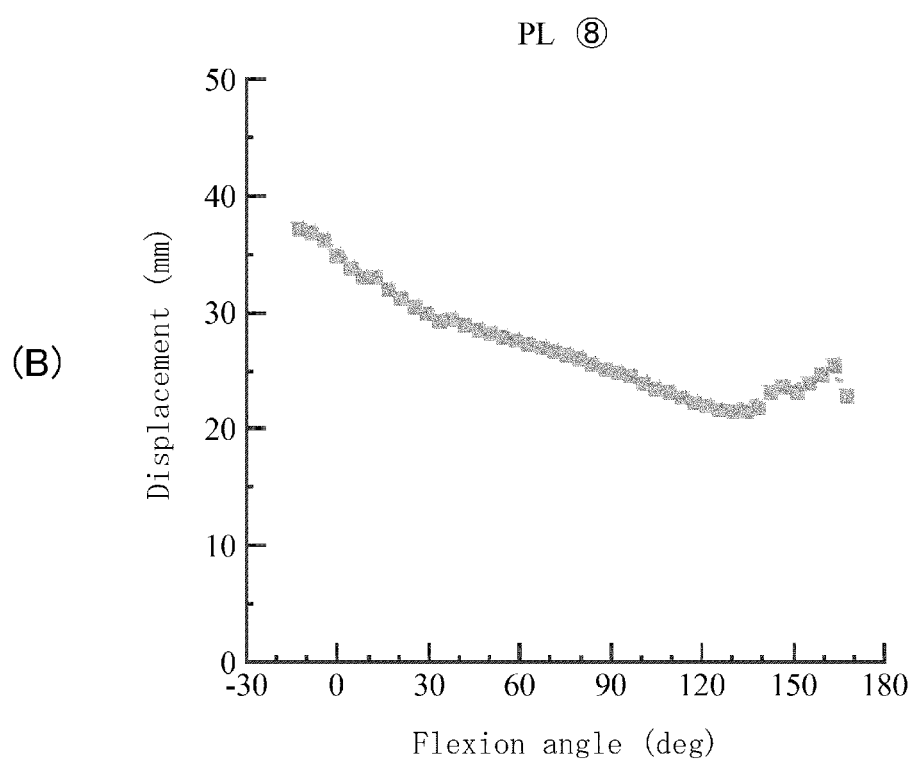
Figure 57:
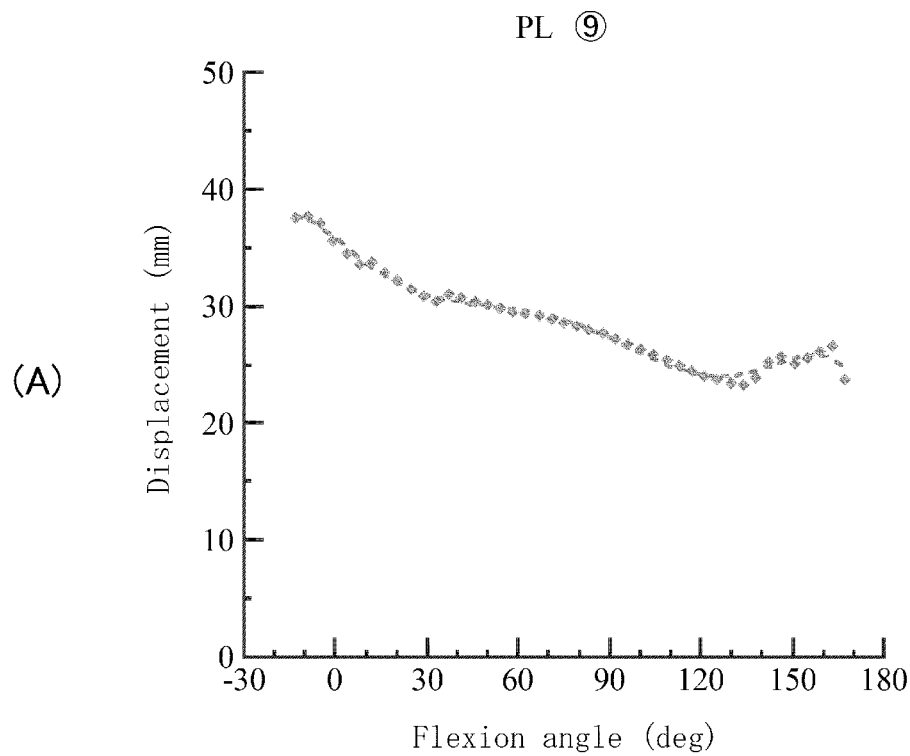
FIG. 57 is a view illustrating a relationship between the bending angle of the knee and the length of the ligament in the practical example.
Figure 57:
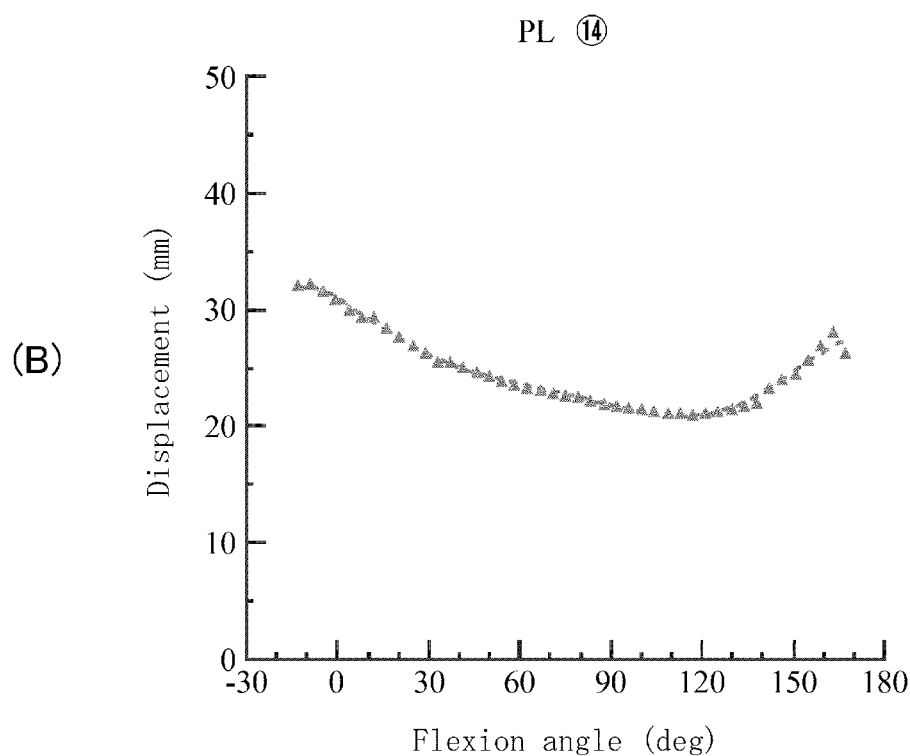
Figure 58:
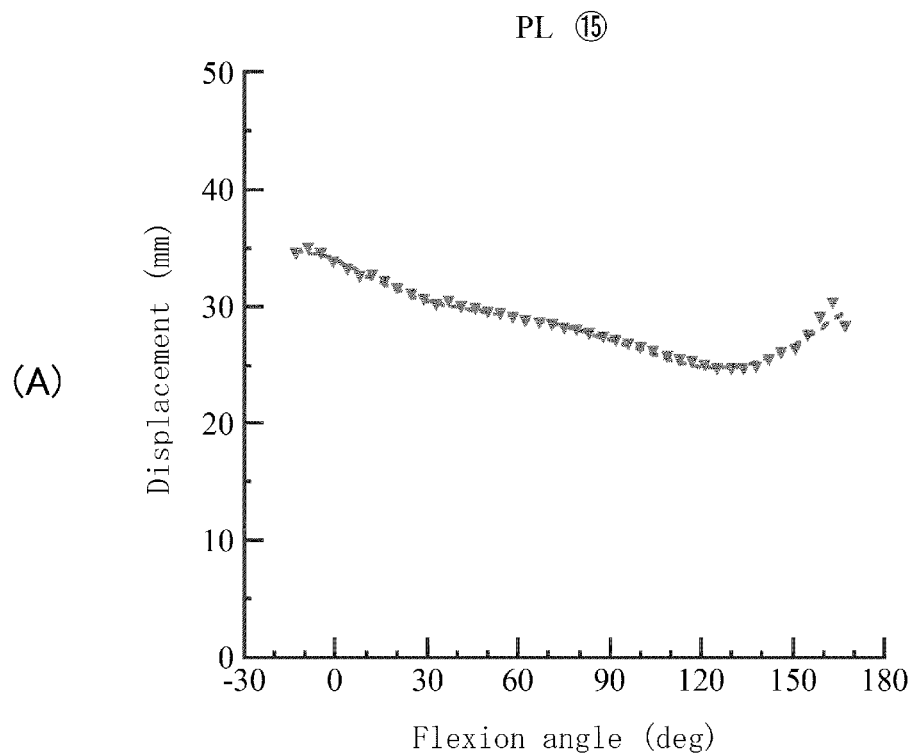
FIG. 58 is a view illustrating a relationship between the bending angle of the knee and the length of the ligament in the practical example.
Figure 58:
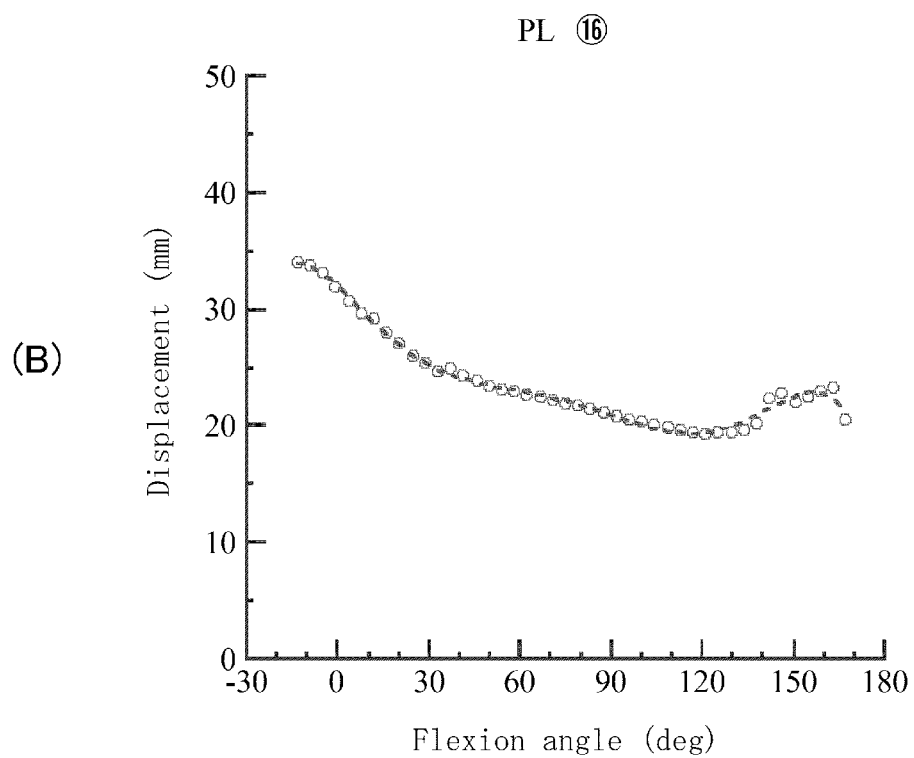
Figure 59:
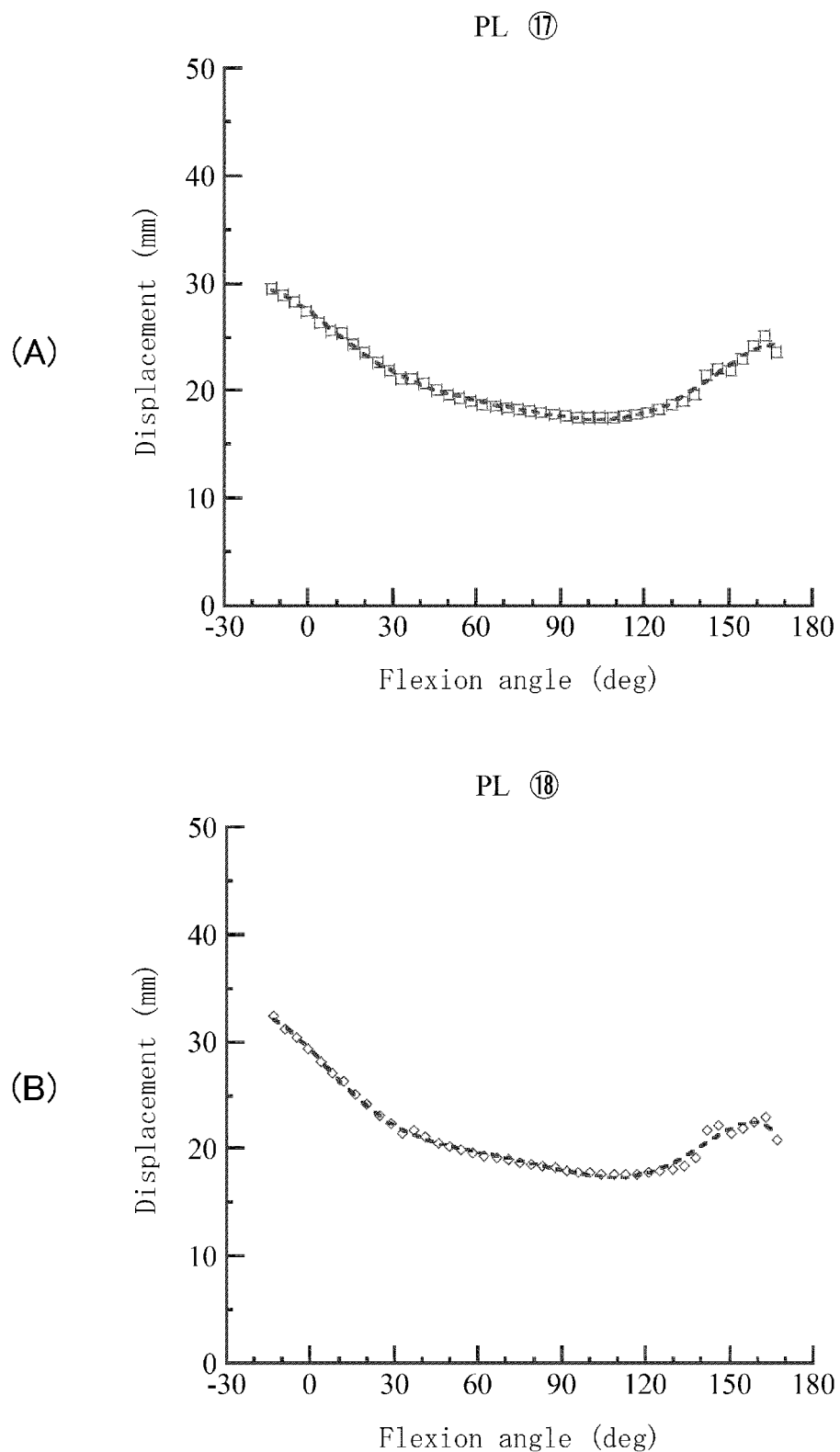
FIG. 59 is a view illustrating a relationship between the bending angle of the knee and the length of the ligament in the practical example.
Figure 60:
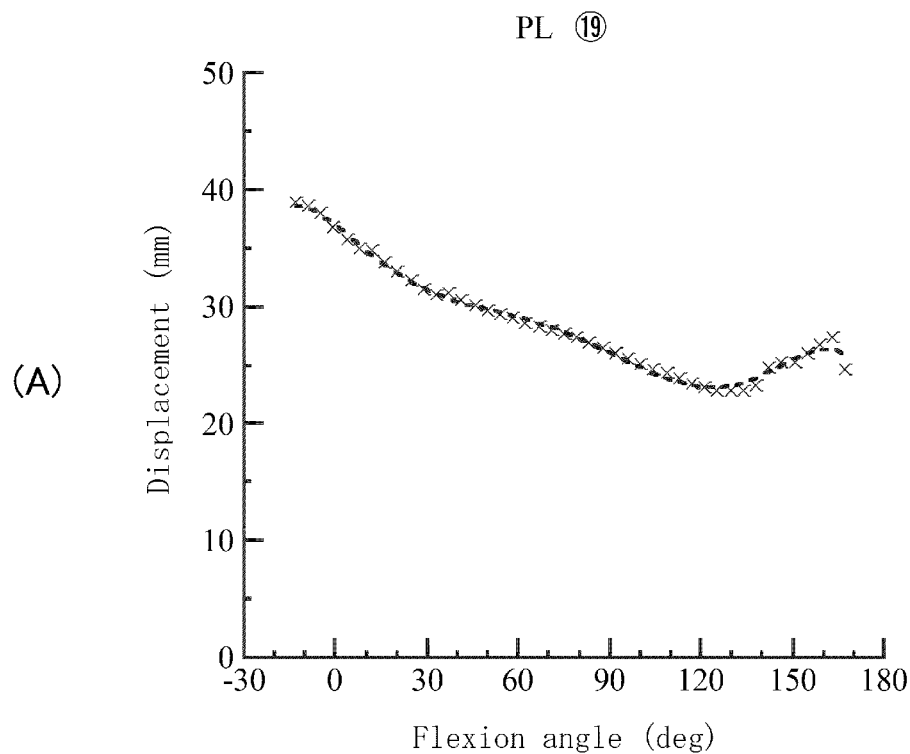
FIG. 60 is a view illustrating a relationship between the bending angle of the knee and the length of the ligament in the practical example.
Figure 60:
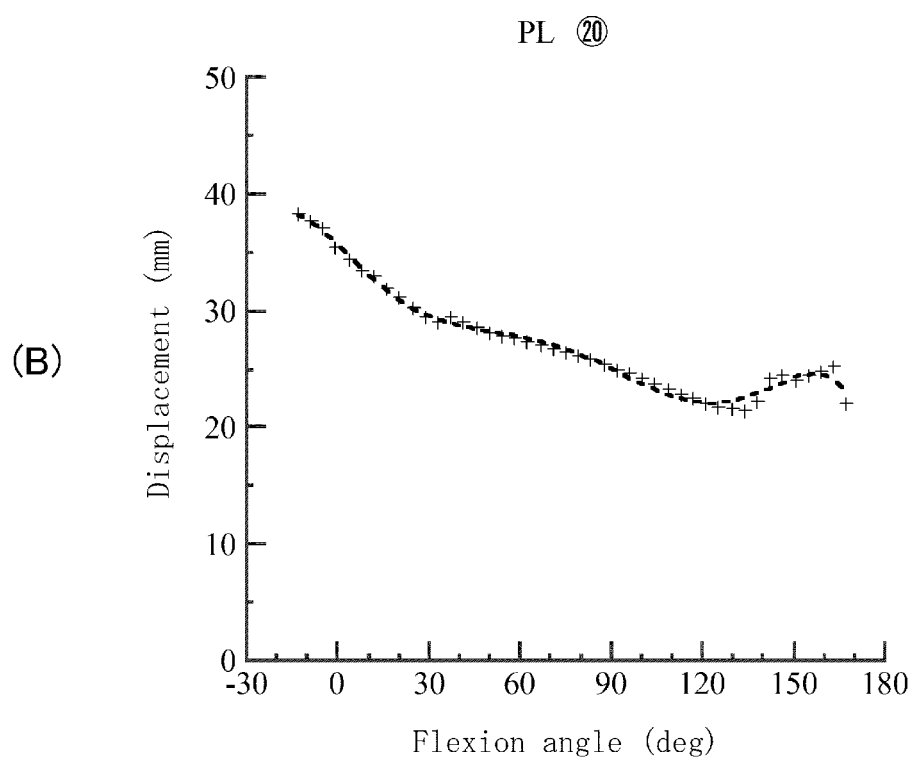

As illustrated in FIG. 50, in the practical example, it was checked that tendencies of the knee bending angle and the change in length of the anterior cruciate ligament indicated a tendency substantially same as that of the anterior cruciate ligament (DEFORT) of the normal knee, namely, it was checked that the reconstructed anterior cruciate ligament exerted the function equal to the anterior cruciate ligament of the human when the ligament insertion hole was formed in the tibia member like the practical example.

As illustrated in FIGS. 51 to 60, in each bundle, it can be checked that the bundle length changes according to the knee bending angle. It can be checked that the angles at which the tension and relief states are generated vary in each bundle. For example, in the bundles 1, 2, 4, 5, and 11, the state (tension state) in which the bundle length does not change is maintained until the knee is deeply bent. On the other hand, in the bundles 17, 18, 19, and 20, the relief state is generated at the position where the knee is lightly bent, and the relief state progresses as the knee is deeply bent. That is, when the anterior cruciate ligament is regarded as one strip, it can be checked that the tension or relief state of the bundle changes variously according to the radial position or the angle about the center axis. Therefore, it was checked that the anterior cruciate ligament was connected to the tibia member or femur to a certain degree to disperse various functions of the anterior cruciate ligament.

Figure 61:
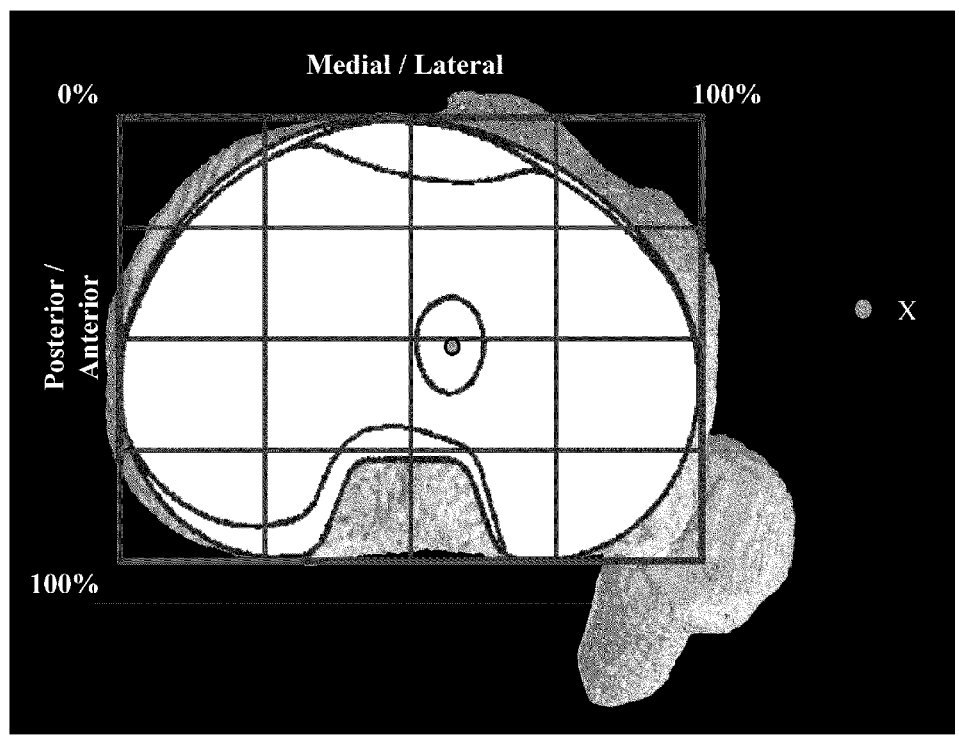
FIG. 61 is a view illustrating the joining position (ligament insertion hole) relationship between the anterior cruciate ligament and the tibia in a simulation of a comparative example.
Figure 62:
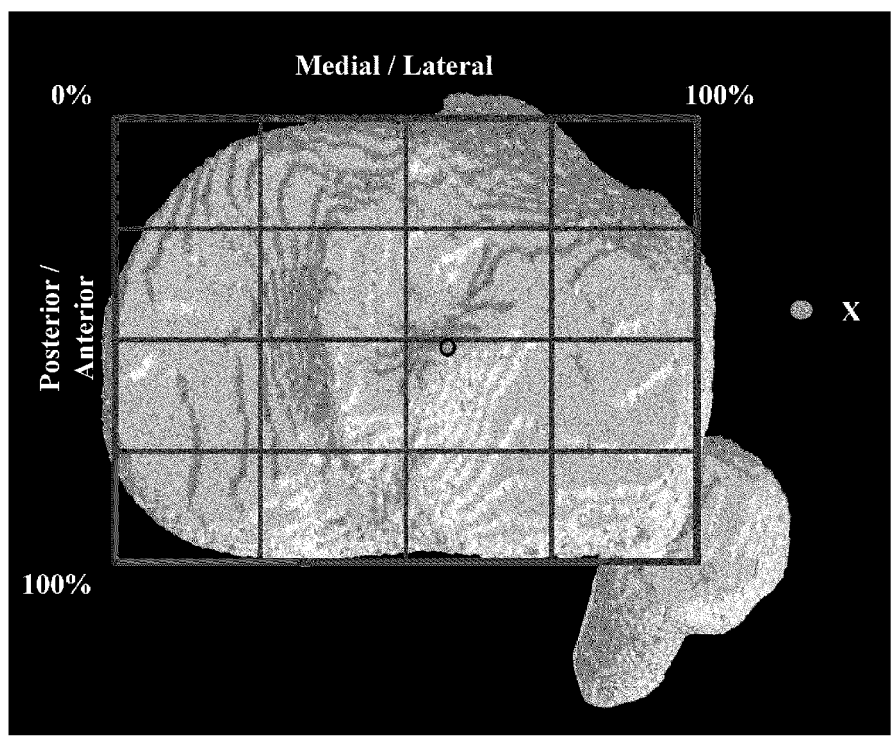
FIG. 62 is a view illustrating the joining position (ligament insertion hole) relationship between the anterior cruciate ligament and the tibia in the simulation of the comparative example.
Figure 63:
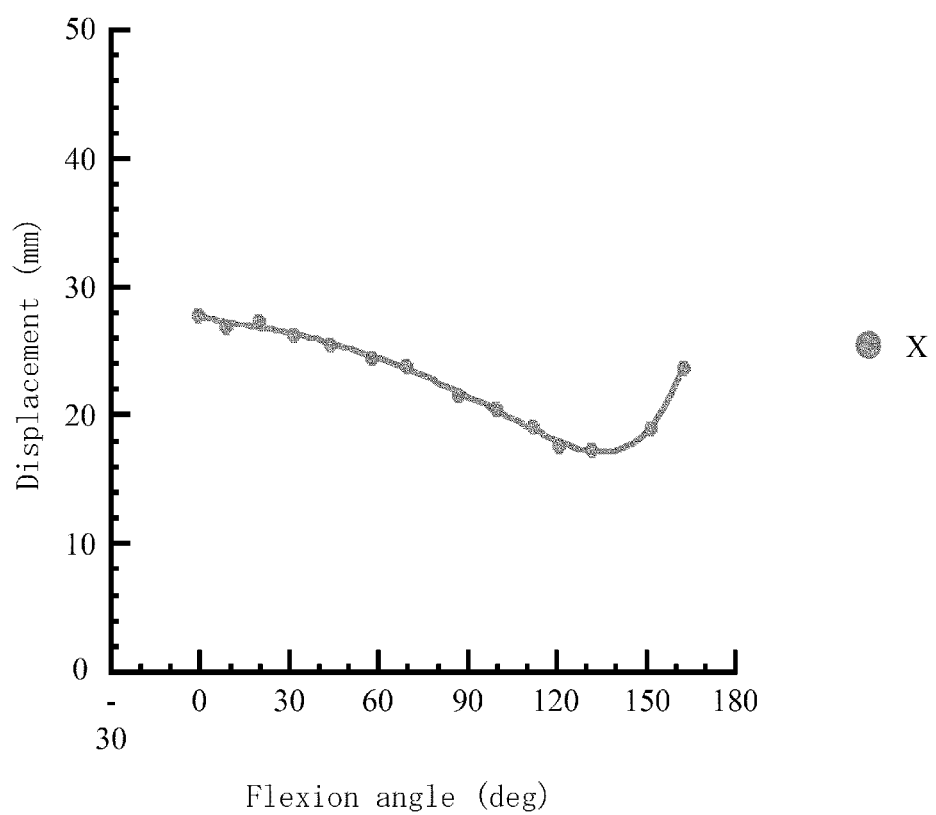
FIG. 63 is a view illustrating a relationship between the bending angle of the knee and the length of the anterior cruciate ligament in the comparative example.

On the other hand, the case that the ligament was coupled to the position as illustrated in FIGS. 61 and 62 in the tibia member was simulated as a comparative example. As illustrated in FIG. 63, in the comparative example, it was checked that the tendencies of the knee bending angle and the change in length of the anterior cruciate ligament was different from the tendency of the anterior cruciate ligament (DEFORT) of the human by increasing the knee bending angle. Because the position as illustrated in FIGS. 61 and 62 differed from an originally anatomical position at which the tibia member and the ligament are coupled together, it was checked that the anterior cruciate ligament took the extreme tension pattern. Therefore, it was clear that the tension pattern of the originally normal knee was hardly generated unless the ligament was coupled to a proper position. That is, it was checked that the anterior cruciate ligament reconstructed at the proper position was not able to exert the sufficient function.

(Interference State Between Anterior Cruciate Ligament and Intercondylar Eminence)

In the practical example, how each bundle of reconstruction ligaments constituting the anterior cruciate ligament interfered with the intercondylar eminence in bending the knee was checked by the simulation. In the simulation, the state in which the bundle of reconstruction ligaments interfered with the intercondylar eminence was checked with respect to the case where the knee was bent by each of angles 112 degrees, 121 degrees, and 131 degrees.

Each bundle of reconstruction ligaments was connected to the tibia member and the femur at the positions in FIGS. 46 to 49.

Figure 64:
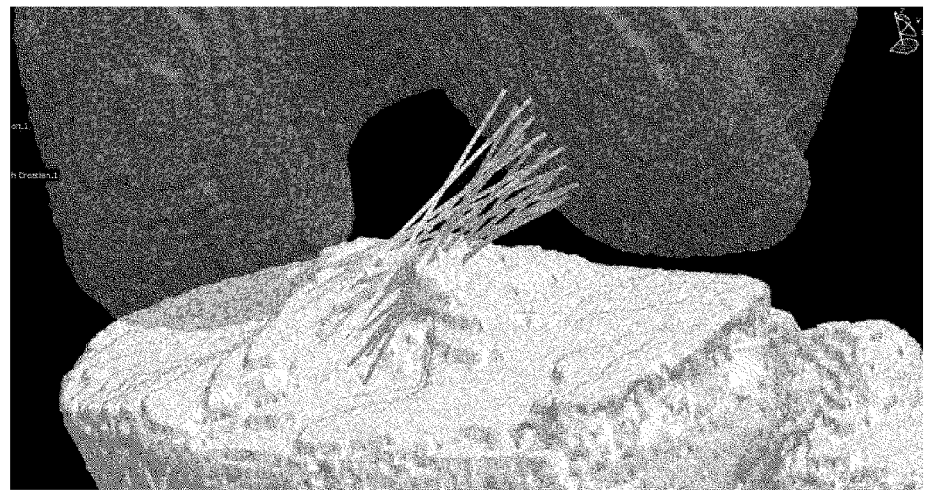
FIG. 64 is a view illustrating a simulation of an interference state between the anterior cruciate ligament and an intercondylar eminence.
Figure 64:
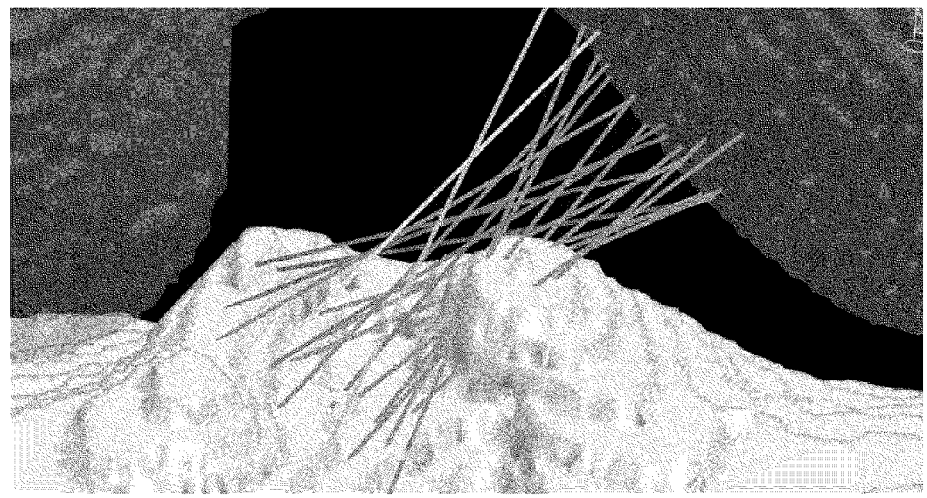
Figure 65:
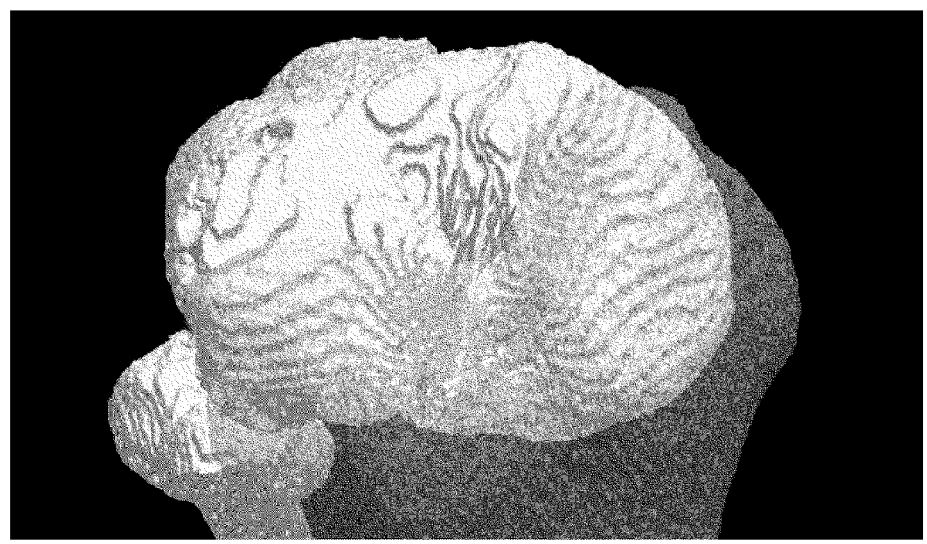
FIG. 65 is a view illustrating the simulation of the interference state between the anterior cruciate ligament and the intercondylar eminence, and illustrating a simulation result of the state in which the knee is bend by 131 degrees.
Figure 65:
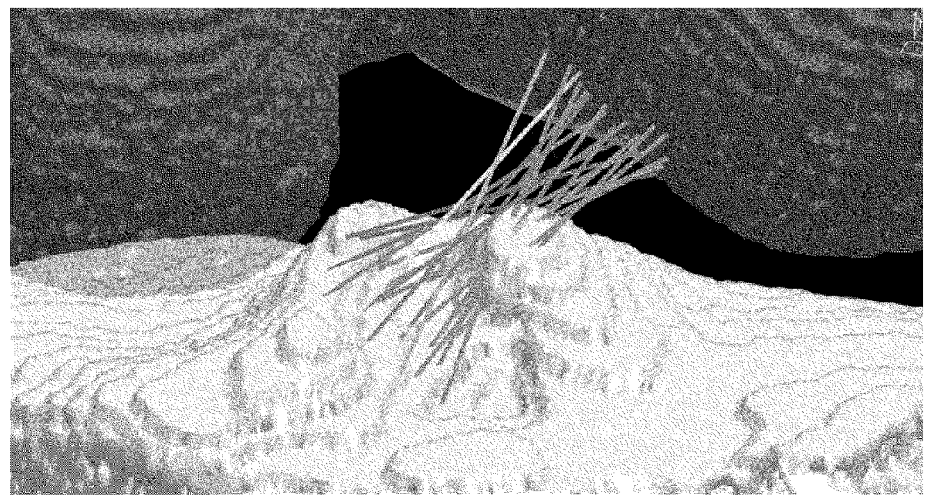

As illustrated in FIGS. 64 and 65, it was checked that, in the plural bundles of reconstruction ligaments constituting the anterior cruciate ligament, the bundle (PL group) located on the rear side interfered strongly with the intercondylar eminence by bending the knee while the bundle (AM group) located on the front side interfered weakly with the intercondylar eminence. It was checked that the interference was crowded as the knee was deeply bent, and that the tensile force closer to the anterior cruciate ligament of a living body was able to be generated when the anterior cruciate ligament was reconstructed using not one reconstruction ligament but the plural bundles of reconstruction ligaments.

INDUSTRIAL APPLICABILITY

The ligament reconstruction type artificial knee joint of the present invention is suitable for the artificial knee joint used in the total knee replacement in the treatment of the knee osteoarthritis, the joint rheumatism, or the like.

DESCRIPTION OF REFERENCE SIGNS

1 artificial knee joint
10 femur member
11 medial condyle
12 lateral condyle
13 lateral condyle inside wall
14 engagement part
15 medial condyle inside wall
16 posterior cruciate ligament engagement part
20 tibia member
20*a* base part
20*b* contact part
20*h* fixing hole
20*s* notch
21 medial condyle
22 lateral condyle
23 intercondylar eminence
30 artificial ligament
31 coupling member
51 posterior cruciate ligament coupling member
F femur DT distal end
T tibia
PE proximal end
ACL anterior cruciate ligament
PCL posterior cruciate ligament

The invention claimed is:

1. A ligament reconstruction type artificial knee joint used in a total knee replacement of an original knee, the artificial knee joint comprising:
   a femur member configured to be mounted on a femur distal end;
   a tibia member configured to be mounted on a tibia proximal end;
   a ring-shaped artificial ligament configured to couple the tibia member and the femur member together, wherein the artificial ligament, as a whole, is a ring shape; and
   a coupling member to which the artificial ligament is configured to be coupled,
   wherein the femur member includes a wall-shaped lateral condyle inside wall, which is disposed on a side of a lateral condyle of the femur member that is closest to a medial condyle of the femur member,
   wherein the femur member includes an engagement part in the lateral condyle inside wall on which one end of the artificial ligament is configured to be hooked, wherein, when the femur member is mounted on the femur distal end, the engagement part is at a position where at least a portion of an anterior cruciate ligament was previously positioned in the original knee, such that the artificial ligament pierces the lateral condyle inside wall,
   wherein the tibia member defines a fixing hole on an upper side of the tibia member in which the coupling member is configured to be fixedly inserted, wherein the fixing hole is at a position where at least a portion of the anterior cruciate ligament was previously positioned in the original knee,
   wherein the coupling member defines a pair of through-holes extending through one end face of the coupling member, and the artificial ligament is hooked to the coupling member when the artificial ligament is inserted in the pair of through-holes,
   wherein the engagement part defines a pair of engagement holes on which the artificial ligament is hooked to the engagement part, and
   the pair of engagement holes is configured such that a twist is generated in the artificial ligament when the artificial ligament is hooked to the coupling member and the engagement part and when the coupling member is mounted in the fixing hole of the tibia member.

2. The ligament reconstruction type artificial knee joint according to claim 1, wherein a substantially V-shaped groove is formed around the engagement part such that a leading end of the engagement part is directed toward a front of the artificial knee joint, the groove piercing the lateral condyle inside wall, and
   wherein the pair of engagement holes communicate with the groove and are defined in a base end of the engagement part.

3. The ligament reconstruction type artificial knee joint according to claim 2, further comprising a detachment preventing mechanism in the lateral condyle inside wall of the femur member, the detachment preventing mechanism configured to prevent one end of the artificial ligament from being detached from the engagement part,
   wherein the detachment preventing mechanism includes:
      a female screw hole defined in the groove formed around the engagement part; and
      a male screw member configured to engage with the female screw hole.

4. The ligament reconstruction type artificial knee joint according to claim 1, wherein, the coupling member includes: a pair of enlarged-diameter parts provided at both ends in an axial direction; and a neck part on which the artificial ligament disposed between the pair of enlarged-diameter parts is hooked,
   wherein the coupling member defines a notch in which the artificial ligament is disposed in one of the pair enlarged-diameter parts that is disposed on a top surface side of the tibia member when the coupling member is mounted in the fixing hole of the tibia member,
   wherein a substantially V-shaped groove is formed around the engagement part such that a leading end of the engagement part is directed toward a front of the artificial knee joint, the groove piercing the lateral condyle inside wall,
   wherein the pair of engagement holes communicate with the groove and are defined in a base end of the engagement part, and
   wherein the pair of engagement holes is arrayed in a direction such that the twist is generated in the artificial ligament when the artificial ligament is hooked on the pair of engagement holes and when the coupling member is mounted in the fixing hole of the tibia member.

5. The ligament reconstruction type artificial knee joint according to claim 1, further comprising:
   an artificial posterior cruciate ligament configured to connect the tibia member and the femur member together; and
   a posterior cruciate ligament coupling member to which the artificial posterior cruciate ligament is configured to be coupled,
   wherein the femur member includes a wall-shaped medial condyle inside wall, which is disposed on a side of the medial condyle of the femur member that is closest to the lateral condyle of the femur member,
   wherein the femur member includes a posterior cruciate ligament engagement part in the medial condyle inside wall on which one end of the artificial ligament is configured to be hooked, wherein, when the femur member is mounted on the femur distal end, the posterior cruciate ligament engagement part is at a position where at least a portion of a posterior cruciate ligament was previously positioned in the original knee, such that the artificial posterior cruciate ligament pierces the medial condyle inside wall, and
   wherein the tibia member defines a notch in a rear portion of the tibia member in which the posterior cruciate ligament coupling member is configured to be disposed, wherein the posterior cruciate ligament coupling member is at a position where at least a portion of the posterior cruciate ligament was previously positioned in the original knee.

6. The ligament reconstruction type artificial knee joint according to claim 5, wherein the artificial posterior cruciate ligament is a ring shape,
   wherein the posterior cruciate ligament coupling member defines a pair of posterior cruciate ligament through-holes extending through one end face of the posterior cruciate ligament coupling member, and the artificial posterior cruciate ligament is hooked on the pair of posterior cruciate ligament through-holes when the artificial posterior cruciate ligament is inserted in the pair of posterior cruciate ligament through-holes, a substantially V-shaped groove is formed around the posterior cruciate ligament engagement part such that a leading end of the posterior cruciate ligament engagement part is directed toward a front of the artificial knee joint, the groove piercing the medial condyle inside wall, wherein the posterior cruciate ligament engagement part defines a pair of posterior cruciate ligament engagement holes in a base end of the posterior cruciate ligament engagement part, wherein the pair of posterior cruciate ligament engagement holes communicate with the groove, and wherein, in the posterior cruciate ligament engagement part, the pair of posterior cruciate ligament engagement holes is arrayed in a direction such that the twist is generated in the artificial posterior cruciate ligament when the artificial posterior cruciate ligament is hooked on the pair of posterior cruciate ligament engagement holes and when the posterior cruciate ligament coupling member is mounted in the notch of the tibia member.

7. The ligament reconstruction type artificial knee joint according to claim 6, further comprising a detachment preventing mechanism in the medial condyle inside wall of the femur member, the detachment preventing mechanism configured to prevent one end of the artificial posterior cruciate ligament from being detached from the posterior cruciate ligament engagement part, wherein the detachment preventing mechanism includes:
a female screw hole defined in the groove formed around the posterior cruciate ligament engagement part; and
a male screw member configured to engage with the female screw hole.

8. The ligament reconstruction type artificial knee joint according to claim 1, wherein an upper surface of a medial condyle of the tibia member is formed into a concave surface and an upper surface of a lateral condyle of the tibia member is formed into a flat surface.

9. The ligament reconstruction type artificial knee joint according to claim 8, wherein the tibia member includes an intercondylar eminence between the medial condyle and the lateral condyle of the tibia member, and
a height of the intercondylar eminence is substantially equal to a height of an intercondylar eminence in the original knee.

10. The ligament reconstruction type artificial knee joint according to claim 1, wherein a medial condyle of the tibia member is formed so as to tilt backward with respect to a lateral condyle of the tibia member.

11. The ligament reconstruction type artificial knee joint according to claim 1, wherein respective surfaces of a medial condyle and a lateral condyle of the tibia member tilt inward.

12. The ligament reconstruction type artificial knee joint according to claim 1, wherein respective peripheral portions of a medial condyle and/or a lateral condyle of the tibia member are formed into a curved shape.

13. The ligament reconstruction type artificial knee joint according to claim 12, wherein a boundary portion between a side surface and/or a rear surface of the tibia member and the lateral condyle of the tibia member is formed into an outward convex surface.

14. A ligament reconstruction type artificial knee joint used in a total knee replacement of an original knee, the artificial knee joint comprising:
a femur member configured to be mounted on a femur distal end;
a tibia member configured to be mounted on a tibia proximal end;
an artificial ligament configured to couple the tibia member and the femur member together, wherein the artificial ligament includes a plurality of ligament members that are each, as a whole, in a ring shape; and
a femur coupling member and a tibia coupling member, which are configured to be coupled to the artificial ligament,
wherein the femur member includes a wall-shaped lateral condyle inside wall, which is disposed on a side of a lateral condyle of the femur member that is closest to a medial condyle of the femur member,
wherein the femur member defines a femur fixing hole in the lateral condyle inside wall in which the femur coupling member is configured to be fixed, wherein, when the femur member is mounted on the femur distal end, the femur fixing hole is at a position where at least a portion of an anterior cruciate ligament was previously positioned in the original knee,
wherein the tibia member defines a tibia fixing hole on an upper side of the tibia member in which the tibia coupling member is configured to be fixed, wherein the tibia fixing hole is at a position where at least a portion of the anterior cruciate ligament was previously positioned in the original knee,
wherein, when the femur coupling member is fixed in the femur fixing hole on the lateral condyle inside wall of the femur member, the plurality of ligament members are coupled to the femur coupling member such that one end of each of the plurality of ligament members is disposed within a certain area that includes a center portion of where at least a portion of the anterior cruciate ligament was previously positioned in the original knee,
wherein, when the tibia coupling member is fixed in the tibia fixing hole on the upper side of the tibia member, the plurality of ligament members are coupled to the tibia coupling member such that the other end of each of the plurality of ligament members is disposed within a certain area that includes a center portion of where at least a portion of the anterior cruciate ligament was previously positioned in the original knee, and
the femur coupling member and the tibia coupling member are configured to be mounted on the femur member and the tibia member, respectively, such that a twist is generated in the plurality of ligament members between the femur coupling member and the tibia coupling member.

15. The ligament reconstruction type artificial knee joint according to claim 14, wherein one end face of the femur coupling member defines a plurality of ligament insertion holes, wherein each of the plurality of ligament members is configured to be inserted in a pair of ligament insertion holes of the plurality of ligament insertion holes to hook the plurality of ligament members to the femur coupling member, wherein one end face of the tibia coupling member defines a plurality of ligament insertion holes, wherein each of the plurality of ligament members is configured to be inserted in a pair of ligament insertion holes of the plurality of ligament insertion holes to hook the plurality of ligament members to the tibia coupling member.

\* \* \* \* \*